(12) United States Patent
Sorscher et al.

(10) Patent No.: US 6,491,905 B1
(45) Date of Patent: *Dec. 10, 2002

(54) RECOMBINANT BACTERIAL CELLS FOR DELIVERY OF PNP TO TUMOR CELLS

(75) Inventors: Eric J. Sorscher, Birmingham, AL (US); William B. Parker, Birmingham, AL (US); William Waud, Mountain Brook, AL (US); Vijayakrishna K. Gadi, Birmingham, AL (US); Leonard L. Bennett, Jr., Birmingham, AL (US)

(73) Assignees: The UAB Research Foundation, Birmingham, AL (US); Southern Research Institute, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/183,188

(22) Filed: Oct. 30, 1998

Related U.S. Application Data

(63) Continuation-in-part of application No. 08/881,772, filed on Jun. 24, 1997, now Pat. No. 6,017,896, and a continuation-in-part of application No. 08/702,181, filed on Aug. 23, 1996, now abandoned, which is a continuation-in-part of application No. 08/122,321, filed on Sep. 14, 1993, now Pat. No. 5,552,311.

(60) Provisional application No. 60/064,676, filed on Oct. 31, 1997.

(51) Int. Cl.⁷ .......................... C12N 1/20; C12N 15/63; C12N 15/00; C07H 21/04; A01N 63/00

(52) U.S. Cl. ................ 424/93.2; 435/252.3; 435/252.7; 435/325; 435/455; 435/320.1; 536/23.2; 536/23.7; 424/93.1

(58) Field of Search .............................. 435/325, 440, 435/455, 252.3, 254.2, 252.7, 320.1; 514/2, 44; 536/23.2, 23.7; 424/93.1, 93.2

(56) References Cited

U.S. PATENT DOCUMENTS

| | | | |
|---|---|---|---|
| 5,552,311 A | * | 9/1996 | Sorscher et al. ............. 435/325 |
| 6,017,896 A | * | 1/2000 | Sorscher et al. ............. 514/44 |

FOREIGN PATENT DOCUMENTS

| | | |
|---|---|---|
| EP | 0 415 731 A2 | 6/1991 |
| EP | 0 392 745 B1 | 2/1994 |

OTHER PUBLICATIONS

Tang et al., Gongye Weishengwu, 19: 1–5, 1989.*
Fox et al., Gene Therapy vol. 3, p. 173–178, 1996.*
Allen (1989) Stealth(TM) Liposomes: Avoiding Reticuloendothelial uptake. Liposomes in the Therapy of Infectious Diseases and Cancer, pp. 405–415.
Anderson (1992) Human Gene Therapy. Science, 256:808–813.
Bagshawe (1989) Towards generating cytotoxic agents at cancer sites. J. Cancer, 60:275–281.
Balzarini et al. (1993) J. Biol. Chem., 268(9):6332–6337.
Barankiewicz and Jezewska (1976) Inosine–guanosine and adenosine phosphorylase activities in hepatopancreas of helix pomatia (gastropoda). Comp. Biochem. Physiol., vol. 54B, pp. 239–242.
Bennett et al. (1984) Mode of action of a–amino–6–chloro–1–deazapurine. Biochemical Pharmacology, vol. 33, No. 2, ppl 261–271.
Bohman et al. (1983) Mechanism of cytostatic action of novel 5–(Thien–2–yl) and 5–Furan–2yl)–substituted pyrimidine nucleoside analogues against tumor cells transfected by the thymidine kinase gene of herpes simplex virus. The Journal of Biological Chemistry, vol. 269, No. 11, ppl. 8036–8043.
Brockman et al. (1980) Metabolism and chemotherapeutic activity of 9–β–D–Arabinofuranosyl–2–fluoroadenine against murine leukemia L1210 and evidence for its phosphorylation by deoxycytidine kinase. Cancer Research, 40:3610–3615.
Bruce and Meeker (1967) J. Natl. Cancer Inst., 38:401–405.
Burland et al. (1995) Analysis of the *Escherichia coli* genome VI: DNA sequence of the region from 92.8 through 100 minutes. Nucleic Acids Research, vol. 23, No. 12, pp. 2105–2119.
Carson et al. (1980) Deoxycytidine kinase–mediated toxicity of deoxyadenosine analogs toward malignant human lymphoblasts in vitro and toward murine L1210 leukemia in vivo. Proc. Natl. Acad. Sci. USA, vol. 77, No. 11, pp. 6865–6869.
Collier (1988) Structure–activity relationship in the *Pseudomonas aeruginosa* exc. In Immunotoxins, A.E. Frankel, Ed. (Kluwer Academic Publishers, Boston), pp. 25–35.
Connors (1995) The choice of prodrugs for gene directed enzyme prodrug therapy of cancer. Gene Therapy, 2:702–709.
Culver et al. (1991) In vivo gene transfer with retroviral vector–producer cells for treatment of experimental brain tumors. Proc. Natl. Acad. Sci. USA, 88:3155–3159.*

(List continued on next page.)

Primary Examiner—Scott D. Priebe
Assistant Examiner—Shin-Lin Chen
(74) Attorney, Agent, or Firm—Gifford, Krass, Groh, Sprinkle, Anderson & Citkowski, P.C.

(57) ABSTRACT

The present invention provides a procaryotic host cell stably transformed or transfected by a vector including a DNA sequence encoding for purine nucleoside phosphorylase or hydrolase. The transformed or transfected procaryotic host cell can be used in combination with a purine substrate to treat tumor cells and/or virally infected cells.

21 Claims, 19 Drawing Sheets

OTHER PUBLICATIONS

Culver et al. (1992) Lymphocytes as cellular vehicles for gene therapy in mouse and man. Science, 256:1550–1552.*

Culver et al. (1994) Gene therapy for cancer. Trends in Genetics, 10:174–178.*

Curiel et al. (1992) High–efficiency gene transfer mediated by adenovirus coupled to DNA–polylsine complexes. Hum. Gene Ther., 3:147–154.*

Da Costa et al. (1996) Converting cancer genes into killer genes. Proc. Natl. Acad. Sci. USA, 93:4192–4196.*

Dadonna et al. (1986) Expression of human malaria parasite purine nucleoside phosphorylase in host enzyme–deficient erythrocyte culture. The Journal of Biological Chemistry, vol. 261, No. 25, Issue of Sep. 5, pp. 11667–11673.*

Debs et al. (1987) Selective enhancement of pentamidine uptake in the lung by aerosolization and delivery in liposomes. Am. Rev. Respir. Dis., 135:731–737.*

Dewey and Kidder (1973) Partial purification and properties of a nucleoside hydrolase from crithidia. Archives of Biochemistry and Biophysics, 157:380–387.*

Doskocil and Holy (1977) Specificity of purine nucleoside phosphorylase from *Escherichia coli*. Collection Czechoslov. Chem. Commnun., 42:370–383.*

Dykes et al. (1992) Development of human tumor zenograft models for in vivo evaluation of new antitumor drugs. Contri. Oncol. Basel, Karger, 42:1–22.*

Ealick et al. (1990) Three–dimensional structure of human erythrocytic purine nucleoside phosphorylase at 3.2 A resolution. The Journal of Biological Chemistry, vol. 265, No. 3, pp. 1812–1820.*

Fox et al. (1996) Anaerobic bacteria as a delivery system for cancer gene therapy: In vitro activation of 5–fluorocytosine by genetically engineered clostridia. Gene Therapy, 9:173–178.*

Freeman et al. (1996) In situ use of suicide genes for cancer therapy. Seminars in Oncology, 23:31–45.

Freireich et al. (1966) Quantitative comparison of toxicity of anticancer agents in mouse, rat, hamster, dog, monkey, and man. Cancer Chemotherapy Reports, vol. 50, No. 4, pp. 219–244.

Friedmann (1989) Progress toward human gene therapy. Science, 244:1275–1281.

Gabizon and Papahadiopoulos (1988) Liposome formulations with prolonged circulation time in blood and enhanced uptake by tumors. Proc. Natl. Sci. USA, 85:6949–6953.

Garver et al. (1994) Strategy for achieving selective killing of carcinomas. Gene Therapy I., 46–50.

Gay (1984) Construction and characterization of an *Escherincia coli* strain with a uncI mutations. J. Bacteriol, 158:820–825.

Ghoda et al. (1988) Substrate specificities of 5'–deoxy–5'–methylthioadenosine phosphorylase from *Trypansoma brucei* brucei and mammalian cells. Molecular and Biochemical Parasitology, 27:109–118.

Giebel et al. (1991) Organization and nucleotide sequences of the human tyrosinase gene and a truncated tyrosinase–related segment. Genomics, 9:435–445.

Gutteridge and Davies (1981) Enzymes of purine salvage in trypanosoma cruzi. FEBS Letters, vol. 127, No. 2, pp. 21–24.

Hatanka et al. (1975) Adenine formation from adenosine by mycoplasmas: adenosine phosphorylase activity. Proc. Natl. Acad. Sci. USA, 72:1401–1405.

Hershfield et al. (1991) Use of site–directed mutagenesis to enhance the epitope–shielding effect of covalent modification of proteins with polyethylene glycol. Proc. Natl. Acad. Sci. USA, 88:7185–7189.

Heyworth et al. (1982) Purine metabolism in trichomonas vaginalis. FEBS Letters, vol. 1, No. 1, pp. 106–110.

Hooper and Subak–Sharpe (1981) Metabolic cooperation between cells. Internat'l Rev. of Cytol., 69:45–104.

Houston (1988) Introduction. In Immunotoxins. A.E. Frankel, Ed (Kluwer Academic Publishers, Boston) pp. 1–7.

Huang et al. (1992) Pharmacokinetics and therapeutics of sterically stabilized liposomes in mice bearing C–26 colon carcinoma. Cancer Research, 52:6774–6781.

Huber et al. (1991) Retroviral–mediated gene therapy for the treatment of hepatocellular carcinoma: an innovative approach for cancer therapy. Proc. Acad. Sci. USA, 88:8039–8043.

Hughes et al. (1995) Bystander killing of melanoma cells using the human tyrosinase promoter to express the *Escherichia coli* purine nucleoside phosphorylase gene. Cancer Research, 55:3339–3345.

Jensen (1978) Two purine nucleoside phosphorylases in bacillus subtilis purification and some properties of the adenosine–specific phosphorylase. Biochimica et Biophysics Acta, 525:346–356.

Jensen and Nygaard (1975) Purine nucleoside phosphorylase from *Escherichia coli* and *Salmonella typhimurium*. Eur. J. Biochem., 51:253–265.

Jenuth and Snyder (1991) Nucleotide sequence of murine purine nucleoside phosphorylase cDNA. Nucleic Acids Research, vol. 19, No. 7, p. 1708.

JIAO et al. (1993) Long–term correction of rat model of Parkinson's disease by gene therapy. Nature, 362:450–453.

Kidder et al. (1979) The purine phosphoribosyltransferases of crithidia fasciculata. J. Parasitol., 64(4), pp. 520–525.

Kikuchi et al. (1989) Characteristic sequences in the upstream region of the human tyrosinase gene. Biochimica at Biophysica Acta., 1009:283–286.

Kolls et al. (1994) Prolonged and effective blockade of tumor necrosis factor activity through adenovirus–mediated gene transfer. Proc. Natl. Acad. Sci, USA, vol. 91, pp. 215–219.

Kolata (Jul. 25, 1995). The New York Times, p. C3.

Konigk (1978) Purine nuceltide metabolism in promastigotes of leishmania tropica: inhibitory effect of allopurinol and analogues of purine nucleosides. Tropemed. Parasit., 29:435–438.

Koszalka and Krenitsky (1979) Nucleosidases from *Leishmania donovani*. The Journal of Biological Chemistry, vol. 254, No. 17, issue of Sep. 10, pp. 8185–8193.

Lapointe and Portelance (1978) Growth retardation and prevention of ehrlich solid tumor by *Clostridium perfringes* Type A spores and culture supernatant. Cancer Research, 38:295–230.

Litzinger and Huang (1992) Biodistribution and immunotargetability of ganglioside–stabilized dioleoylphosphatidylethanolamine liposomes. Biochimica at Biophysica Acta., 1104:179–187.

Long et al. (1977) Uracil prosphoribosyl transferase activity of mycoplasma and infected cell cultures. In vitro, 13:429–433.

Maruvama et al. (1990) Lipid composition is important for highly efficient target binding and retention of immunoliposomes. Proc. Natl. Acad. Sci. USA, 87:5744–5748.

Maxwell et al. (1986) Regulated expression of a diphtheria toxin–a–chain gene transfected into human cells: possible strategy for inducing cancer cell suicide. Cancer Research, 46:4660–4664.

McElwain et al. (1988) Acholeplasma laidlawii B–PG–9 adenine–specific purine nucleoside phosphorylase that accepts ribose–1–phosphate, deoxyribose–1–phosphate, and xylose–1–phosphate. Journal of Bacteriology, 170:564–567.

McGarrity and Carson (1982) Adenosine phosphorylase–mediate nucleoside toxicity. Experimental Cell Research, 139:199–206.

McGarrity et al. (1986) In Vitro Cell. & Dev. Biol., 22(6):301–304.

Miech et al. (1975) Pathways of nucleotide metabolism in schistosoma mansoni–vi–adenosine phosphorylase. Biochemical Pharmacology, 24:407–411.

Miller (1992) Human gene therapy comes of age. Nature, 357:455–460.

Miller and Rosman (1989) Improved retroviral vectors for gene transfer and expression. BioTechniques, 7:980–991.

Montgomery and Howson (1968) Analogs of 6–methyl–9–$\beta$ – D–ribofuranosylpurine. J. Med. Chem., 11:48–52.

Moolten (1986) Tumor chemosensitivity conferred by inserted herpes thymidine kinase genes: paradigm for a prospective cancer control strategy. Cancer Res., 46:5276–5281.

Moolten and Well (1990) Curability of tumors bearing herpes tymidine kinase genes transferred by retroviral vectors. J. Natl. Cancer. Inst., 82:297–300.

Moolten (1994) Drug sensitivity ("suicide") genes for selective cancer chemotherapy. Cancer Gene Therapy, 1:279–287.

Mullen et al. (1992) Proc. Natl. Acad. Sci. USA, 89:33–37.

Mullen (1994) Metabolic suicide genes in gene therapy. Pharmac. Ther., 63:199–207.

Murphy (1985) The diphtheria toxin structural gene. Current Topics in Microbiology and Immunology, 118:235–251.

Nabel et al. (1992) Immunotherapy of malignancy by in vivo gene transfer into tumors. Human Gene Therapy, 3:399–410.

Nelson et al. (1992) Isolation and expression of a murine purine nucleoside phosphorylase–encoding cDNA and sequence similarity with the human message. Gene, 113:215–221.

Parks et al. (1988) Purine nucleoside phosphorylase and 5'–methylthioadenosine phosphorylase: targets of chemotherapy. In Molecular Actions and Targets for Cancer Chemotherapeutic Agents (Academic Press, Inc.) pp. 229–252.

Pinnaduwage and Huang (1992) Stable target–sensitive immunoliposomes. Biochemistry, 31:2850–2855.

Ram et al. (1993) In situ retroviral–mediated gene transfer for the treatment of brain tumors in rats. Cancer Research, 53:83–88.

Reese (1968) Extracellular purine B–ribosidases from fungi. Canadian Journal of Microbiology, 14:377–383.

Robertus, Toxin Structure. In Immunotoxins. A.E. Frankel, Ed. (Kluwer Academic Publishers, Boston). pp. 11–23.

Rosenberg et al. (1990) Gene transfer into humans–immunotherapy of patients with advanced melanoma using tumor infiltrating lymphocytes modifed by retroviral gene transduction. New England J. Med., 323:570–578.

Schmidt et al. (1975) A purine nucleoside hydrolase from trypanosoma gambiense, purification and properties. Tropenmed. Parasit., 26:19–26.

Senesi et al. (1976) A specific adenosine phosphorylase, distinct from purine nucleoside phosphorylase. FEBS Letters, vol. 64, No. 2, pp. 353–357.

Senter (1990) Activation of prodrugs by antibody–enzyme conjugates: a new approach to cancer therapy. Faseb J., 4:188–193.

Senter et al. (1988) Anti–tumor effects of antibody–alkaline phosphatase conjugates in combination with etoposide phosphate. Proc. Natl. Acad. Sci. USA, 85:4842–4846.

Senter et al. (1989) Enhancement of the in vitro and in vivo antitumor activities of phosphorylated mitomycin C and etoposide derivatives my monoclonal antibody–alkaline phosphatse conjugates. Cancer Research, 49:5789–5792.

Shibata et al. (1992) Identification of a cis–acting element that enhances the pigment cell–specific expression of the human tyrosinase gnee. The Journal of Biological Chemistry, vol. 267, No. 29, pp. 20584–20588.

Shirae and Yokozeki (1991) Purifications and properties of orotidine–phosphorolying enzyme and purine nucleoside phosphorylase from Erwinia carotovora AJ 2992 Agric. Biol. Chem., 55(7), 1849–1857.

Sorrentino et al. (1992) Selection of drug–resistant bone marrow cells in vivo after retroviral transfer of human MDR1. Science, 257(5066); 99–103.

Sorscher et al. (1992) Identification of a membrane protein from T84 cells using antibodies made against a DIDS–binding peptide. Amer. J. Physiol., 262:C136–C147.

Sorscher et al. (1991) Diagnosis of genetic disease by primer–specified restriction map modification, with application to cystic fibrosis and retinitis pigmentosa. The Lancet, vol. 337, pp. 1115–1118.

Sorscher et al. (1994) Tumor cell bystander killing in colonic carcinoma utilizing the Escherichia coli DeoD gene to generate toxic purines. Gene Therapy, 1:233–238.

Stoeckler et al. (1997) Purine nucleoside phosphorylase. 3. Reversal of purine base specificity by site–directed mutagenesis. Biochemistry, vol. 36., No. 39, pp. 11749–11756.

Streeter et al. (1980) 7–ribosyl–3–deazaguinine–mechanism of antibacterial action. Biochemical Pharmacology, vol. 29, pp. 1791–1797.

Takamiya et al. (1992) Gene therapy of malignant brain tumors: a rat glioma line bearing the herpes simplex virus type 1–thymidine kinase gene and wild type retrovirus kills other tumor cells. J. Neurosci. Resc., 33:493–503.

Tannock (1989) Prinicples of cell proliferation: cell kinetics in cancer. In Principles and Practice of Oncology. Devita and Hellman, eds. (L.B. Lippincott, Philadelphia) pp. 3–13.

Tapscott et al. (1994) Gene therapy of rat 9L gliosarcoma tumors by transduction with selectable genes does not require drug selection. Proc. Natl. Acad. Sci. USA, vol. 91, pp. 8185–8189.

Tarr (1958) Lingcod muscle purine nucleoside phosphorylase. Can. J. Biochem. Physiol., 36:517–530.

Tepper et al. (1989) Murine interleukin–4 displays potent anti–tumor activity in vivo. Cell, 57:503–513.

Tham et al. (1993) Identification of Mycoplasma pirum genes involved in the salvage pathways for nucleosides. Journal of Bacteriology, vol. 175, No. 16, pp. 5281–5285.

Thompson (1992) At age 2, gene therapy enters a growth phase. Science, 358:744–746.

Trembacz and Jezewska (1993) Specific adenosine phosphorylase from hepatopancreas of gastropod helix pomatia. Comp. Biochem. Physiol., vol. 104B, No. 3, pp. 481–487.

Trinh et al. (1995) Enzyme/prodrug gene therapy: comparison of cytosine deaminanse/5–fluorocytosine versus thymidine kinase/ganciclovir enzyme/prodrug systems in a human colorectal carcinoma cell line. Cancer Research, 55:4808–4812.

Trubetskoy et al. (1992) Cationic liposomes enhance targeted delivery and expresion of exogenous DNA mediated by N–terminal modified poly(L–lysine)–antibody conjugate in mouse lung endothielial cells. Biochimica at Biophysica Acta., 1131:311–313.

Van Berkel et al. (1991) Receptor–dependent targeting of lipoproteins to specific cell types of the liver. Targeted Diagnosis and Therpapy, 5:225–249.

Wagner et al. (1990) Transferrin–polycation conjugates as carriers for DNA uptake into cells. Proc. Natl. Acad. Sci. USA, 87:3410–3414.

Wellhoner et al. (1991). J. Biol. Chem., 266:4309–4314.

White et al. (1982) Comparison of the actions of 9– –D–arabinofuranosyl–2–fluoroadenine and 9– –D–arabinofuranosyladenine on target enzymes from mouse tumor cells. Cancer Research, 42:2260–2264.

Williams et al. (1984) Human purine nucleoside phosphorylase cDNA sequence and genomic clone characterization. Nucleic Acids Research, vol. 12, No. 14, pp. 5779–5787.

Wu et al. (1988) Receptor–mediated gene delivery and expression in vivo. J. Biol. Chem., 263, 29:14621–14624.

Zhu et al. (1993) Science, 261:209–211.

Liposomes: A Practical Approach [Not available as of Dec. 3, 1998—will send if able to locate].

Tang et al. (1992) The nucleotide sequence of purine nucleoside phosphorylase gene from *Entrobacter aerogens* W8401. Gongye Weishengwu, 22:1.

Tang et al. (1989) Cloning and expression of the *Enterobacter aerogens* W8401 purine nucleoside phosphorylase gene in *Escherichia coli*. Gongye Weishengwu, 19:1–5.

* cited by examiner

FIG - 15A

```
GTTTGACAGCTTATCATCGACTGCACGGTGCACCAATGCTTCTGGCGTCAGGCAGCC
ATCGGAAGCTGTGGTATGGCTGT
GCAGGTCGTAAATCACTGCATAATTCGTGTCGCTCAAGGCGCACTCCCGTTCTGGAT
AATGTTTTTTGCGCCGACATCAT
AACGGTTCTGGCAAATATTCTGAAATGAGCTGTTGACAATTAATCATCCGGCTCGTAT
AATGTGTGGAATTGTGAGCGGA
TAACAATTTCACACAGGAAACAGCGCCGCTGAGAAAAGCGAAGCGGCACTGCTCTT
TAACAATTTATCAGACAATCTGT
GTGGGCACTCGACCGGAATTATCGATTAACTTTATTATTAAAAATTAAAGAGGTATA
TATTAATGTATCGATTAAATAAG
GAGGAATAAccATGGCTACCCCACACATTAATGCAGAAATGGGCGATTTCGCTGACG
TAGTTTTGATGCCAGGCGACCC
GCTGCGTGCGAAGTATATTGCTGAAACTTTCCTTGAAGATGCCCGTGAAGTGAACAA
CGTTCGCGGTATGCTGGGCTTCA
CCGGTACTTACAAAGGCCGCAAAATTTCCGTAATGGGTCACGGTATGGGTATCCCGT
CCTGCTCCATCTACACCAAAGAA
CTGATCACCGATTTCGGCGTGAAGAAAATTATCCGCGTGGGTTCCTGTGGCGCAGTT
CTGCCGCACGTAAAACTGCGCGA
CGTCGTTATCGGTATGGGTGCCTGCACCGATTCCAAAGTTAACCGCATCCGTTTTAAA
GACCATGACTTTGCCGCTATCG
CTGACTTCGACATGGTGCGTAACGCAGTAGATGCAGCTAAAGCACTGGGTATTGATG
CTCGCGTGGGTAACCTGTTCTCC
GCTGACCTGTTCTACTCTCCGGACGGCGAAATGTTCGACGTGATGGAAAAATACGGC
ATTCTCGGCGTGGAAATGGAAGC
GGCTGGTATCTACGGCGTCGCTGCAGAATTTGGCGCGAAAGCCCTGACCATCTGCAC
CGTATCTGACCACATCCGCACTC
ACGAGCAGACCACTGCCGCTGAGCGTCAGACTACCTTCAACGCATGATCAAAATCG
CACTGGAATCCGTTCTGCTGGGC
GATAAAGAGTAAAGAGTAAATCGATGGCCTGAATTCGAAGCTTGGGCTGTTTTGGCGG
ATGAGAGAAGATTTTCAGCCTGA
TACAGATTAAATCAGAACGCAGAAGCGGTCTGATAAAACAGAATTTGCCTGGCGGCA
GTAGCGCGGTGGTCCCACCTGAC
CCCATGCCGAACTCAGAAGTGAAACGCCGTAGCGCCGATGGTAGTGTGGGGTCTCCC
CATGCGAGAGTAGGGAACTGCCA
GGCATCAAATAAAACGAAAGGCTCAGTCGAAAGACTGGGCCTTTCGTTTTATCTGTT
GTTTGTCGGTGAACGCTCTCCTG
AGTAGGACAAATCCGCCGGGAGCGGATTTGAACGTTGCGAAGCAACGGCCCGGAGG
GTGGCGGGCAGGACGCCCGCCATA
AACTGCCAGGCATCAAATTAAGCAGAAGGCCATCCTGACGGATGGCCTTTTTGCGTT
TCTACAAACTCTTTTTGTTTATT
TTTCTAAATACATTCAAATATGTATCCGCTCATGAGACAATAACCCTGATAAATGCTT
CAATAATATTGAAAAAGGAAGA
GTATGAGTATTCAACATTTCCGTGTCGCCCTTATTCCCTTTTTTGCGGCATTTTGCCTT
CCTGTTTTTGCTCACCCAGAA
ACGCTGGTGAAAGTAAAAGATGCTGAAGATCAGTTGGGTGCACGAGTGGGTTACATC
```

FIG - 15B

```
GAACTGGATCTCAACAGCGGTAA
GATCCTTGAGAGTTTTCGCCCCGAAGAACGTTTTCCAATGATGAGCACTTTTAAAGTT
CTGCTATGTGGCGCGGTATTAT
CCCGTGTTGACGCCGGGCAAGAGCAACTCGGTCGCCGCATACACTATTCTCAGAATG
ACTTGGTTGAGTACTCACCAGTC
ACAGAAAAGCATCTTACGGATGGCATGACAGTAAGAGAATTATGCAGTGCTGCCATA
ACCATGAGTGATAACACTGCGGC
CAACTTACTTCTGACAACGATCGGAGGACCGAAGGAGCTAACCGCTTTTTTGCACAA
CATGGGGGATCATGTAACTCGCC
TTGATCGTTGGGAACCGGAGCTGAATGAAGCCATACCAAACGACGAGCGTGACACCA
CGATGCCTGTAGCAATGGCAACA
ACGTTGCGCAAACTATTAACTGGCGAACTACTTACTCTAGCTTCCCGGCAACAATTAA
TAGACTGGATGGAGGCGGATAA
AGTTGCAGGACCACTTCTGCGCTCGGCCCTTCCGGCTGGCTGGTTTATTGCTGATAAA
TCTGGAGCCGGTGAGCGTGGGT
CTCGCGGTATCATTGCAGCACTGGGGCCAGATGGTAAGCCCTCCCGTATCGTAGTTA
TCTACACGACGGGGAGTCAGGCA
ACTATGGATGAACGAAATAGACAGATCGCTGAGATAGCTGCCTCACTGATTAAGCAT
TGGTAACTGTCAGACCAAGTTTA
CTCATATATACTTTAGATTGATTTAAAACTTCATTTTTAATTTAAAAGGATCTAGGTG
AAGATCCTTTTTGATAATCTCA
TGACCAAAATCCCTTAACGTGAGTTTTCGTTCCACTGAGCGTCAGACCCCGTAGAAA
AGATCAAAGGATCTTCTTGAGAT
CCTTTTTTTCTGCGCGTAATCTGCTGCTTGCAAACAAAAAAACCACCGCTACCAGCGG
TGGTTTGTTTGCCGGATCAAGA
GCTACCAACTCTTTTTCCGAAGGTAACTGGCTTCAGCAGAGCGCAGATACCAAATAC
TGTCCTTCTAGTGTAGCCGTAGT
TAGGCCACCACTTCAAGAACTCTGTAGCACCGCCTACATACCTCGCTCTGCTAATCCT
GTTACCAGTGGCTGCTGCCAGT
GGCGATAAGTCGTGTCTTACCGGGTTGGACTCAAGACGATAGTTACCGGATAAGGCG
CAGCGGTCGGGCTGAACGGGGGG
TTCGTGCACACAGCCCAGCTTGGAGCGAACGACCTACACCGAACTGAGATACCTACA
GCGTGAGCTATGAGAAAGCGCCA
CGCTTCCCGAAGGGAGAAAGGCGGACAGGTATCCGGTAAGCGGCAGGGTCGGAACA
GGAGAGCGCACGAGGGAGCTTCCA
GGGGGAAACGCCTGGTATCTTTATAGTCCTGTCGGGTTTCGCCACCTCTGACTTGAGC
GTCGATTTTTGTGATGCTCGTC
AGGGGGGCGGAGCCTATGGAAAAACGCCAGCAACGCGGCCTTTTTACGGTTCCTGGC
CTTTTGCTGGCCTTTTGCTCACA
TGTTCTTTCCTGCGTTATCCCCTGATTCTGTGGATAACCGTATTACCGCCTTTGAGTG
AGCTGATACCGCTCGCCGCAGC
CGAACGACCGAGCGCAGCGAGTCAGTGAGCGAGGAAGCGGAAGAGCGCCTGATGCG
GTATTTTCTCCTTACGCATCTGTG
CGGTATTTCACACCGCATATGGTGCACTCTCAGTACAATCTGCTCTGATGCCGCATAG
TTAAGCCAGTATACACTCCGCT
```

FIG - 15C

ATCGCTACGTGACTGGGTCATGGCTGCGCCCCGACACCCGCCAACACCCGCTGACGC
GCCCTGACGGGCTTGTCTGCTCC
CGGCATCCGCTTACAGACAAGCTGTGACCGTCTCCGGGAGCTGCATGTGTCAGAGGT
TTTCACCGTCATCACCGAAACGC
GCGAGGCAGCAGATCAATTCGCGCGCGAAGGCGAAGCGGCATGCATTTACGTTGACA
CCATCGAATGGTGCAAAACCTTT
CGCGGTATGGCATGATAGCGCCCGGAAGAGAGTCAATTCAGGGTGGTGAATGTGAA
ACCAGTAACGTTATACGATGTCGC
AGAGTATGCCGGTGTCTCTTATCAGACCGTTTCCCGCGTGGTGAACCAGGCCAGCCA
CGTTTCTGCGAAAACGCGGGAAA
AAGTGGAAGCGGCGATGGCGGAGCTGAATTACATTCCCAACCGCGTGGCACAACAAC
TGGCGGGCAAACAGTCGTTGCTG
ATTGGCGTTGCCACCTCCAGTCTGGCCCTGCACGCGCCGTCGCAAATTGTCGCGGCG
ATTAAATCTCGCGCCGATCAACT
GGGTGCCAGCGTGGTGGTGTCGATGGTAGAACGAAGCGGCGTCGAAGCCTGTAAAG
CGGCGGTGCACAATCTTCTCGCGC
AACGCGTCAGTGGGCTGATCATTAACTATCCGCTGGATGACCAGGATGCCATTGCTG
TGGAAGCTGCCTGCACTAAGTT
CCGGCGTTATTTCTTGATGTCTCTGACCAGACACCCATCAACAGTATTATTTTCTCCC
ATGAAGACGGTACGCGACTGGG
CGTGGAGCATCTGGTCGCATTGGGTCACCAGCAAATCGCCTGTTAGCGGGCCCATT
AAGTTCTGTCTCGGCGCGTCTGC
GTCTGGCTGGCTGGCATAAATATCTCACTCGCAATCAAATTCAGCCGATAGCGGAAC
GGGAAGGCGACTGGAGTGCCATG
TCCGGTTTTCAACAAACCATGCAAATGCTGAATGAGGGCATCGTTCCCACTGCGATG
CTGGTTGCCAACGATCAGATGGC
GCTGGGCGCAATGCGCGCCATTACCGAGTCCGGGCTGCGCGTTGGTGCGGATATCTC
GGTAGTGGGATACGACGATACCG
AAGACAGCTCATGTTATATCCCGCCGTTAACCACCATCAAACAGGATTTTCGCCTGCT
GGGGCAAACCAGCGTGGACCGC
TTGCTGCAACTCTCTCAGGGCCAGGCGGTGAAGGGCAATCAGCTGTTGCCCGTCTCA
CTGGTGAAAAGAAAAACCACCCT
GGCGCCCAATACGCAAACCGCCTCTCCCCGCGCGTTGGCCGATTCATTAATGCAGCT
GGCACGACAGGTTTCCCGACTGG
AAAGCGGGCAGTGAGCGCAACGCAATTAATGTGAGTTAGCGCGAATTGATCTG

RECOMBINANT BACTERIAL CELLS FOR DELIVERY OF PNP TO TUMOR CELLS

CROSS-REFERENCE TO RELATED APPLICATION

This application is a continuation-in-part of U.S. Ser. No. 08/881,772, filed Jun. 24, 1997, now U.S. Pat. No. 6,017, 896, and Ser. No. 08/702,181, filed Aug. 23, 1996, now abandoned which is a continuation-in-part of U.S. Ser. No. 08/122,321, filed Sep. 14, 1993 now U.S. Pat. No. 5,552, 311. This application also claims priority to provisional application U.S. Ser. No. 60/064,676, filed Oct. 31, 1997.

GRANT REFERENCE

The research carried out in connection with this invention was supported in part by a grant from the National Cancer Institute (CA 7763-02).

BACKGROUND OF THE INVENTION

1. Field of the Invention

This invention is in the field of cancer therapy and in particular, relates to compositions and methods to specifically kill tumor cells by the production of toxic compounds in the tumor cells.

2. Description of the Related Art

Inefficiency of gene delivery, together with inadequate bystander killing, represent two major conceptual hurdles in the development of a toxin mediated gene therapy for human malignancy. Gene transfer is a useful adjunct in the development of new therapies for human malignancy. Tumor cell expression of histocompatibility antigens, cytokines, or growth factors (for example, IL-2, IL-4, GMCSF) appears to enhance immune-mediated clearance of malignant cells in animal models, and expression of chemo-protectant gene products, such as p-glycoprotein in autologous bone marrow cells, is under study as a means of minimizing marrow toxicity following administration of otherwise lethal doses of chemotherapeutic agents.

Theoretically, the most direct mechanism for tumor cell killing using gene transfer is the selective expression of cytotoxic gene products within tumor cells. However, no recombinant enzyme or toxin has proven useful in mediating high levels of toxicity in unselected tumor cells. Classical enzymatic toxins such as pseudomonas exotoxin A, diphtheria toxin and ricin are unlikely to be useful in this context, since these enzymes kill only cells in which they are expressed, and no currently available gene transfer vector is capable of gene delivery to a sufficiently high percentage of tumor cells to make use of the above recombinant enzymes.

Another strategy that has been developed to selectively kill tumor cells involves the delivery and expression of the HSV dThd kinase gene to replicating tumor cells followed by treatment with ganciclovir. Ganciclovir is readily phosphorylated by the HSV dThd kinase, and its phosphorylated metabolites are toxic to the cell. Very little phosphorylation of ganciclovir occurs in normal human cells. Although only those cells expressing the HSV dThd kinase should be sensitive to ganciclovir (since its phosphorylated metabolites do not readily cross cell membranes), in vitro and in vivo experiments have shown that a greater number of tumor cells are killed by ganciclovir treatment than would be expected based on the percentage of cells containing the HSV dThd kinase gene. This unexpected result has been termed the "bystander effect" or "metabolic cooperation." It is thought that the phosphorylated metabolites of ganciclovir may be passed from one cell to another through gap junctions. However, even if a nucleoside monophosphate such as ganciclovir monophosphate were released into the medium by cell lysis, the metabolite would not be able to enter neighboring cells and would likely be degraded (inactivated) to the nucleoside by phosphatases.

Although the bystander effect has been observed in initial experiments using HSV dThd kinase, the limitations of current gene delivery vehicles mean that a much greater bystander effect is important to successfully treat human tumors using this approach. One difficulty with the current bystander toxicity models is that bystander toxicity with metabolites that do not readily cross the cell membrane will not be sufficient to overcome a low efficiency of gene transfer (for example, transfection, transduction, etc.).

One protocol for treating brain tumors in humans uses retroviral delivery of HSV dThd kinase, followed by ganciclovir administration. In rat models, using HSV dThd in this context, tumor regressions have been observed. The HSV dthd kinase approach has not proven sufficient in humans thus far; this may in part be due to (1) inadequate bystander toxicity with HSV dThd kinase, and (2) cell killing only of dividing cells using HSV dThd kinase with ganciclovir. The usefulness of *E. coli* cytosine deaminase, which converts 5-fluorocytosine to 5-fluorouracil, has recently been reported to provide substantial bystander toxicity. However, 5-FU is not a highly toxic compound in this setting and bystander killing in vitro has been inefficient, i.e., similar to that of observed with HSV dThd kinase.

Prodrug activation by an otherwise non-toxic enzyme (for example, HSV dThd kinase, cytosine deaminase) has advantages over the expression of directly toxic genes, such as ricin, diphtheria toxin, or pseudomonas exotoxin. These advantages include the capability to (1) titrate cell killing, (2) optimize therapeutic index by adjusting either levels of prodrug or of recombinant enzyme expression, and (3) interrupt toxicity by omitting administration of the prodrug. However, like other recombinant toxic genes, gene transfer of HSV dThd kinase followed by treatment with ganciclovir is neither designed to kill bystander cells nor likely to have broad bystander toxicity in vivo.

An additional problem with the use of the HSV dThd kinase or cytosine deaminase to create toxic metabolites in tumor cells is the fact that the agents activated by HSV dThd kinase (ganciclovir, etc.) and cytosine deaminase (5-fluorocytosine) kill only cells synthesizing DNA. Even if a considerable number of nontransfected cells are killed, one would not expect to kill the nondividing tumor cells with these agents.

Thus, there exists a need for a toxin gene therapy method that overcomes the problems of inefficient gene delivery, cell replication-dependent killing and low toxin diffusion between cells. The present invention fulfills this longstanding need and desire in the art.

SUMMARY OF THE INVENTION

Accordingly to the present invention, a unique *E. coli* containing the PNP gene (SEQ ID No:5) (see FIGS. 15A–C) is disclosed. This *E. coli* can be used to treat tumors in combination with a prodrug including MeP-dR. Also, a method for causing tumor regression and/or inhibiting tumor growth is disclosed which includes directly administering a purine analog to a tumor.

In yet still another embodiment of the present invention, there is provided a host cell transfected with the vector of the present invention which expresses a purine nucleoside phosphorylase protein.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 5 shows the effect of MeP-dR on transduced cells with stable E. coli PNP expression.

FIG. 8 shows that MeP-dR did not affect parental D54 tumor cell growth. FIG. 9 shows that MeP-dR caused regression of D54 tumors expressing E. coli PNP. Note that in this figure tumors that completely regressed are not included in the calculation of medium tumor weight. Therefore, since 4 animals had no tumors at the end of the experiment, the tumor weight on the days beyond day 40 refer to the two tumors that did not completely regress. In this experiment the two remaining tumors were at the limit of detection and did not show any signs of growth past day 30. Therefore, these animals may also be cured of their disease.

FIG. 10 shows that MeP-dR at two doses did not affect parental D54 tumor cell growth. FIG. 11 shows that MeP-dR at both doses caused regression of D54 tumors expressing E. coli PNP. Note that as in FIG. 9, tumors that completely regressed are not included in the calculation of medium tumor weight. Therefore, since 4 animals, which were treated with 67 mg/kg MeP-dR, had no tumor at the end of the experiment, the tumor weight on the days beyond day 40 refer to the six tumors that did not completely regress.

FIGS. 15A–C is the DNA sequence of E. coli PNP (SEQ ID No:5) inserted in pTRCPNP.

DETAILED DESCRIPTION OF THE INVENTION

Figure 1:
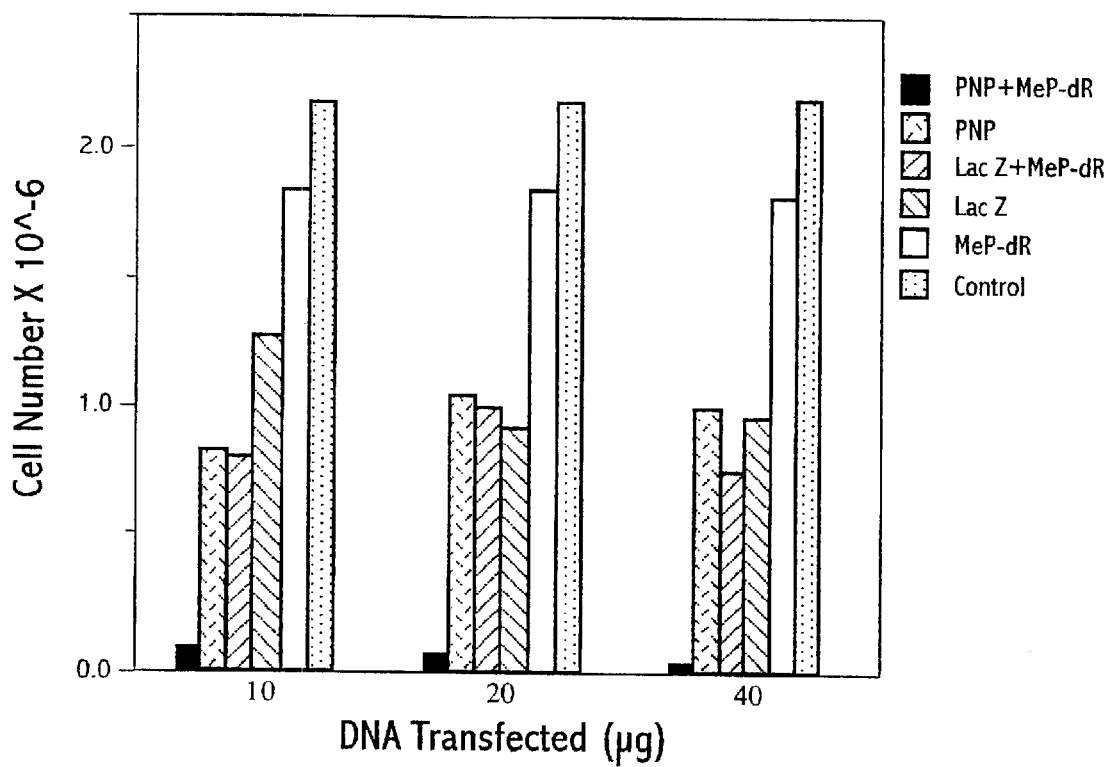
FIG. 1 shows the toxicity due to DOTMA-DOPE liposomes used to transfect T-84 colon carcinoma cells with 10, 20 or 40 $\mu$g of cDNA containing either the E. coli PNP or LacZ genes under the transcriptional control of SV-40 early promoter (SV-PNP and SV-LacZ, respectively) and the additional toxicity when MeP-dR (160 $\mu$M) is added to T-84 transfected cells expressing the PNP gene (PNP+MeP-dR). Cells transfected with SV-PNP construct were treated with (PNP+MeP-dR) and without (PNP) MeP-dR. LacZ transfected cells were studied in the same way. Nontransfected cells were treated with (MeP-dR) and without (control) MeP-dR.
Figure 2A:
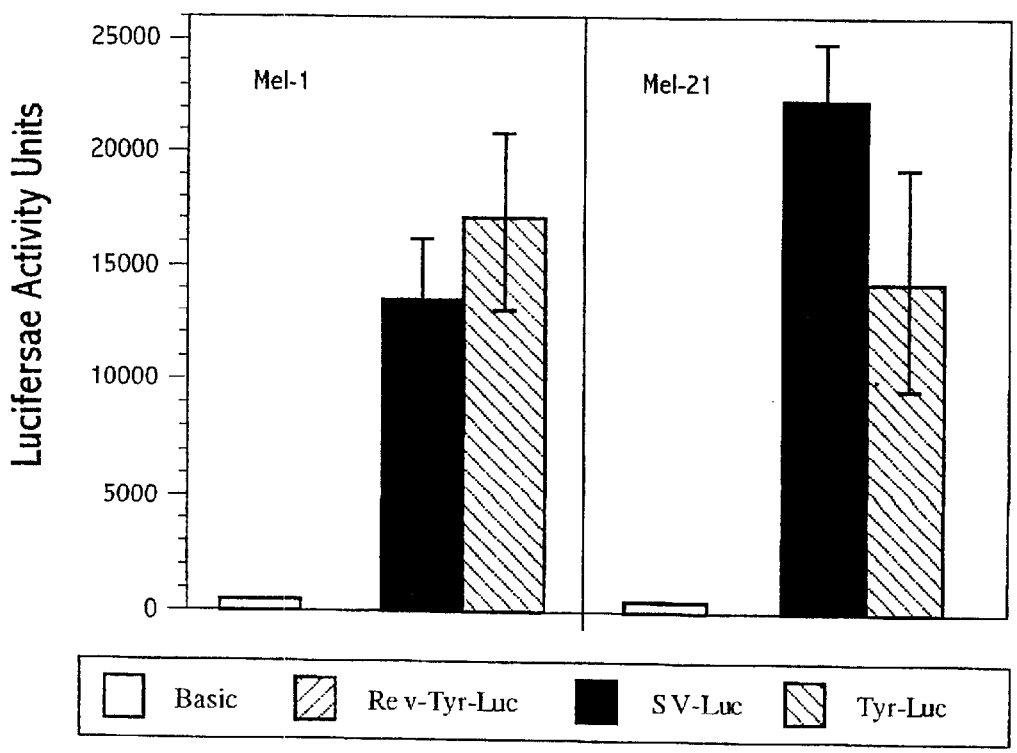
FIGS. 2A–D show the human tyrosinase transcriptional promoter sequence (Tyr)-restricted expression of the luciferase reporter gene (Luc), to which it was operable linked (Tyr-Luc), in melanoma cells Mel-1 and Mel-21 (FIG. 2A), and the SV40 early promoter (SV) constitutive expression of the Luciferase gene (Luc) to which it was operable linked (SV-Luc), in each carcinoma cell line (see FIGS. 2A–2D). Rev-Tyr-Luc, Tyr promoter sequence linked to the Luc gene in reverse orientation so that it does not transcribe Luc (no expression). Basic, promoterless Luc gene construct.
Figure 2B:
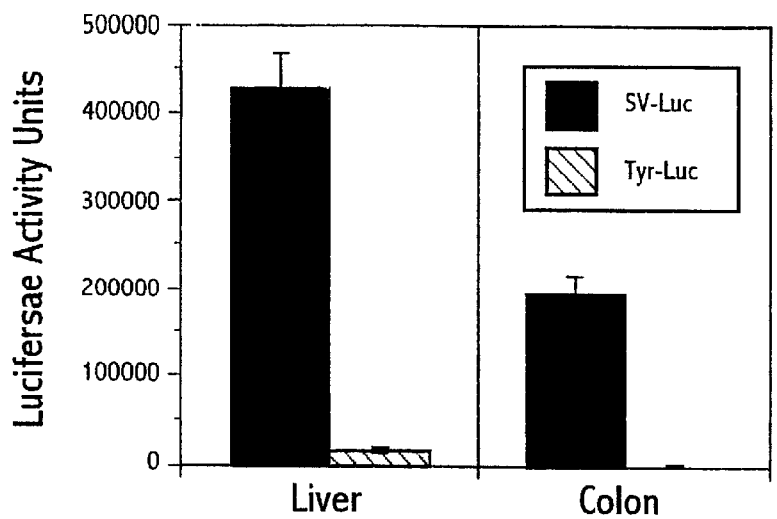
Figure 2C:
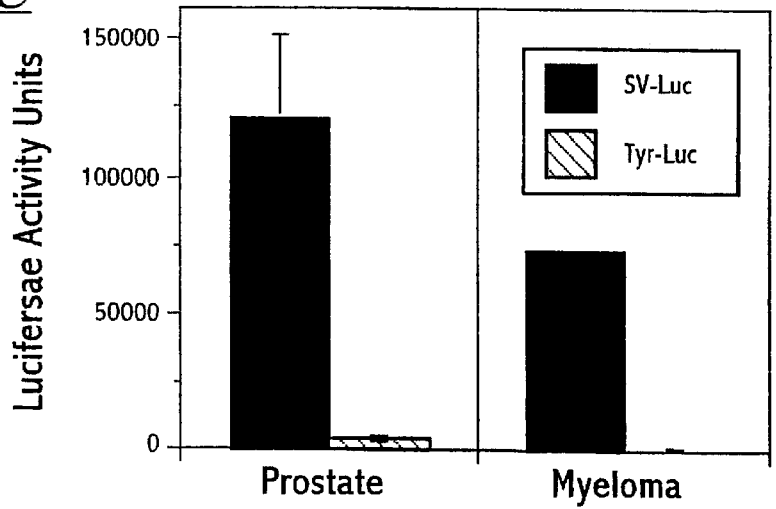
Figure 2D:
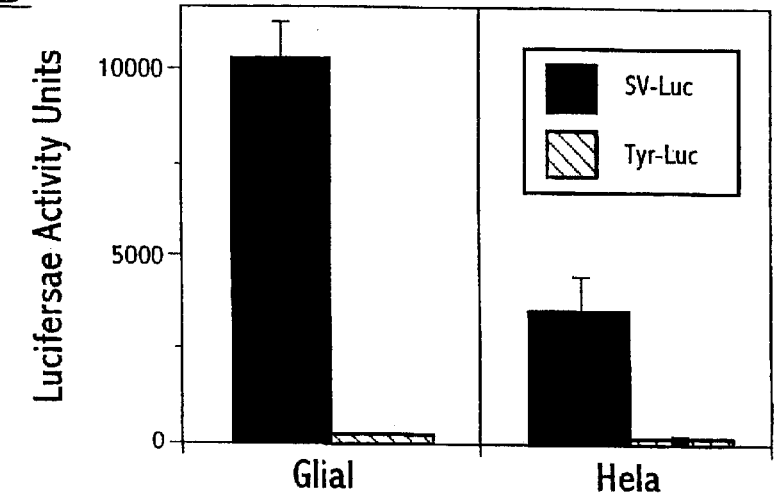

The invention provides a method of killing replicating or non-replicating, transfected or transduced mammalian cells and bystander cells, comprising the following steps: (a)

transfecting or transducing targeted mammalian cells with a nucleic acid encoding a suitable purine nucleoside cleavage enzyme which releases a purine analog from the substrate purine nucleoside or providing such enzyme directly to the targeted cells; and (b) contacting the targeted cells expressing or provided with the purine nucleoside cleavage enzyme with a substrate for the enzyme to produce a toxic purine base thereby killing the targeted cells and also bystander cells not expressing or containing the cleavage enzyme. Thus, in the presence of substrate, the cleavage enzyme produces a toxic product. It should be appreciated that a "non-human or modified human purine analog nucleoside phosphorylase (PNP)" includes the use of either types of PNP in the same therapeutic regimen as the purine nucleoside cleavage enzyme. The killing can occur in vitro or in vivo.

In this method of the present invention, the targeted cells are preferably selected from the group consisting of tumor cells and virally infected cells. In one suitable instance, the natural or modified enzyme is a non-human PNP or hydrolase. More preferably, the hydrolase is a nucleoside hydrolase. Alternatively, the enzyme is a modified mammalian PNP or hydrolase. PNP includes subgroups such as the MTAP (methylthioadenosine phosphorylase).

In one embodiment of this method of the present invention, the enzyme is provided by targeting the enzyme to the cells. More preferably, the enzyme is targeted to the cells by conjugating the enzyme to an antibody.

The enzyme may be encoded by a gene provided to the cells. For example, the gene provided to the cells encodes E. coli PNP and is operably linked to a tyrosinase gene promoter. Alternatively, the gene is provided in a carrier molecule such as polymeric films, gels, microparticles and liposomes.

In another embodiment, the present invention provides a method of killing replicating or non-replicating, targeted mammalian cells and bystander cells, comprising the following steps: (a) delivering a purine nucleoside phosphorylase to the targeted mammalian cells; and (b) contacting the targeted cells with an effective amount of a nucleoside substrate for the purine nucleoside phosphorylase, wherein the substrate is non-toxic to mammalian cells and is cleaved by the phosphorylase to yield a purine base which is toxic to the targeted mammalian cells and bystander cells, to kill the mammalian cells expressing the phosphorylase and the bystander cells. Representative examples of purine analog substrates include 9-(β-D-2-deoxyerythropentofuranosyl)-6-methypurine, 2-amino-6-chloro-1-deazapurine riboside, 7-ribosyl-3-deazaguanine, arabinofuranosyl-2-fluoroadenine, 2-fluoro-2'-deoxyadenosine, 2-fluoro-5'-deoxyadenosine, 2-chloro-2'-deoxyadenosine, 5'-amino-5'-deoxy-adenosine, α-adenosine, MeP-2',3'-dideoxyriboside, 2-F-2',3'-dideoxyadenosine, MeP-3'-deoxyriboside, 2-F-3'-deoxyadenosine, 2-F-adenine-6'-deoxy-β-D-allofuranoside, 2-F-adenine-α-L-lyxofuranoside, MeP-6'-deoxy-β-D-allofuranoside, MeP-α-L-lyxofuranoside, 2-F-adenine-6'-deoxy-α-L-talofuranoside, MeP-6'-deoxy-α-L-talofuranoside.

The present invention also provides a composition for killing targeted mammalian cells, comprising: (a) an enzyme that cleaves a purine substrate; and (b) an effective amount of the purine analog substrate to kill the targeted cells when cleaved by the enzyme.

The present invention is also directed to a vector comprising a DNA sequence coding for a purine nucleoside phosphorylase protein and said vector is capable of replication in a host which comprises, in operable linkage: a) an origin of replication; b) a promoter; and c) a DNA sequence coding for said protein. Preferably, the vector is selected from the group consisting of a retroviral vector, an adenoviral vector, an adeno-associated viral vector, a herpes vector, a viral vector and a plasmid.

The present invention also includes a method for inhibiting tumor growth by directly administering to a tumor a purine analog or derivative thereof.

The present invention is also directed to a host cell transfected with the vector of the present invention so that the vector expresses an E. coli purine nucleoside phosphorylase protein. Preferably, such host cells are selected from the group consisting of bacterial cells, mammalian cells and insect cells.

Some of the methods and compositions, exemplified below, involve transfecting cells with the E. coli DeoD gene (encoding a purine analog nucleoside phosphorylase (PNP)) and subsequently treating with a nontoxic purine nucleoside, e.g., deoxyadenosine or deoxyguanosine analogs, including N7 analogs), which is converted to a toxic purine analog. E. coli PNP differs from human PNP in its more efficient acceptance of adenine and certain guanine-containing nucleoside analogs as substrates. E. coli PNP expressed in tumor cells cleaves the nucleoside, liberating a toxic purine analog. Purine analogs freely diffuse across cell membranes, whereas nucleoside monophosphates such as those generated using HSV Thd kinase, generally remain inside the cell in which they are formed. A toxic adenine analog formed after conversion by E. coli PNP can be converted by adenine phosphoribosyl transferase to toxic nucleotides and kill all transfected cells, and diffuse out of the cell and kill surrounding cells that were not transfected (bystander cells).

Enzymes Catalyzing Purine Analog Conversion

Two classes of enzymes can be used: phosphorylases and nucleosidase hydrolases. A PNP useful in the methods and compositions described herein catalyzes the conversion of purine analog nucleosides plus inorganic phosphate to free the toxic purine analog plus ribose-1-phosphate (or deoxyribose-1-phosphate): purine analog nucleoside+ $PO_4 \leftrightarrows$ purine analog ribose-1-$PO_4$ (or deoxyribose-1-phosphate)+toxic purine analog. Methylthioadenosine phosphorylase, a subclass of PNP, would also be useful in this context. Non-mammalian and modified human or modified other mammalian PNPs can be used. The non-mammalian PNP can be an E. coli purine analog nucleoside phosphorylase. However, any PNP which can selectively convert a substrate to produce a toxic purine analog can be utilized. Thus, modifications in the E. coli PNP, which retain this activity, are within the scope of the class of enzymes suitable for the described methods and compositions, as are human PNP enzyme molecules that have been modified to cleave purine analog nucleoside to release the toxic purine analog moiety. A method is presented below by which any proposed PNP or other purine analog nucleoside cleavage enzyme can be tested in a cell for its ability to convert a given substrate from a relatively nontoxic form to a toxin for the cells.

Table I lists organisms which possess an enzyme that cleaves adenine-containing nucleosides to adenine and so are useful in the methods described herein. Table I also shows that humans and the malaria parasite *Plasinodium falciparum* do not possess an enzyme useful in the described methods. Thus, to be useful in the methods described herein, a human or *P. falciparum* PNP would have to be modified to be capable of cleaving a purine analog nucleoside substrate to liberate this toxic purine analog. Such modifications can be made at the genetic level or protein level. For example, in vitro mutagenesis of the gene encoding the human or *P. falciparum* PNP can be used to alter the gene sequence to encode a PNP that will cleave a particular purine analog nucleoside.

As described above, in a preferred embodiment, the PNP used in the present methods can include genetically modified mammalian or non-mammalian PNP, as well as bacterial PNP, capable of reacting with a substrate that the native PNP in the tumor cell will not recognize or recognizes poorly. Thus, the nucleic acids that encode a useful PNP are present in cells in which they are not naturally found, either because they are from a different organism or because they have been modified from their natural state. The key requirement of the nucleic acids encoding the PNP or other purine analog nucleoside cleavage enzyme is that they must encode a functional enzyme that is able to recognize and act upon a substrate that is not well recognized by the native PNP of the cell.

Nucleosidases or nucleoside hydrolases are another class of enzymes suitable for the methods and compositions described herein. The definition of a purine analog nucleosidase is an enzyme that catalyzes the conversion of purine analog nucleosides plus water to liberate free toxic purine analogs plus ribose (or deoxyribose): purine analog nucleoside+$H_2O \leftrightarrows$ purine analog+ribose (or deoxyribose).

Transcriptional Regulation of the PNP Encoding Sequence

Since a bacterial PNP is encoded on a prokaryotic gene, the expression of the bacterial PNP in mammalian cells will require a eukaryotic transcriptional regulatory sequence linked to the PNP-encoding sequences. The bacterial PNP gene can be expressed under the control of strong constitutive promoter/enhancer elements that are obtained within commercial plasmids (for example, the SV40 early promoter/enhancer (pSVK30 Pharmacia, Piscataway, N.J., cat. no. 27-4511-01), moloney murine sarcoma virus long terminal repeat (pBPV, Pharmacia, cat. no. 4724390-01), mouse mammary tumor virus long terminal repeat (pMSG, Pharmacia, cat. no. 27-4506-01), and the cytomegalovirus early promoter/enhancer (pCMVβ, Clontech, Palo Alto, Calif., cat. no. 6177-1)).

Selected populations of cells can also be targeted for destruction by using genetic transcription regulatory sequences that restrict expression of the bacterial PNP (or other suitable purine analog nucleoside cleavage enzyme) coding sequence to certain cell types, a strategy that is referred to as "transcription targeting." A candidate regulatory sequence for transcription targeting must fulfill two important criteria as established by experimentation: (i) the regulatory sequence must direct enough gene expression to result in the production of enzyme in therapeutic amounts in targeted cells, and (ii) the regulatory sequence must not direct the production of sufficient amounts of enzyme in non-targeted cells to impair the therapeutic approach. In this form of targeting, the regulatory sequences are functionally linked with the PNP sequences to produce a gene that will only be activated in those cells that express the gene from which the regulatory sequences were derived. Regulatory sequences that have been shown to fulfill the criteria for transcription targeting in gene therapy include regulatory sequences from the secretory leucoprotease inhibitor, surfactant protein A, and α-fetoprotein genes. A variation on this strategy is to utilize regulatory sequences that confer "inducibility" so that local administration of the inducer leads to local gene expression. As one example of this strategy, radiation-induced sequences have been described and advocated for gene therapy applications. It is expected that bacterial PNP gene expression could be targeted to specific sites by other inducible regulatory elements.

Figure 3A:
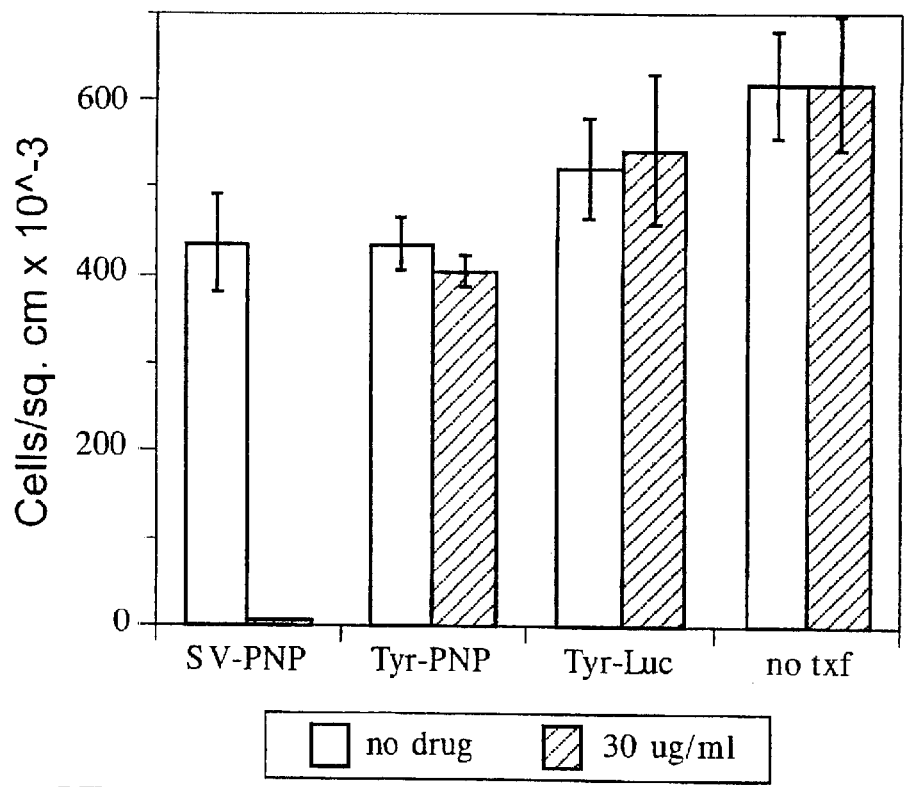
FIGS. 3A and 3B show the dependence of purine analog nucleoside MeP-dR toxicity on expression of E. coli purine analog nucleoside phosphorylase (PNP). SV-PNP, cells transfected with a construct in which the constitutive SV40 early promoter is operably linked to the PNP gene; Tyr-PNP, cells transfected with a construct in which the melanoma specific human tyrosinase promoter sequence is operably linked to PNP gene; Tyr-Luc, cells transfected with a construct in which the melanoma specific human tyrosinase promoter sequence is operably linked to luciferase reporter gene; no-txf, cells not transfected with a recombinant construct. T-84, carcinoma cell line (3A); Mel-1, melanoma cell line (3B).
Figure 3B:
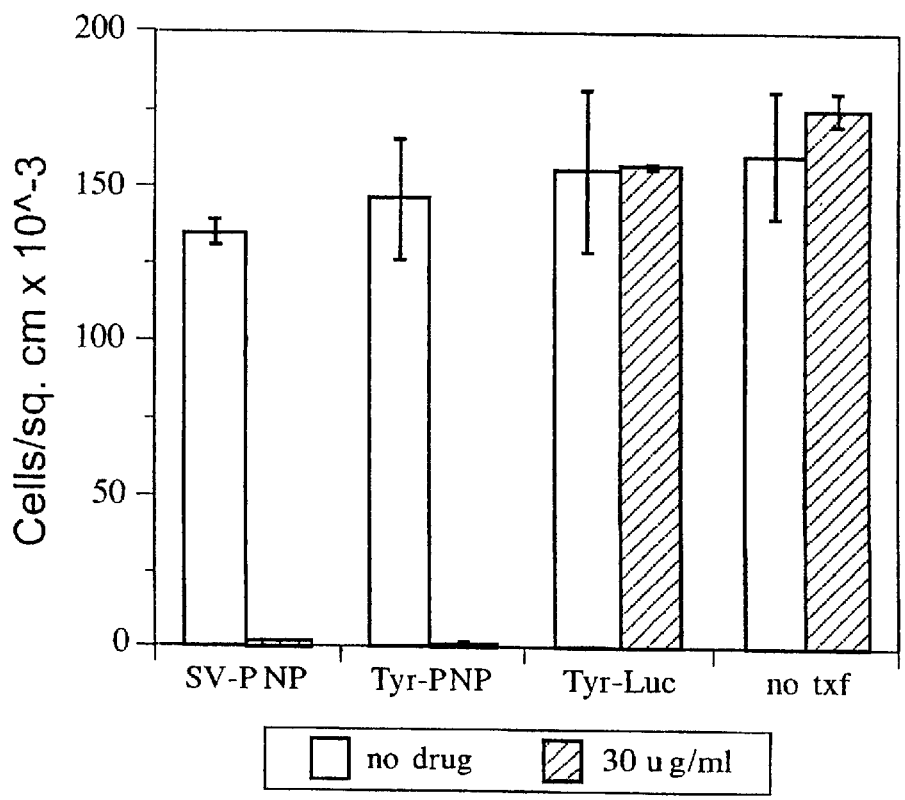

It may be necessary to utilize tissue-specific enhancer/promoters as a means of directing PNP expression, and thereby PNP-mediated toxicity, to specific tissues. For example, human tyrosinase genetic regulatory sequences are sufficient to direct PNP toxicity to malignant melanoma cells. Mouse tyrosinase sequences from the 5' flanking region (−769 bp from the transcriptional start site) of the gene were capable of directing reporter gene expression to malignant melanoma cells. Although the mouse and human tyrosinase sequences in the 5' flanking region are similar, Shibata et al., *Journal of Biological Chemistry*, 267:20584–20588 (1992) have shown that the human 5' flanking sequences in the same region used by Vile and Hart (−616 bp from the transcriptional start site) did not confer tissue specific expression. Although Shibata et al. suggested that the 5' flanking region would not be useful to target gene expression to tyrosinase expressing cells (melanomas or melanocytes), a slightly different upstream fragment from that used by Shibata et al., can in fact direct reporter or bacterial PNP gene expression specifically to melanoma cells, as shown in FIG. 3.

The 5' flanking region of the human tyrosinase gene was amplified by the polymerase chain reaction from human genomic DNA. The primers were designed to amplify a 529 bp fragment that extended −451 to +78 bp relative to the transcription start site by using a published sequence of the human tyrosinase gene and flanks (Kikuchi, et al., *Biochimica et Biophysica Acta*, 1009:283–286 (1989)). The fragment was shown by reporter gene assays to be able to direct reporter gene expression in melanoma cells (FIG. 2). The same tyrosinase fragment was used to direct PNP expression within a plasmid vector and shown to result in PNP mediated toxicity only in melanoma cells (FIG. 3). Therefore, human tyrosinase sequences are useful to direct PNP expression to human melanoma cells. These same sequences could be useful to direct other therapeutic gene expression in melanoma cells or melanocytes. Other tissue-specific genetic regulatory sequences and elements can be used to direct expression of a gene encoding a suitable purine analog nucleoside cleavage enzyme to specific cell types other than melanomas.

TABLE I

| Organism | Enzyme |
| --- | --- |
| Organisms which can cleave adenine-containing nucleosides to adenine | |
| *Leishmania donvani* | Hydrolase |
| *Trichomomas vaginalis* | Phosphorylase |
| *Trypanosoma cruzi* | Hydrolase |
| *Schistosoma mansoni* | Phosphorylase |
| *Leishmania tropica* | Hydrolase |
| *Crithidia Fasciculata* | Hydrolase |
| Aspergilis and Penicillium | Hydrolase |
| *Erwinia carotovora* | Phosphorylase |
| *Helix pomatia* | Phosphorylase |
| *Ophiodon elongatus* (lingcod) | Phosphorylase |
| *E. coli* | Phosphorylase |
| *Salmonella typhimurium* | Phosphorylase |
| *Bacillus subtilis* | Phosphorylase |
| Clostridium | Phosphorylase |
| mycoplasma | Phosphorylase |
| *Trypanosoma gambiense* | Hydrolase |
| *Trypanosoma brucei* | Phosphorylase (methylthio adenosine phosphorylase) |

TABLE I-continued

| Organism | Enzyme |
| --- | --- |
| Organisms which cannot (or poorly) convert adenine-containing nucleosides to adenine | |
| Human | Phosphorylase |
| P. falciparum | Phosphorylase |

Substrate Selection

A purine analog nucleoside which is a substrate for the enzyme to produce a toxic substance which kills the cells is referred to herein as a "prodrug." Any deoxypurine analog nucleoside composed of the cytotoxic purine bases including those listed below and in Table II should be a substrate for the E. coli PNP or other equivalent purine analog nucleoside cleavage enzyme. A requisite is that the analog must have a low toxicity at the nucleoside level (that is, as a prodrug). Using ribose- or deoxyribose-containing substrates, E. coli PNP can selectively produce a variety of toxic guanine analogs, such as 6-thioguanine or 3-deazaguanine, that are attached to ribose or deoxyribose via the N-7 position in the guanine ring. The strategy described here for therapeutic PNP gene transfer implicates new uses for several broad classes of specifically activatable cytotoxic purine analogs in the treatment of human malignancy. Because the growth fraction is very small in most tumors, it is sometimes preferable to select compounds that are active against both dividing and nondividing cells. Some of the toxic purine analogs produced using E. coli PNP in the present method are toxic to nondividing as well as dividing cells. Specific examples of suitable purine analog nucleosides that will work in the compositions and methods described herein can be tested according to the protocols set forth in the Examples.

In a preferred embodiment described in the Examples, the substrate is 9-($\beta$-D-2-deoxyerythropentofuranosyl)-6-methylpurine (MeP-dR). Although MeP-dR is relatively non-toxic, the therapeutic index of this compound can be enhanced. For instance, if the toxicity of MeP-dR is due to phosphorylation by a deoxynucleoside kinase, then analogs that cannot be phosphorylated, such as 5'-deoxy-MeP-dR, can be synthesized and used as the prodrug to generate MeP in vivo.

The compounds 6-methylpurine-2'-deoxyriboside (*Gene Therapy*, 1:233–238, 1994), 2-amino-6-chloro-1-deazapurine riboside (*Biochem. Pharmacol.*, 33:261–271, 1984), and 7-ribosyl-3-deazaguanine (*Biochem. Pharmacol.*,29:1791–1787, 1979) are examples of prodrugs that are useful substrates for the E. coli PNP. They are much less toxic than their respective purine analogs.

Delivery of the PNP Gene

Described below is the construction of suitable recombinant viruses and the use of adenovirus for the transfer of bacterial PNP into mammalian cells. Non-viral gene delivery can also be used. Examples include diffusion of DNA in the absence of any carriers or stabilizers ("naked DNA"), DNA in the presence of pharmacologic stabilizers or carriers ("formulated DNA"), DNA complexed to proteins that facilitate entry into the cell ("Molecular conjugates"), or DNA complexed to lipids. The use of lipid-mediated delivery of the bacterial PNP gene to mammalian cells is exemplified below. More particularly, cationic liposome-mediated transfer of a plasmid containing a non-human PNP gene is demonstrated. However, other gene transfer methods will also generally be applicable because the particular method for transferring the PNP gene to a cell is not solely determinative of successful tumor cell killing. Thus, gene transduction, utilizing a virus-derived transfer vector, further described below, can also be used. Such methods are well known and readily adaptable for use in the gene-mediated toxin therapies described herein. Further, these methods can be used to target certain diseases and cell populations by using the targeting characteristics of a particular carrier of the gene encoding a suitable purine analog nucleoside cleavage enzyme such as E. coli PNP.

Figure 12:
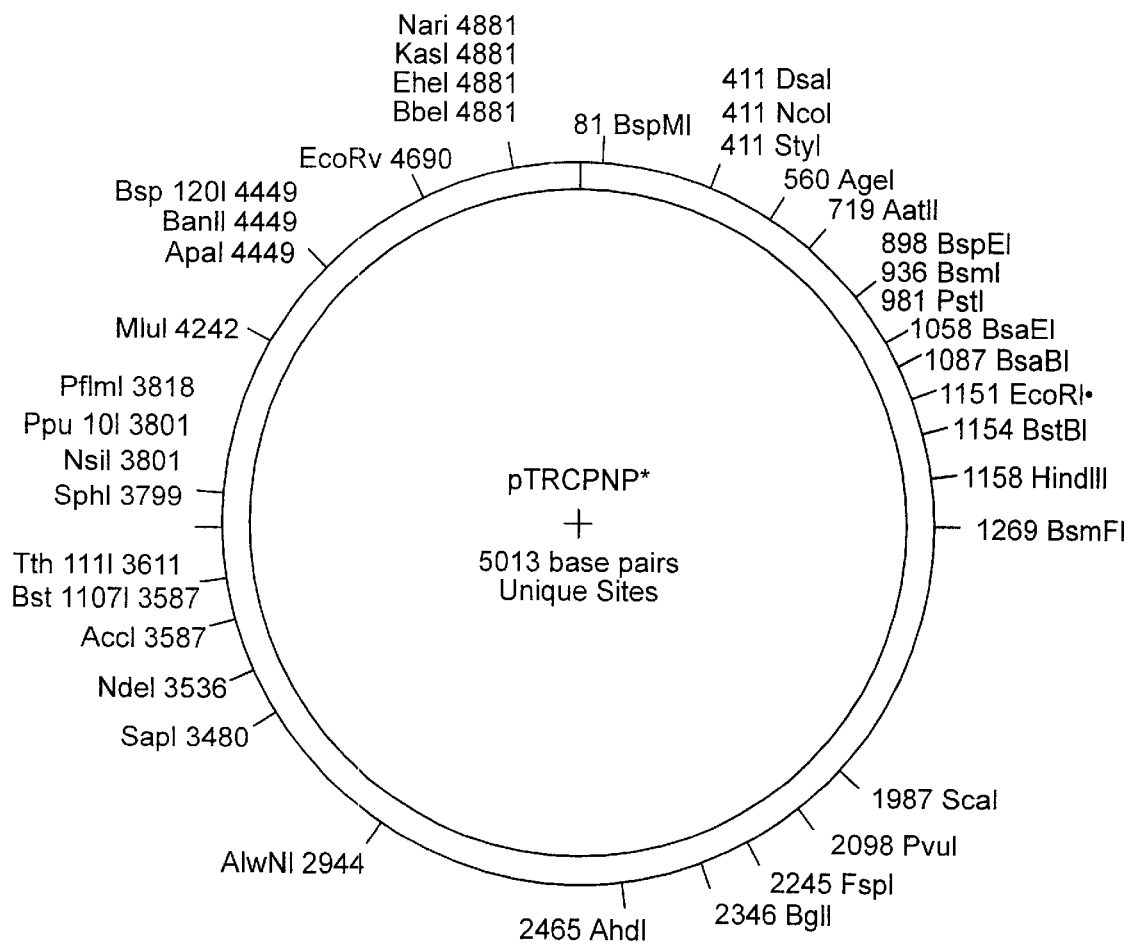
FIG. 12 is a predicted restriction map of plasmid pTRCPNP containing the predicted 5013 base sequence pairs (SEQ ID No:5) encoding E. coli PNP.

Apathogenic anaerobic bacteria have been used to selectively deliver foreign genes into tumor cells. For example, *Clostridium acetobutylicum* spores injected intravenously into mice bearing tumors, germinated only in the necrotic areas of tumors that had low oxygen tension. Using the standard PNP assay described below, *Clostridium perfringens* (Sigma Chemical Co., St. Louis, Mo.) was found to exhibit enzyme activity capable of converting MeP-dR to MeP. This finding suggests a mechanism to selectively express bacterial PNP activity in tumor masses with necrotic, anaerobic centers. Thus, tumors can be infected with such strains of Clostridium and then exposed to a purine analog such as MeP-dR. The PNP activity of the clostridium bacteria growing in the anaerobic center of the tumor tissue should then convert the MeP-dR to MeP, which then is released locally to kill the tumor cells. Additionally, other bacteria including E. coli and Salmonella can be used to deliver the PNP gene or hydrolase into tumors. As described and demonstrated below in Example 25, E. coli containing a plasmid (see FIG. 12) encoding the E. coli PNP gene plus MeP-dR demonstrated efficacious anti-tumor activity (slowing of tumor growth) in mice and also that delivery of significant amounts of E. coli PNP to tumor cells in animals could activate MeP-dR resulting in anti-tumor response.

The rapidly advancing field of therapeutic DNA delivery and DNA targeting also includes vehicles such as "stealth" and other antibody-conjugated liposomes (including lipid-mediated drug targeting to colonic carcinoma), receptor-mediated targeting of DNA through cell specific ligands, lymphocyte-directed tumor targeting, and highly specific therapeutic retroviral targeting of murine glioma cells in vivo (S. K. Huang et al., *Cancer Research*, 52:6774–6781 (1992); R. J. Debs et al.,*Am. Rev. Respir. Dis.*, 135:731–737 (1987); K. Maruyama et al., *Proc. Natl. Acad. Sci. USA*, 87:5744–5748 (1990); P. Pinnaduwage and L. Huang, *Biochemistry*, 31:2850–2855 (1992); A. Gabizon and Papahadjopoulas,*Proc. Natl. Acad. Sci. USA*, 85:6949–6953 (1988); S. Rosenberg et al., *New England J. Med.*, 323:570–578 (1990); K. Culver et al., *Proc. Natl. Acad. Sci. USA*, 88:3155–3159 (1991); G. Y. Wu and C. H. Wu,*J. Biol. Chem.*, 263, No. 29:14621–14624 (1988); Wagner et al., *Proc. Natl. Acad. Sci. USA*, 87:3410–3414 (1990); Curiel et al., *Human Gene Ther.*, 3:147–154 (1992); Litzinger, *Biochimica et Biophysica Acta*, 1104:179–187 (1992); Trubetskoy et al., *Biochemica et Biophysica Acta*, 1131:311–313 (1992)). The present approach, within the context of a gene targeting mechanism either directed toward dividing tumor cells or tumor neovascularization, offers an improved means by which a small subset of tumor cells could be established within a growing tumor mass, which would mediate rapid tumor involution and necrosis after the appropriate signal, i.e., after administration of the substrate (prodrug) for a suitable purine analog nucleoside cleavage enzyme, such as E. coli PNP present in or adsorbed to tumor cells.

Methods of Treatment

The method of treatment basically consists of providing to cells the PNP gene and then exposing the cells with the PNP gene or protein to an appropriate substrate which is converted to a toxic substance which kills the cells expressing the PNP gene as well as those in the vicinity of the PNP gene expressing cells. The PNP gene can be administered directly to the targeted cells or systemically in combination with a targeting means, such as through the selection of a particular viral vector or delivery formulation. Cells can be treated in vivo, within the patient to be treated, or treated in vitro, then injected into the patient. Following introduction of the PNP gene into cells in the patient, the prodrug is administered, systemically or locally, in an effective amount to be converted by the PNP into a sufficient amount of toxic substance to kill the targeted cells.

Treatment of Tumors The *E. coli* PNP gene can also be used as part of a strategy to treat metastatic solid tumors, such as melanoma, pancreatic, liver or colonic carcinoma. No effective therapy for metastatic tumors of these types currently exists. In this method, plasmid DNA containing a PNP gene under the control of tumor specific promoters is used. For example, the tyrosinase promoter is highly specific for mediating expression in melanoma cells, and will not lead to gene expression in most tissue types. The PNP gene under the regulatory control of this promoter, therefore, should be activated predominantly within a melanoma tumor and not elsewhere within a patient (see Example 11 and FIGS. 2A–D below). Promoters specific for other tumor types, for example, promoters active in the rapidly dividing endothelial cells present in all solid tumors can be used to specifically activate PNP only within a primary or metastatic tumor. In this method, plasmid DNA containing PNP under the control of a tumor specific promoter is delivered to cells using cationic liposomes. For example, based on animal studies, 100–400 mg plasmid DNA complexed to 1200–3600 micromoles of a 1:1 mixture of the lipids DOTMA (1,2-dioleyloxypropyhl-3-trimethyl ammonium bromide) and DOPE (dioleoyl phosphatidylethanolamine) could be used to deliver the PNP gene to tumor metastases in patients. A prodrug in the above described amounts can then be administered.

The PNP gene can be used to activate prodrugs in the treatment of human brain cancer. In this method, a cell line producing retroviral particles, in which the viral particles contain the *E. coli* PNP gene, is injected into a central nervous system (CNS) tumor within a patient. An MRI scanner is used to appropriately inject the retroviral producer cell line to within the tumor mass. Because the retrovirus is fully active only within dividing cells and most of the dividing cells within the cranium of a cancer patient are within the tumor, the retrovirus is primarily active in the tumor itself, rather than in non-malignant cells within the brain. Clinical features of the patient including tumor size and localization, determine the amount of producer cells to be injected. For example, a volume of producer cells in the range of 30 injections of 100 microliters each (total volume 3 ml with approximately $1 \times 10^8$ producer cells/ml injected) are given under stereotactic guidance for surgically inaccessible tumors. For tumors which can be approached intraoperatively, 100 $\mu$l aliquots are again injected (at about $1 \times 10^8$ cells/ml) with total injected volumes up to 10 ml using *E. coli* PNP gene transfer, followed by MeP-dR administration. This strategy is designed to permit both bystander killing and toxicity to non-dividing cells and is thus designed for much greater tumor involution than previous attempts using HSV dThd kinase and ganciclovir.

The destruction of selected populations of cells can be achieved by targeting the delivery of the bacterial PNP gene or other gene encoding an enzyme capable of cleaving purine analog from a purine analog nucleoside (such as adenine from adenine-containing nucleosides as described above). The natural tropism or physiology of viral vectors can also be exploited as a means of targeting specific cell types. For example, retroviruses are well known to become fully active only in replicating cells. This fact has been used as the basis for selective retroviral-mediated gene transfer to replicating cancer cells growing within a site where the normal (nonmalignant) cells are not replicating in both animal and human clinical studies. Alternatively, the viral vector can be directly administered to a specific site such as a solid tumor, where the vast majority of the gene transfer will occur relative to the surrounding tissues. This concept of selective delivery has been demonstrated in the delivery of genes to tumors in mice by adenovirus vectors. Molecular conjugates can be developed so that the receptor binding ligand will bind only to selective cell types, as has been demonstrated for the lectin-mediated targeting of lung cancer.

Recently, it was shown that intravenous injection of liposomes carrying DNA can mediate targeted expression of genes in certain cell types. Targeting of a gene encoding a purine analog nucleoside cleavage enzyme or expression of the gene to a small fraction of the cells in a tumor mass followed by substrate administration could be adequate to mediate involution. Through the substantial bystander effect and killing of nondividing cells demonstrated in the Examples, the present method can be used to destroy the tumor.

Treatment of Virally Infected Cells

In addition to killing tumor cells, the methods described herein can also be used to kill virally infected cells. In a virus-killing embodiment, the selected gene transfer method is chosen for its ability to target the expression of the cleavage enzyme in virally infected cells. For example, virally infected cells may utilize special viral gene sequences to regulate and permit gene expression, that is, virus specific promoters. Such sequences are not present in uninfected cells. If the PNP gene is oriented appropriately with regard to such a viral promoter, the cleavage enzyme would only be expressed within virally infected cells, and not other, uninfected, cells. In this case, virally infected cells would be much more susceptible to the administration of MeP-dR or other substrates designed to be converted to toxic form by non-human or modified human purine nucleoside cleavage enzyme.

Administration of Genetically Engineered Cells

For certain applications, cells that receive the PNP gene are selected and administered to a patient. This method most commonly involves ex vivo co-transfer of both the gene encoding the cleavage enzyme, such as the bacterial PNP gene, and a second gene encoding a therapeutic protein gene. The cells that receive both genes are reinfused into the host patient where they can produce the therapeutic protein until the prodrug, such as MeP-dR, is administered to eliminate the engineered cells. This method should be useful in "cell therapies", such as those used on non-replicating myoblasts engineered for the production of tyrosine hydroxylase within the brain (Jiao et al., *Nature*, 362:450 (1993)).

Direct Delivery of the PNP Enzyme to Cells

The bystander killing conferred by the bacterial PNP protein plus prodrug combination can also be achieved by delivering the PNP protein to the target cells, rather than the PNP gene. For example, a PNP enzyme capable of cleaving purine analog nucleosides as described above, is manufactured by available recombinant protein techniques using commercially available reagents. As one example of a method for producing the bacterial PNP protein, the *E. coli* PNP coding sequence is ligated into the multiple cloning site of pGEX-4T-1 (Pharmacia, Piscataway N.J.) so as to be "in frame", with the glutathione-s-transferase (GST) fusion protein using standard techniques (note that the cloning site of this vector allows insertion of coding sequences in all three possible translational reading frames to facilitate this step). The resulting plasmid contains the GST-PNP fusion coding sequence under transcriptional control of the IPTG-inducible prokaryotic tac promoter. *E. coli* cells are transformed with the recombinant plasmid and the tac promoter induced with IPTG. IPTG-induced cells are lysed, and the GST-PNP fusion protein purified by affinity chromatography on a glutathione Sepharose 4B column. The GST-PNP fusion protein is eluted, and the GST portion of the molecule removed by thrombin cleavage. All of these techniques and reagents are provided in a commercially available kit (Pharmacia, Piscataway, N.J., catalog no. 27-457001). Other methods for recombinant protein production are described in detail in published laboratory manuals. Since the bacterial PNP activates the prodrugs into diffusible toxins, it is only necessary to deliver the PNP protein to the exterior of the target cells prior to prodrug administration. The PNP protein can be delivered to targets by a wide variety of techniques. One example would be the direct application of the protein with or without a carrier to a target tissue by direct application, as might be done by directly injecting a tumor mass within an accessible site. Another example would be the attachment of the PNP protein to a monoclonal antibody that recognizes an antigen on the tumor site. Methods for attaching functional proteins to monoclonal antibodies have been previously described. The PNP conjugated monoclonal antibody is systemically administered, for example, intravenously (IV), and attaches specifically to the target tissue. Subsequent systemic administration of the prodrug will result in the local production of diffusible toxin in the vicinity of the tumor site. A number of studies have demonstrated the use of this technology to target specific proteins to tumor tissue. Other ligands, in addition to monoclonal antibodies, can be selected for their specificity for a target cell and tested according to the methods taught herein.

Another example of protein delivery to specific targets is that achieved with liposomes. Methods for producing liposomes are described e.g., *Liposomes: A Practical Approach*). Liposomes can be targeted to specific sites by the inclusion of specific ligands or antibodies in their exterior surface, in which specific liver cell populations were targeted by the inclusion of asialofetuin in the liposomal surface (Van Berkel et al., *Targeted Diagnosis and Therapy*, 5:225–249 (1991)). Specific liposomal formulations can also achieve targeted delivery, as best exemplified by the so-called Stealth™ liposomes that preferentially deliver drugs to implanted tumors (Allen, *Liposomes in the Therapy of Infectious Diseases and Cancer*, 405–415 (1989)). After the liposomes have been injected or implanted, unbound liposome is allowed to be cleared from the blood, and the patient is treated with the purine analog nucleoside prodrug, such as MeP-dR, which is cleaved to MeP by the *E. coli* PNP or other suitable cleavage enzyme at the targeted site. Again, this procedure requires only the availability of an appropriate targeting vehicle. In a broader sense, the strategy of targeting can be extended to specific delivery of the prodrug following either PNP protein, or gene delivery.

Administration of Substrates

The formula of Freireich et al., *Cancer Chemother. Rep.*, 50:219–244, (1966) can be used to determine the maximum tolerated dose of substrate for a human subject. For example, based on systemically administered dose response data in mice showing that a dose of 25 mg (Mep-dR) per kg per day for 9 days (9 doses total) resulted in some toxicity but no lethality, a human dosage of 75 mg MeP-dR/m$^2$ was determined according to the formula: 25 mg/kg×3=75 mg/m$^2$. This amount or slightly less should result in maximal effectiveness of tumor cell killing in humans without killing the subject. This standard of effectiveness is accepted in the field of cancer therapy. However, more preferred is a range of from about 10% to 1% of the maximum tolerated dosage (for example, 7.5 mg/m$^2$–0.75 mg/m$^2$). Furthermore, it is understood that modes of administration that permit the substrate to remain localized at or near the site of the tumor will be effective at lower doses than systemically administered substrates.

The substrate may be administered orally, parenterally (for example, intravenously), by intramuscular injection, by intraperitoneal injection, or transdermally. The exact amount of substrate required will vary from subject to subject, depending on the age, weight and general condition of the subject, the severity of the disease that is being treated, the location and size of the tumor, the particular compound used, its mode of administration, and the like. An appropriate amount may be determined by one of ordinary skill in the art using only routine experimentation given the teachings herein. Generally, dosage will preferably be in the range of about 0.5–50 mg/m$^2$, when considering MeP-dR for example, or a functional equivalent.

Depending on the intended mode of administration, the substrate can be in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the selected substrate in combination with a pharmaceutically acceptable carrier and, in addition, may include other medicinal agents, pharmaceutical agents, carriers, or diluents. By "pharmaceutically acceptable" is meant a material that is not biologically or otherwise undesirable, which can be administered to an individual along with the selected substrate without causing significant undesirable biological effects or interacting in a deleterious manner with any of the other components of the pharmaceutical composition in which it is contained.

For solid compositions, conventional nontoxic solid carriers include, for example, pharmaceutical grades of mannitol, lactose, starch, magnesium stearate, sodium saccharine, talc, cellulose, glucose, sucrose and magnesium carbonate. Liquid pharmaceutically administrable compositions can, for example, be prepared by dissolving or dispersing an active compound with optimal pharmaceutical adjuvants in an excipient, such as water, saline, aqueous dextrose, glycerol, or ethanol, to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see *Remington's Pharmaceutical Sciences*.

For oral administration, fine powders or granules may contain diluting, dispersing, and/or surface active agents, and may be presented in water or in a syrup, in capsules or sachets in the dry state or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration is generally by injection. Injectables can be prepared in conventional forms, either liquid solutions or suspensions, solid forms suitable for solution or prior to injection, or as suspension in liquid prior to injection or as emulsions.

Cells Expressing *E. coli* PNP Substrate

The effect of MeP-dR on human colon carcinoma cells expressing *E. coli* PNP substrate was demonstrated. MeP-dR was chosen because it is 20-fold less toxic than 6-methylpurine (MeP) to HEp-2 cells and it has been used to detect cultures infected with mycoplasma, because mycoplasma express an enzyme similar in function to *E. coli* PNP.

The following examples are given for the purpose of illustrating various embodiments of the invention and are not meant to limit the present invention in any fashion.

EXAMPLE 1
Cell Lines

T-84 colon carcinoma cells were grown in Dulbecco's modified Eagle medium containing F12 nutrient medium (DMEM/F12) (GIBCO/BRL, Gaithersburg, Md.) in 6 well trays to a density of approximately $1-2\times10^3$ cells/well (~20% confluency).

EXAMPLE 2
Toxicity of MeP and MeP-dR within Colon Carcinoma Cells

Untransfected T-84 colon carcinoma cells were treated with increasing concentrations of either MeP-dR or MeP. After 5 days the cells were removed from each well and the number of dye excluding cells were determined with the aid of a hemacytometer. Cells were studied both at passage 48 (p. 48) and passage 61 (p. 61). MeP was obtained from Sigma Chemical Company (St. Louis, Mo.). MeP-dR was synthesized by standard methods as described (J. A. Montgomery and K. Howson, *J. Med. Chem.*, 11:48–52 (1968)). The nucleoside and base were dissolved in serum free DMEM/F12 at a concentration of 1 mg/ml and added directly to 1 ml DMEM/F12 with 10% fetal bovine serum at the concentrations described below in order to cover $1-2\times 10^5$ cells/well.

Initial cytopathic effects due to MeP were observed within 24 hours (for example, rounding of cells, with some cells detaching from plate). Viable cells were counted 5 days following addition of drug. The higher concentrations (3.75 $\mu$M–75 $\mu$M) of MeP resulted in cell lysis and complete loss of cellular architecture, leaving only cellular debris within wells by day 2 following treatment. Trypan blue exclusion was used to confirm viability in cells retaining recognizable structure at all concentrations studied. At lower concentrations MeP-dR did not cause any appreciable cell death and higher concentrations (200 and 400 $\mu$M) less than half of the cells were killed. If the toxicity of MeP-dR is due to very low levels of liberation of MeP by human PNP, then combination with selective inhibitors of human PNP could prevent this toxicity.

The relative toxicity of the prodrug, MeP-dR, and the product, MeP, on wild type melanoma cell viability, was tested. Mel-1 cells were incubated in various concentrations of MeP-dR and MeP for five days. The Mel-1 cells were unaffected by concentrations of MeP-dR as high as 50 $\mu$g/ml while concentrations of the MeP as low as 0.5 $\mu$g/ml were nearly 100% lethal. Similar results have been obtained in T-84, B16, and 16/C cells. Both MeP-dR and MeP are stable under tissue culture conditions as measured by HPLC analysis of supernatants.

EXAMPLE 3
Synthesis of *E. coli* PNP Expression Vectors

A bacterial PNP-encoding sequence was inserted into a plasmid expression vector. *E. coli* (strain, JM101) chromosomal DNA template was obtained using the method described in N. J. Gay, *J. Bacteriol.*, 158:820–825 (1984). Two PCR primers GATCGCGGCCGCATGGCTACCCCA-CACATTAATGCAG (SEQ ID NO: 1) and GTACGCGGC-CGCTTACTCTTTATCGCCCAGCAGAACGGATTCCAG (SEQ ID NO: 2) were used to define the full length coding sequence of the *E. coli* DeoD gene and to incorporate NotI sites at both 5' and 3' ends of the desired product. After 30 cycles of amplification (94° C.×1 minute denaturation, 50° C.×2 minute annealing, and 72° C.×3 minute elongation using 1 ng template, 100 $\mu$l of each primer in a 100 $\mu$l reaction mixture containing 2.5 units taq polymerase, 200 $\mu$M each dNTP, 50 mM KCl, 10 mM Tris Cl (pH 8.3), 1.5 mM $MgCl_2$ and 0.01% gelatin (weight/vol)), a single PCR product of the predicted size (716 base pairs) was obtained. This product was extracted with phenol/chloroform, precipitated with ethanol, digested with NotI, and gel purified using the Gene clean kit (Bio. 101, La Jolla, Calif.).

The amplified bacterial PNP sequence was added to a plasmid eukaryotic expression vector. In order to obtain a vector capable of directing eukaryotic expression of *E. coli* PNP, the LacZ gene was excised from pSVB (Clontech, Palo Alto, Calif.) by digestion with NotI, the vector backbone was dephosphorylated (calf intestinal alkaline phosphatase, GIBCO BRL, Gaithersburg, Md.) and gel purified as above. The PNP insert, prepared as above, was then ligated into the NotI ends of the plasmid backbone in order to create a new construct with PNP expression controlled by the SV-40 early promoter. Correct recombinants (and orientation of inserts) were confirmed by restriction mapping (using twelve restriction digests which cut in both vector and insert), and by reamplification of the full length insert from recombinant plasmid using the primers described above. This procedure yielded the plasmid SV-PNP.

EXAMPLE 4
Transfection of T-84 Colon Carcinoma Cells

Cationic liposome mediated gene transfer was used to transfect T-84 colon carcinoma cells. Briefly, 6 $\mu$g of plasmid containing PNP or LacZ was added to 10 $\mu$g of a 1:1 molar mixture of DOTMA/DOPE (Lipofectin™ (GIBCO/BRL, Gaithersburg, Md.)) in a final volume of 200 $\mu$l DMEM/F12 serum free medium. After a 10 minute incubation at room temperature, the DNA-lipid mixture was added to 500 $\mu$l serum free medium and was used to cover the cells within a tray. Four hours later, transfection medium was removed from each well and 2 ml DMEM/F12 with 10% fetal bovine serum was added.

EXAMPLE 5
Transfection Efficiency

The LacZ gene was transfected into T-84 cells as described above. Briefly, using a lipid-mediated gene transfer protocol identical to that described above, 6 $\mu$g of plasmid containing the *E. coli* LacZ gene under the control of the SV-40 early promoter was transferred into $1-2\times10^5$ T-84 cells. 48 hours after transfection, cells were washed 3 times in PBS, fixed at 4° C.×10 minutes in 0.2% glutaraldehyde, (in 80 mM $NaHPO_2$), rinsed 2 times with PBS, and then stained in a solution containing 80 mM Na$_2$HPO$_4$, 20 mM NaH$_2$PO$_4$, 1.3 mM MgCl$_2$, 3 mM K$_3$Fe(CN)$_6$ 3 mM K$_4$Fe(CN)$_6$ and 1 mg/ml x-gal (5-bromo-4-chloro-3-indolyl-β-D-galactopyranoside). 12 hours after staining, 0.1–1% of the cells treated with β-galactosidase DNA stained positive for gene expression.

X-gal staining of these cells two days after transfection indicated an overall transfection efficiency of 0.1–1% (as determined by percentage of blue cells). No positive cells were observed in untreated T-84 cells, in cells treated with lipid alone, or plasmid DNA alone. Similar conclusions were reached using a LacZ reporter gene containing a nuclear targeting sequence and leading to nuclear staining of recombinant cells.

EXAMPLE 6

Toxicity of MeP-dR-mediated by *E. coli* PNP Expression Vectors

Forty-eight hours following transfection, fresh medium was added and MeP-dR (1 mg/ml in PBS) was added directly to the cells to achieve the desired final concentrations. Cell viability was measured 5 days following treatment as described for the MeP-dR toxicity study.

In one experiment, MeP-DR (160 μM) was added to wells containing untransfected cells, or cells transfected with 10, 20, or 40 μg (FIG. 1) of cDNA containing either the *E. coli* PNP or LacZ genes under control of the SV-40 early promoter (in otherwise comparable vector contexts). After 5 days the cells were removed from each well and the number of dye excluding cells were determined with the aid of a hemacytometer. 30–50% toxicity due to the DOTMA-DOPE transfection protocol is acceptable for cationic liposome mediated gene transfer to T-84 in vitro when performed under optimal conditions. The results of this study are shown in FIG. 1.

In an additional experiment, approximately 2×10$^5$ cells per well were transfected as above using 6 μg of plasmid containing *E. coli* PNP cDNA. Two days after transfection, varying concentrations of MeP-dR (0, 2, 4, 20, 40 and 160 μM) were added to the wells, and after 5 days the dye excluding cells were counted with the aid of a hemacytometer. Concentrations of MeP-dR as low as 4 μM resulted in greater than 80% inhibition of cell growth.

An experiment was also performed in triplicate in which 2×10$^5$ cells per well were transfected with LacZ or PNP using the protocol described for transfection. Two days after transfection, 16 μM MeP-dR was added to one set of the cultures transfected with PNP and one set of the cultures transfected with LacZ. The other PNP and LacZ transfected cultures did not receive drug. The results demonstrate minimal cell killing in all cultures except the PNP transfected, MeP-dR treated culture.

In the above experiments, MeP-dR (160 μM) was minimally toxic to the cells that were not transfected. While expression of the LacZ gene had no influence on toxicity mediated by MeP-dR, MeP-dR killed virtually all of the cells transfected with the *E. coli* PNP (FIG. 1). Substantial killing could also be seen with 16 μM MeP-dR after PNP transfection. These results indicate that low efficiency expression of *E. coli* PNP cDNA (expression in less than 1% of tumor cells) was adequate for nearly 100% transfected cell and bystander cell killing. In addition, because diffusion of MeP into the medium covering the cells could have a substantial dilutional affect, it may be that an even lower fraction of tumor cells expressing *E. coli* PNP in vivo might be able to mediate tumor cell necrosis in the presence of MeP-dR.

EXAMPLE 7

Activity of *E. coli* PNP on MeP-dR in Cell Extracts

The toxicity of MeP-dR in T-84 cells expressing the *E. coli* PNP activity was measured in transfected T-84 cells. Briefly, T-84 cells transfected with 6 μg of plasmid containing either the *E. coli* PNP gene or the LacZ (β-galactosidase) gene as described above were collected by centrifugation 48 hours after transfection and resuspended in 3 volumes of 0.01 M potassium phosphate (pH 7.4), followed by incubation on ice for 15 minutes. The pellet was homogenized, and the sample was centrifuged at 100,000×g for 60 minutes. PNP activity was measured in 100 μl volumes containing 50 mM potassium phosphate (pH. 7.4), 100 μM of MeP-dR, and 1 mg/ml of protein from the cell extract. After incubation for 24 hours at 25° C., the reaction was stopped by boiling, the precipitated proteins were removed by centrifugation, and the reaction mixture was subjected to HPLC by injection onto a Spherisorb ODS1 (5 μl) column (Keystone Scientific Inc., State College, Pa.). The MeP-dR and MeP were eluted with a 30 min isocratic gradient of 50 mM ammonium dihydrogen phosphate buffer (pH 4.5)/acetonitrile (95/5; v/v) at a flow rate of 1 ml/minute. MeP-dR and MeP were detected by their absorbance at 254 nm.

Approximately 24% of the MeP-dR was converted to MeP in extracts from the T-84 colon carcinoma cells transfected with the *E. coli* PNP gene, whereas no conversion occurred in cell extracts from colon carcinoma cells transfected with the LacZ gene. Total PNP activity (human+*E. coli*) measured using inosine as substrate was not changed in T-84 cells transfected with *E. coli* PNP. Thus, despite the relatively low level of expression of the *E. coli* PNP in the transfected cells, a sufficient amount of the MeP-dR was converted to kill all of the cells.

EXAMPLE 8

Detection of MeP in Medium of T-84 Cells Transfected with *E. coli* PNP

MeP-dR (160 μM) was added 48 hours after transfection of T-84 cells with the *E. coli* PNP gene. Five days after the addition of MeP-dR, the medium was collected, and the proteins were precipitated by boiling. After centrifugation, the medium was analyzed for the appearance of MeP by reverse phase HPLC as described above.

MeP was detected only in the culture medium of T-84 cells transfected with *E. coli* PNP. More than 75% of the MeP-dR was converted to MeP over a 5 day period in *E. coli* PNP transfected cells, but not in LacZ transfected cells. These results have significance, because they indicated that 1) untransfected and mock transfected colonic carcinoma cells lack an enzymatic mechanism for conversion of MeP-dR to MeP, 2) as predicted, MeP was readily released into the extracellular medium, so as to establish effective bystander killing, and 3) the extracellular concentrations of MeP generated by recombinant PNP were sufficient to fully explain the bystander killing which was observed. In addition, these results establish that SV-40 driven expression of the prokaryotic PNP in eukaryotic cells (as with the *E. coli* LacZ) leads to a highly active and functional enzyme. Because *E. Coli* PNP is believed to assemble as a homohexamer in prokaryotic cells, the mechanisms of *E. coli* PNP oligomerization are likely to be compatible with eukaryotic protein synthesis.

EXAMPLE 9

Toxicity to Nondividing Cells

Results from experiments indicate that MeP is able to kill non-proliferating cells. This distinguishes MeP from most other antitumor agents. In the first experiment, CEM cells were cultured in 1% serum instead of the normal 10% serum for 48 hours. Under these conditions, the cells stop growing and the cell numbers stabilize at 1.5 to 2 times the original cell numbers. Cell growth continues when cells are returned to culture medium containing 10% serum. Addition of MeP at a final concentration of 10 µg/ml to CEM cell cultures after 48 hours of incubation with 1% serum caused a decline in cell numbers to approximately 25% of their original number which indicated that MeP was toxic to non-proliferating cells.

In the second experiment, the effect of MeP on the incorporation of thymidine into DNA, uridine into RNA, and leucine into protein was determined. RNA and protein synthesis were affected most by treatment with MeP. Effects on DNA synthesis occurred only after effects on RNA and protein synthesis were evident. These results indicated that the inhibitory effect of MeP on either RNA or protein synthesis was responsible for its toxicity. These two functions are vital to all cells regardless of their proliferative state, which indicates that MeP should be toxic to both proliferating and non-proliferating cells. Results confirming these conclusions were also obtained in MRC-5 which are a nontransformed human diploid fibroblast cell line derived from embryonic lung cells.

EXAMPLE 10
Additional Useful Recombinant Vectors

A recombinant retrovirus was made by adding the bacterial PNP sequences to a plasmid retroviral transfer vector that was subsequently passed through packaging cell lines for the production of virus. The retroviral vector, pLNSX (Miller and Rosman, *BioTechniques*, 7:980–991 (1989)), contains a cloning site that is just 3' to an SV40 early promoter which will direct transcription of a coding sequence inserted within the cloning site. The bacterial PNP sequence was ligated into linearized pLNSX. The ligation mixture was used to generate bacterial transformants that were identified by colony DNA analysis, and one clone (pLN/PNP) containing the PNP coding sequence in a 5' to 3' orientation relative to the SV40 promoter was amplified by standard techniques and purified with cesium chloride gradient centrifugation. The plasmid was transfected by lipid-mediated gene transfer into the ψ2 packaging cell line. The supernatant from these cells was harvested 48 hours later, clarified by 0.45 µM filtration and applied to additional ψ2 packaging cell line. In 24–36 hours, the cells were enzymatically detached and plated at a density ⅕ the original density in media supplemented with G418 (1 g/L). Virus producing cells appeared as colonies 7–10 days later that were isolated with cloning rings and assessed for quantity and fidelity of recombinant virus production.

A recombinant adenovirus was made by adding the bacterial PNP sequences to a plasmid adenoviral vector that was subsequently passed through a cell line (293) for the production of virus. The adenoviral plasmid vector, pACCMV (Kolls et al., *Proc. Natl. Acad. Sci. USA*, 91:215–219 (1993)) was linearized with EcoRI and HindIII at the multiple cloning site which is operably linked to the cytomegalovirus (CMV) immediate early promoter. The bacterial PNP-encoding sequence was excised from the SV/PNP plasmid using NotI, and the fragment gel purified and ligated into the NotI site of pSL1180 (Pharmacia, Piscataway, N.J.) to produce the plasmid designated pSL/PNP. The PNP encoding sequence was excised from pSL/PNP with EcoRI and HindIII, gel purified, and ligated into the EcoRI and HindIII site of pACCMV to make the new plasmid designated pACCMV/PNP. Transfection of the pACCMV/PNP into cells conferred dose-dependent toxicity following exposure to the MeP-dR prodrug, confirming that the CMV promoter directed the production of therapeutic levels of the bacterial PNP. The pACCMV/PNP was cotransduced with the pJMI7 vector into human embryonal carcinoma 293 cells that contain adenoviral E1A sequences necessary for viral replication.

EXAMPLE 11
Tyrosinase Promoter Sequence-directed Expression Plasmids

The human tyrosinase regulatory sequence was amplified by the polymerase chain reaction (PCR) from human genomic DNA. The genomic DNA was obtained from nucleated human blood cells by standard techniques. PCR primers A (GAT CGC TAG CGG GCT CTG AAG ACA ATC TCT CTC TGC (SEQ ID NO. 3)) and B (GAT CGC TAG CTC TTC CTC TAG TCC TCA CAA GGT CT (SEQ ID NO. 4)) amplified bp −451, to +78 with the addition of NheI restriction enzyme sites at each end using the sequence of Kikuchio et al., *Biochim. Biophys. Acta*, 2009:283–286 (1989). The PCR reaction used the following conditions for 30 cycles: 94° C.×1 min, 50° C.×2 min, 72° C.×3 minutes. The final product was clarified by phenol/chloroform extraction, digested with NheI, gel purified, and ligated into the NheI cloning site of the commercial luciferase vector, pGL2 Basic (Promega, Madison, Wis.) by standard techniques. Recombinants were screened by restriction mapping and a correctly oriented clone was identified (Tyr-Luc). A plasmid with the tyrosinase promoter in reverse orientation (Rev-Tyr-Luc), for use as a negative control, was also selected. A control vector (SV-LUC) containing the SV-40 virus early promoter and SV-40 enhancer region driving the expression of firefly luciferase (pGL2 control vector, Promega, Madison, Wis.) was used to verify successful transfection of cells. To create a plasmid in which the tyrosinase promoter controlled PNP expression, the PNP gene was substituted for luciferase in the Tyr-Luc. This was accomplished using a XhoI/Sal1 digest to excise the full length PNP gene from SV-PNP, followed by insertion of this fragment into the XhoI/Sal1 sites remaining after a XhoI/Sal1 digest to remove the luciferase gene from Tyr-Luc. The tyrosinase reporter constructs were tested in transient assays. The Lipofectin™ (GIBCO/BRL, Gaithersburg, Md.) transfection protocol was used for all luciferase reporter gene experiments. Cells were seeded at 50% confluency in six-well plates and allowed to grow overnight. Immediately prior to transfection each well was washed three times with sterile phosphate buffered saline (PBS). A single well of a six-well plate was transfected with a ratio of 10 µg liposomes/10–20 µg of plasmid DNA, depending on the cell line. Liposome/DNA complexes were prepared according to manufacturer's instructions. The liposome/DNA complexes were mixed with serum free media (SFM) and a total volume of 700 µl was placed in a single well of a six-well plate. After incubation at 37° C. for 14 to 16 hours, the transfection mixture was aspirated and 2 ml of complete media was added. The cells were harvested after 48 additional hours and luciferase activity was determined using the instructions and reagents of a commercial kit (Luciferase Assay System, Promega, Madison, Wis.). Luciferase reporter gene expression was assessed 48 hours following transfection of various carcinoma cell lines (melanoma, liver, colon, prostate, myeloma, glial, HeLa) with a construct containing a promoterless luciferase vector ("Basic"); a luciferase gene linked to a human tyrosinase promoter in reverse orientation (incorrect orientation to transcribe the luciferase gene) (Rev-Tyr-Luc); a luciferase gene operably linked to the constitutive SV40 early promoter (SV-Luc); or a luciferase gene operably linked to a human tyrosinase promoter (correct orientation to transcribe the luciferase gene) (Tyr-Luc).

As shown in FIGS. 2A–D, the tyrosinase transcriptional promoter sequence specifically restricted expression of the luciferase reporter gene to which it was operably linked, to melanoma cells (Mel-1 and Mel-21). In contrast, the SV40 early promoter constitutively expressed the luciferase gene to which it was operably linked in all transfected carcinoma cell lines. The results demonstrate that tissue-specific promoter sequences can be used to transcriptionally target the expression of a heterologous enzyme to a specific tumor.

Luciferase activity in Mel-1 and Mel-21 cells transfected with the Tyr-Luc construct was comparable to luciferase activity generated by transfection with a plasmid utilizing the SV-40 early promoter to control luciferase gene expression (SV-Luc) (FIG. 2, Panel A). Both negative controls (luciferase without promoter (Basic) and luciferase with tyrosinase promoter sequences inserted in the reverse orientation (Rev-Tyr-Luc)) gave negative results. Negligible Tyr-Luc activity was seen in five additional human cell lines (T-84-colon cancer, U373-glial, HeLa-cervical carcinoma, RPMI 8226-myeloma, GP6FS-prostate), which all showed substantial SV-40 driven reporter gene activity (FIG. 2, Panel B–D). In a sixth cell line, Hep G2 (derived from human liver), the SV-Luc was 28 fold more active than the Tyr-Luc. However, the Tyr-Luc vector had activity above background in the Hep G2 cells. Because the promoterless luciferase vector resulted in similar luciferase activity, luciferase activity in Hep G2 cells is likely to be nonspecific and due to cryptic promoters or enhancers present within the vector itself, rather than nonspecific regulation by the human tyrosinase promoter.

To eliminate possible toxicity associated with the non-hydrolyzable cationic lipid component of the Lipofectin™, an alternative liposome transfection vehicle was used in the killing experiments. A liposome vehicle consisting of a 1:1 (weight/weight) mixture of the cationic lipid DOTAP (1,2-dioleoyloxy-3-(trimethylammonium)-propane) and the neutral lipid DOPE (dioleoyl-phosphatidylethanolamine) (Avanti Polar Lipids) display transfection properties similar to Lipofectin™, but with less toxicity (data not shown). DOTAP/DOPE liposomes were prepared by mixing 0.5 mg of DOTAP and 0.5 mg of DOPE and evaporating the chloroform solvent. Following the addition of 500 µl of cyclohexane, the mixture was placed on dry ice and lyophilized. One ml of sterile water was added to the powdered lipids and the solution was vortexed every 5 minutes for 30 minutes. T-84 or Mel-1 cells were seeded at 30% confluency in 24-well plates and allowed to grow overnight. Immediately prior to transfection, each well was washed three times with sterile PBS. To transfect a single well of a 24-well plate, 7.5 µg of DOTAP/DOPE (1 µg/µl) was mixed with 1.875 µg of plasmid DNA (1 µg/µl) and incubated for 15 minutes. Following a 15 minute incubation, the liposome/DNA complexes were mixed with 266 µl of SFM and added to a single well of a 24-well plate. The plates were incubated for four hours at 37° C., and then the transfection mixture was aspirated and replaced with 500 µl of complete media. Using this protocol, no significant toxicity due to transfection was observed.

In cells that received the PNP or control plasmids, the media was changed two days after transfection and MeP-dR (6-methylpurine-deoxyriboside) added to the appropriate wells to a final concentration of 30 µg/ml. Four days later, the cells were fed by adding fresh media with MeP-dR (30 µg/ml) to the wells without removing the old media. Two days later (day 6), the cells were washed once with PBS, resuspended, and counted in a 20% solution of trypan blue reagent (Trypan Blue Stain 0.4%, Gibco-BRL, Gaithersburg, Md.) using a hemacytometer.

Both T-84 colon carcinoma cells and Mel-1 melanoma cells were transfected using DOTAP/DOPE liposomes (FIG. 3) with the SV-PNP construct, in which the constitutive SV40 early promoter is operably linked to the bacterial PNP gene; or the Tyr-PNP, in which the melanoma specific tyrosinase promoter is operably linked to the bacterial PNP gene; or the Tyr-Luc (see above); or not transfected with any recombinant construct ("no txf"). Only melanoma cells (Mel-1) transfected with the Tyr-PNP construct were susceptible to killing upon administration of the prodrug MeP-dR purine analog nucleoside as demonstrated by comparing FIG. 3A, transfected T-84 colon carcinoma cells, with FIG. 3B, transfected Mel-1 melanoma cells. In contrast, when the constitutive SV40 early promoter was operably linked to the bacterial PNP gene (SV-PNP construct), both T-84 colon carcinoma and Mel-1 melanoma cells transfected with the SV-PNP construct were susceptible to killing upon administration of the prodrug MeP-dR. These results demonstrate that transcriptional targeting of the expression of a purine analog nucleoside cleavage gene permits selective killing of specific tumor cells. Cell death under these conditions correlates with the amount of MeP generated by the action of recombinant *E. coli* PNP on MeP-dR. The transfection of plasmid containing either a cytoplasmic or a nuclear targeted β-galactosidase gene under the same conditions indicated a low transfection efficiency (<0.1% of cells positive for LacZ).

EXAMPLE 12

Method for Identifying Candidate Prodrugs for Bacterial PNP

The following method is useful to identify substrates (prodrugs) that are cleaved more efficiently by the bacterial PNP than by mammalian PNP. Prodrugs identified by this method can then be further assessed by animal studies for determination of toxicity, suitability for administration with various pharmaceutical carriers, and other pharmacological properties.

The method quantitatively measures the cleavage of substrates in vitro. The purine analog nucleosides (0.1 or 1.0 mM) were incubated in 500 µl of 100 mM HEPES, pH 7.4, 50 mM potassium phosphate, and with 100 µg/ml *E. coli* PNP or 0.1 unit/ml human PNP. The reaction mixtures were incubated at 25° C. for 1 hour, and the reactions stopped by boiling each sample for 2 minutes. The cleavage of [$^{14}$C] inosine by each enzyme was determined as a positive control. Each sample was analyzed by reverse phase HPLC to measure conversion from substrate to product. The nucleoside and purine analogs were eluted from a Spherisorb ODSI (5 µm) column (Keystone Scientific, Inc., State College, Pa.) with a solvent containing 50 mM ammonium dihydrogen phosphate (95%) and products were detected by their absorbance at 254 nm, and were identified by comparing their retention times and absorption spectra with authentic samples.

By this analysis, MeP-dR, 2-F-dAdo, 1-deaza-2-amino-6-Cl-purine-riboside, 2-F-5'-deoxyadenosine, 2-Cl-2'-deoxyadenosine were all shown to be good substrates for bacterial PNP and poor substrates for the mammalian PNP, and thus are preferred candidate prodrugs which are eligible for further assessment for use in the methods and compositions described herein to treat malignancies (MeP-dR is a suitable prodrug, as noted above). Substrates 5'-amino-5'-deoxyadenosine, F-araA, and α-adenosine were moderate substrates for bacterial PNP and poor substrates for the mammalian PNP. Substrates xylosyl methylpurine, 2-Cl-2'-F-2'-deoxyadenosine, 2-F-2'-F-2'-deoxyadenosine, and 7-ribosyl-6-mercaptopurine were poor substrates for both enzymes, and therefore would not be candidate prodrugs in conjunction with unmodified E. coli PNP. Similarly, substrates 7-ribosylhypoxanthine and thioguanosine were moderate to good substrates for both enzymes and also would not be candidate prodrugs for treating tumors using the compositions and methods described herein.

2-F-dAdo and F-araA have demonstrated antitumor activity not related to the production of fluoroadenine. Therefore, in methods described herein, the antitumor activity of these two substrates is likely to be potentiated by metabolism by the E. coli PNP. In addition, the metabolism and toxicity of these two agents can be prevented by incubation in the presence of 2'-deoxycytidine.

Thus, by combining these substrates with 2'-deoxycytidine, antitumor activity related only to the production of fluoroadenine is possible.

TABLE II

Screening of nucleotides as substrates for E. coli PNP

| | Percent of substrate cleaved by: | | | |
|---|---|---|---|---|
| | E. coli PNP | | Human PNP | |
| substrate | 100 μM | 1 mM | 100 μM | 1 mM |
| I. Nucleosides that are good substrates for E. coli PNP but are at best poor substrates for human PNP. | | | | |
| MeP-dR | 93 (87) | 29 (24) | 0 | 0 |
| | 91 (86) | 45 (21) | 0 (86) | 0 (47) |
| FdAdo | 56 (69) | 14 (18) | 0 (70) | 0 (30) |
| | 60 (86) | 38 (21) | 0 (86) | 0 (47) |
| 1-deaza-2-amino-6-Cl-purine-riboside | 62 (87) | 16 (23) | 0 (88) | 0 (52) |
| | 41 (86) | 15 (21) | 0 (86) | 0 (47) |
| 2-F-5'-deoxy-adenosine | 81 (86) | 30 (21) | 0 (88) | 0 (50) |
| | 65 (86) | 44 (21) | 0 (86) | 0 (47) |
| 2-Cl-2'-deoxy-adenosine | 41 (86) | — | 0 (87) | — |
| 7-ribosyl-3-deazaguanine | 88 (91*) | 67 (43*) | 0 (0*) | 0 (0*) |
| | 84 (90*) | 83 (39*) | 0 (95*) | 0 (43**) |
| # | 80 (85**) | — | 0 (87**) | — |
| 7-ribosyl-6-mercaptopurine**** | 0 | 0 | 0 | 0 |
| | 0 (86) | 0 (21) | 0 (86**) | 0 (47) |
| # | 45 (65**) | 35 (16**) | 0 (87**) | 0.37 (40**) |
| 500 μM # | 10 (85**) | — | 0 (87**) | — |
| II. Nucleosides that are moderate substrates for E. coli PNP but are at best poor substrates for human PNP. | | | | |
| 5'-amino-5'-deoxy-adenosine | 5 (86) | 1 (19) | 0 (89) | 0 (53) |
| | 9 (86) | 5 (21) | 0 (86) | 0 (47) |
| # | 29 (85**) | — | 0 (87**) | — |
| F-araA | 3 (86) | 3 (21) | 0 (88) | 0 (50) |
| | 5 (86) | 12 (21) | 0 (86) | 0 (47) |
| α-adeno-sine | 0 (86) | 0 (21) | 0 (88) | 0 (50) |
| | 3 (86) | 2 (21) | 0 (86) | 0 (47) |
| | 0 (85**) | — | 0 (87**) | — |
| III. Nucleosides that are at best poor substrates for both enzymes. | | | | |
| xylosylmethyl-purine | 0 (86) | 0 (21) | 0 (88) | 0 (50) |
| | 0 (86) | 0 (21) | 0 (86) | 0 (47) |
| xylosyl adenine | 0 (78) | — | 0 (81) | — |
| | 1 (56) | — | 0 (82) | — |
| 2-Cl-2'-F-2'-deoxy-adenosine | 0 (86) | 0 (21) | 0 (88) | 0 (50) |
| | 0 (86) | 0 (21) | 0 (86) | 0 (47) |
| 2-F-2'-F-2'-deoxy-adenosine | 0 (86) | 0 (21) | 0 (88) | 0 (50) |
| | 0 (86) | 0 (21) | 0 (86) | 0 (47) |
| 2',3'-dideoxy adenosine*** | 1.6 (64**) | 0 (15**) | 1.2 (85**) | 0.2 (49**) |
| | # 0 (85**) | — | 0 (87**) | — |
| 2',3'-dideoxy inosine*** | 2.7 (64**) | 3 (15**) | 1.1 (85**) | 2.4 (49**) |
| | # 0 (85**) | — | 0 (87**) | — |

TABLE II-continued

Screening of nucleotides as substrates for E. coli PNP

| | Percent of substrate cleaved by: | | | |
|---|---|---|---|---|
| | E. coli PNP | | Human PNP | |
| substrate | 100 μM | 1 mM | 100 μM | 1 mM |
| 3'-deoxy adenosine | 0 (62**) | 0 (16**) | 0 (87**) | 0 (45**) |
| | # 0 (85**) | — | 0 (87**) | — |
| 5'-carboxamide of adenosine | # 1.2 (78) | — | 0 (81) | — |
| | 0.1 (56) | — | 0 (82) | — |
| Isopropylidine of the 5'-carboxamide of adenosine | # 1 (78) | — | 0 (81) | — |
| | 0 (56) | — | 0 (82) | — |
| IV. Nucleosides that are substrates for both enzymes. | | | | |
| 7-ribosyl-hypo-xanthine | 16 (86) | 30 (21) | 3 (86) | 5 (47) |
| | 49 (86) | 38 (21) | 73 (86) | 73 (47) |
| thioguanosine | 49 (86) | 38 (21) | 73 (86) | 48 (47) |

In Table II, above, each of the numbers represent the percent conversion of the purine analog nucleoside by the phosphorylase indicated. The numbers in parentheses are percent conversion of the inosine to hypoxanthine in the same experiment. "*" indicates that MeP-dR was used as the control agent in place of inosine. "" indicates that 6-thioguanosine was used as a positive control in place of inosine. "*" indicates questionable activity. "****" indicates that the assay was sensitive to boiling. "#" indicates that these assays were terminated by filtering and not by boiling.

EXAMPLE 13
In vivo Treatment with Bacterial PNP and MeP-dR

The utility of the bacterial PNP and prodrugs such as MeP-dR to inhibit cancer growth in vivo was demonstrated in mice engrafted with tumors expressing the bacterial PNP gene. The first step required the production of a recombinant retrovirus containing a constitutively expressed bacterial PNP gene, as described above. The bacterial PNP encoding sequence was excised from the SV/PNP plasmid and ligated by standard techniques into the pLNSX vector. The resulting vector, pLN/PNP used the SV40 early promoter to constitutively direct the bacterial transcription. This plasmid vector was transfected into the ψ2 packaging cell line. The supernatant collected from these cells 48 hours later was used to infect additional ψ2 packaging cells. Twenty-four hours later, the cells were replated at a lower density (1:5–1:10) in media containing G418 in order to select for clones containing the retroviral sequences. Several clones were selected and titers of clones determined by standard techniques. A clone with the highest titer was selected as the source of recombinant, LN/PNP virus, and used to infect tumor cells.

The murine mammary carcinoma cell line, 16/C, was modified to constitutively express the bacterial PNP by infection with the LN/PNP virus. The 16/C cells were plated at a subconfluent density, and the LN/PNP virus contained within the supernatant from the ψ2-producer line was applied in the presence of polybrene (5 μg/ml) for several hours. The media was changed to normal media for 24 hours, after which the cells were enzymatically detached and plated at a lower density in media containing G418 (1 gm/L) to select infected cells. A polyclonal mixture of G418 resistant cells, to be referred to here as "16/C-PNP cells", was amplified in number for engraftment into mice. Further description of the methods for generation of stable PNP expressing tumor cell lines is also provided below.

Figure 4:
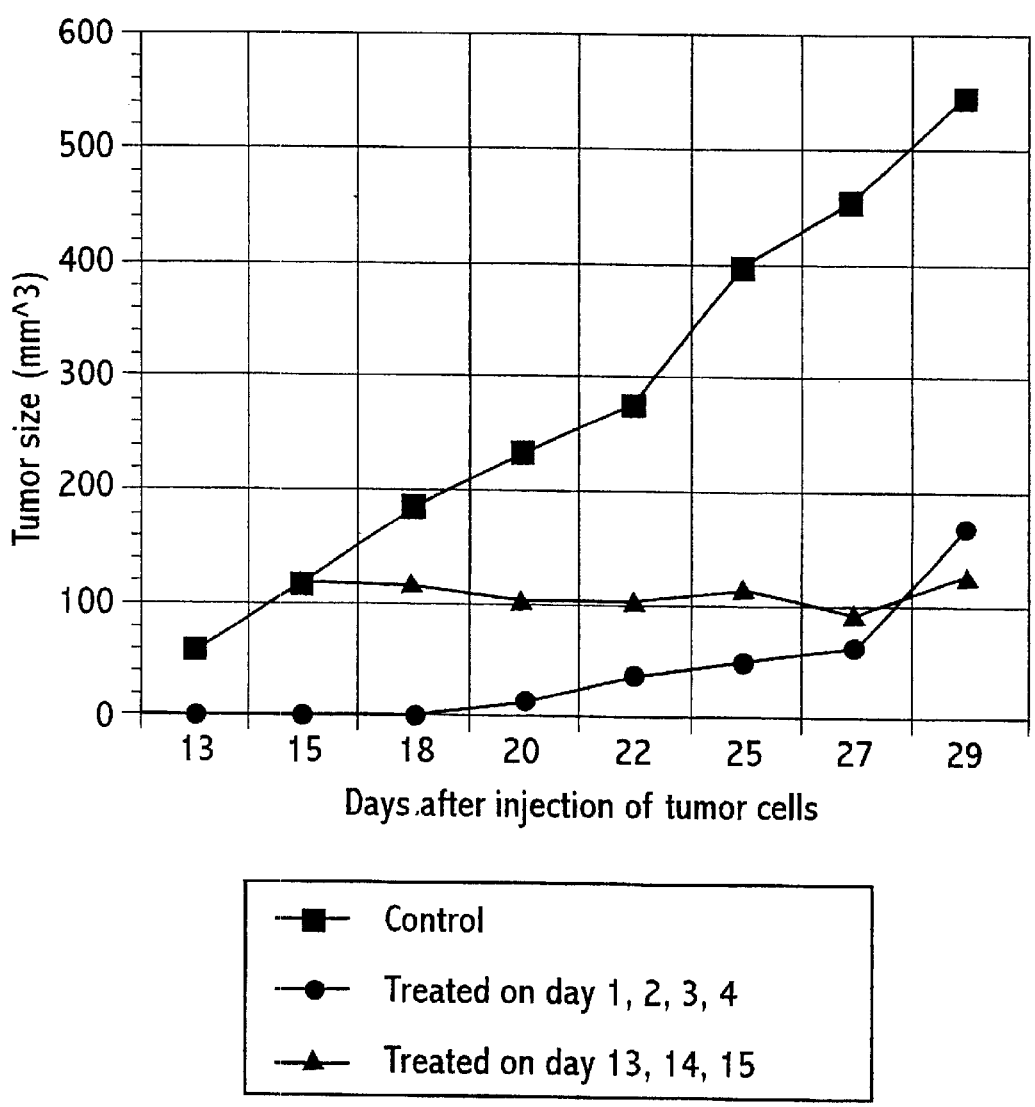
FIG. 4 shows the difference in in vivo development of tumors in athymic nude mice engrafted with murine mammary carcinoma 16/C cells transduced with the recombinant retroviral expression vector LN/PNP (which directs expression of E. coli PNP) depending on time of administration of MeP-dR prodrug. No injection of MeP-dR (control); injection of MeP-dR on days 1–4 post engraftment (early rx); injection of MeP-dR on days 13–15 post engraftment (late rx) are shown.

Athymic (nude) mice were engrafted with the 16/C-PNP cells. Each mouse received $2\times10^6$ cells subcutaneously (sq) in the left flank on day 1. The results are shown in FIG. 4. Control animals (n=4) were maintained under normal nude mouse conditions that resulted in measurable tumors by day 13. The tumors in all of the control mice continued to increase in size through day 29 following engraftment. The early treatment group (n=4) was treated by intraperitoneal (IP) injections of 6-MeP-dR at 100 mg/kg, a dose just below the maximum tolerated dose, each day for the first 4 days (days 1–4). One of these mice was sacrificed at day 8 to study tumor histology, and two more died at day 20, from undetermined causes, possibly due to the very high levels of prodrug administered. Importantly, none of the mice had any detectable tumor up to 18 days postengraftment. One mouse developed a very small tumor at day 22. The late treatment group (n=4) was treated by intraperitoneal injections of 6-MeP-dR at 100 mg/kg each day on days 13, 14, and 15 post engraftment. All of the late treatment group had tumors of comparable size to the controls on day 13. Unlike the controls, the tumors in the late treatment group did not increase in size after day 15. All of these animals survived for the complete experiment. These results clearly show that the combination of the bacterial PNP plus prodrug causes a reduction in tumor growth in vivo.

EXAMPLE 14
Generation of Stable-cell Lines Expressing *E. coli* PNP

High level bystander killing of cancer cells in vitro was evaluated using stable, PNP expressing cell lines. The *E. coli* PNP gene was cloned into the Hind III and Stu I sites of LNSX, a retroviral vector (Miller et al., *Biotechniques* 7:980–990 (1989)) in which the neomycin resistance gene is LTR-driven, and the SV40 early promoter regulates *E. coli* PNP expression. Cloning was accomplished by excising the *E. coli* PNP gene from SV-PNP and directionally cloning the fragment into LNSX (Sorscher et al., *Gene Ther.,* 1:233–238 (1994)). The construct was then transfected using the Lipofectin reagent (Gibco BRL) into an ecotropic 3T3-based packaging cell line (ψ2). In order to obtain a higher retroviral titer, supernatants from the initial viral collection were used to transduce fresh ψ2 cells. Fresh medium and G418 (Gibco BRL) were added every 3 days. Producer cells capable of releasing $10^4$–$10^5$ infectious particles/ml growth medium were obtained, and used to transduce murine melanoma (B16), murine breast carcinoma (16/C), and human glioma (D54) cell lines. Three days following addition of virus, transduced cells were selected with G418 as above.

EXAMPLE 15
Cloning of the Human Tyrosinase Promoter Region and Construction of Luciferase Reporter Vectors Two polymerase chain reaction primers, (GATCGCTAGCGGGCTGAAGACAATCTCTCTGC (SEQ ID. No. 6) and GATCGCTAGCTTCCTCTAGTCCTC ACAA-GGTCT) (SEQ ID No. 7) were used to define the 529 base pairs (bp) of the human tyrosinase promoter immediately upstream of the start of translation (−451 to +78) and to incorporate Nhe I sites (underlined) at both 5' and 3' ends of the desired product (Giebel et al., *Genomics,* 9:435–45 (1991); Kikuc et al., *Biochem. Biophys. Acta.,* 1009:283–6 (1989)). Template DNA was prepared from whole human blood as described by Sorscher et al., *Lancet,* 337:1115–8 (1991). After 30 cycles of amplification, a single PCR product of the predicted size (553 base pairs) was obtained (94° C.×1 min, denaturation, 50° C.×2 minutes annealing, and 72° C.×3 minutes elongation) using 1 ng template, 100 ng of each primer in a 100 μl reaction mixture containing 2.5 units Taq polymerase, 200 mM of each dNTP, 50 mM KCl, 10 mM Tris-HCl (pH 8.3), 1.5 mM $MgCl_2$, and 0.01% gelatin (weight/vol.). This product was extracted with phenol/chloroform, precipitated with ethanol, digested with Nhe 1, and gel purified. A luciferase reporter gene vector lacking any promoter (pGL2 Basic vector, Promega) was cut with Nhe I and the above PCR product was ligated immediately upstream of the luciferase gene. Recombinants were screened by restriction mapping and a correctly oriented clone was identified (Tyr-Luc). A plasmid with the tyrosinase promoter in reverse orientation (Rev-Tyr-Luc), for use as a negative control, was also selected.

EXAMPLE 16
Cancer Cell Lines for Studying Gene Activation by the Tyrosinase Promoter B16 and 16/C are of murine origin and were a gift of Dr. W. Waud, Southern Research Institute, Birmingham, Ala.; all other cell lines are of human derivation. Mel-I (melanoma) was provided by T. Carey, University of Michigan as UMCC-Mel-1. Mel-21 (melanoma) was provided by M. B. Khazaeli, University of Alabama, Birmingham. GP6F2 (prostate) was a gift of M. Moore, Grady Memorial Hospital, Atlanta, Ga. U-373 and D54 (glioma) were provided by Yancey Gillespie, University of Alabama, Birmingham. HeLa (cervical carcinoma), Hep G2 (hepatocellular carcinoma), and T-84 (colon carcinoma) were obtained from the American Type Culture Collection. Mel-1, Mel-21, Hep G2, and HeLa cells were cultured in Earle's minimal essential medium containing Earle's salts, and 1% L-glutamine (Gibco-BRL), with 10% fetal bovine serum and 1% nonessential amino acids. T-84 and GP6F2 cells were cultured in a 1:1 mixture of Dulbecco's modified Eagle's medium and nutrient mixture F-12 (Ham's) (Gibco-BRL) with 15 mM HEPES, 1% L-glutamine, and 10% fetal bovine serum. B 16, 16/C and RPMI 8226 cells were cultured in RPMI medium 1640 with 1% L-glutamine (Gibco-BRL) and 10% fetal bovine serum. All cells were cultured at 37° C. with 85% humidity and 5% $CO_2$.

EXAMPLE 17
Luciferase and X-gal Assays

Each plate was washed three times with PBS and 100 μl of lysis buffer (Luciferase Assay System, Promega) was added to each well of a six-well plate. After 15 minute incubation at 37° C., the lysate and cell debris were collected. Forty μl of the lysate was added to 100 μl of luciferase assay substrate (Promega) in a clear polystyrene 12×75 mm tube, immediately placed in a luminometer (Analytical Luminescence Laboratory model 2010) and light production measured for 15 seconds. X-gal staining for transfection efficiency using LacZ constructs was as described by Sorscher el al., *Gene Ther.,* 1:233–238 (1994).

EXAMPLE 18
Killing and Proliferation Assays

In some studies, cellular toxicity (percentage of dead cells) was measured by LDH release from dying cells (Promega, Cytotox™ 96 kit). The proliferation assay (living cell number/well) was performed using a measurement of tetrazonium conversion to formazin during cell growth (Cell Titer™ 96 kit). Since these two assays are designed to study approximately 10,000 cells per condition (using 96 well trays), measurements of bystander effects below approximately 1% (100 transduced cells) were effectively limited by difficulty in accurately counting very small numbers of transduced, viable cells.

EXAMPLE 19
Implantation of Tumor Cells into Mice

Transduced 16/C cells were implanted in mice by subcutaneous injection of approximately $10^6$ cells harvested from the cultures of stably transduced 16/C cells described above. The mice were examined visibly for tumor growth and those with developing tumors were maintained. To prepare mice for use in the in vivo experiments, the tumors were removed from mice with significant tumor growth and cut into 30–60 mg pieces. One 30–60 mg piece of the tumor was subcutaneously implanted into the subaxillary region of each female B6C3F1 mouse. The tumors were allowed to develop and mice with tumors of 100 $mm^3$ were used.

For studies conducted with nu/nu mice, cells obtained from stable cultures of transduced cell lines were injected subcutaneously into the right or left flank of the mice. Mice with visible tumor growth were used for further studies. For the administration of purine prodrug, mice were administered MeP-dR or F-araAMP by IP injection.

EXAMPLE 20
Bystander Killing by Cell Lines Expressing E coli PNP

Figure 5A:
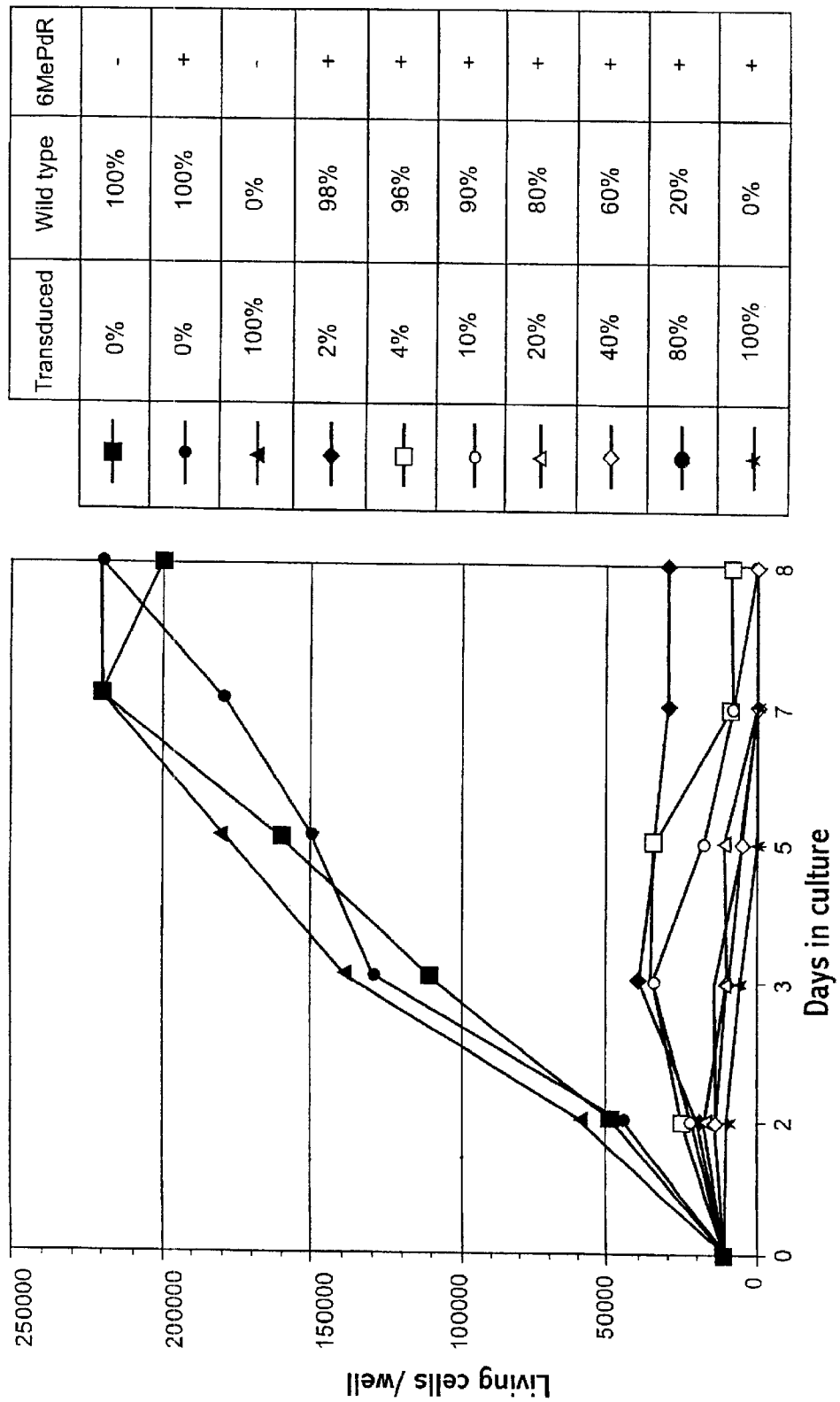
FIGS. 5A and 5B show mixing experiments in which the transduced and wild type B16 (FIG. 5A) or 16/C (FIG. 5B) were cocultured. Complete abrogation of cellular proliferation was observed when as few as 2% of the cultured cells expressed E. coli PNP under the regulatory control of an SV-40 promoter. A high level bystander effect was also observed when either B16 or 16/C cells expressed E. coli PNP, as measured by a standard cellular LDH release assay. Growth characteristics of transduced and wild type (nontransduced) B16 cells were identical in the absence of drug; the same was true of the wild type and transduced 16/C cell lines.
Figure 5B:
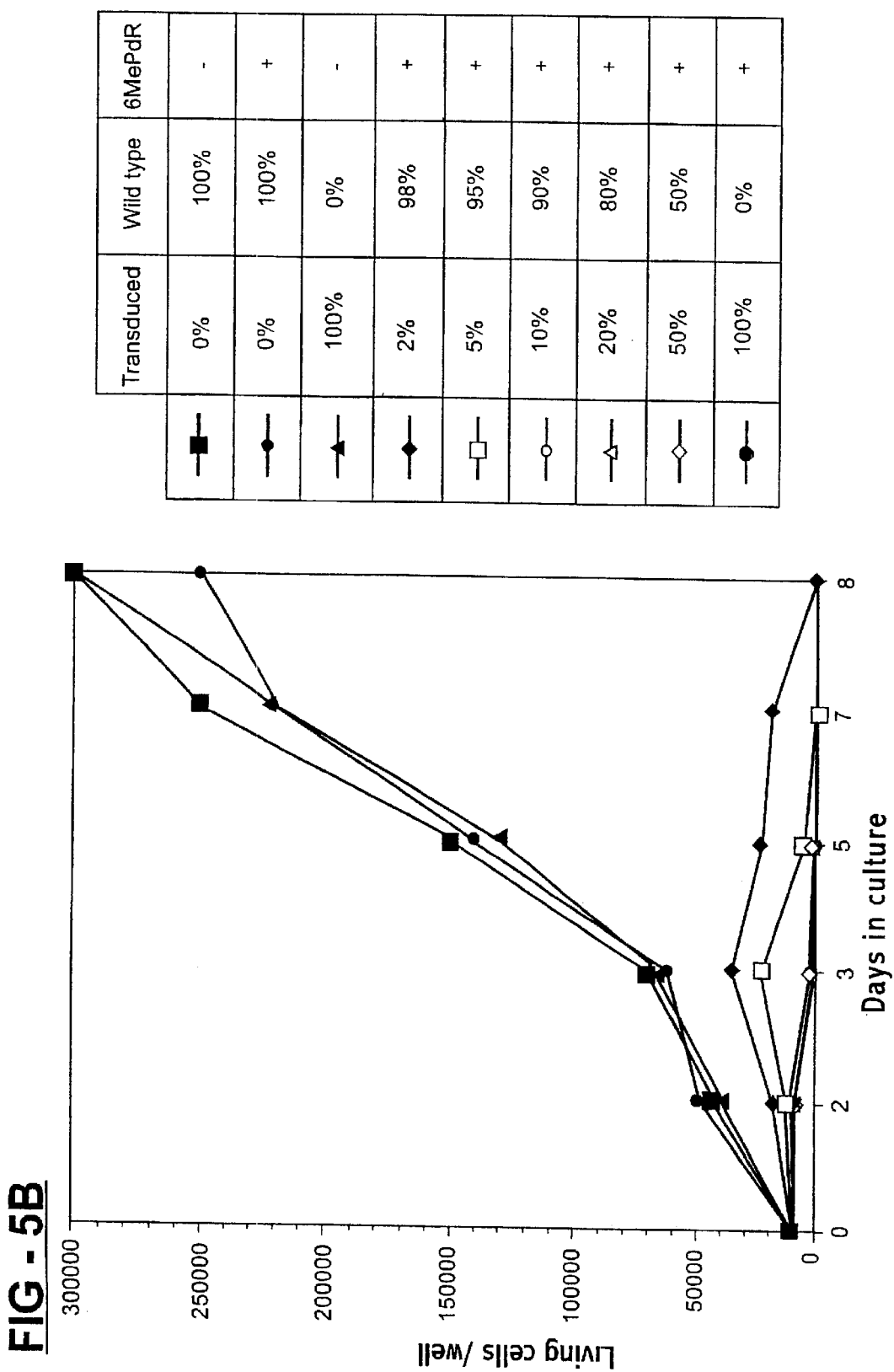

Transient E. coli PNP expression in a human colonic carcinoma cell line is capable of mediating total cell population killing in vitro even when only approximately 1% of cells express the E. coli PNP gene (FIG. 1). The growth characteristics of wild type and transduced B16 cells, and wild type and transduced 16c cells were the same in the absence of MeP-dR. In FIG. 5, a dose of MeP-dR (20 $\mu$g/ml) which is not toxic to untransduced B16 melanoma or 16/C breast cancer cells was added to mixed cultures containing an increasing population of transduced E. coli PNP expressing cells. Effects on both cell proliferation and cell survival were evaluated in the presence or absence of MeP-dR. In these experiments, concentrations of MeP-dR which had no effect on untransduced (wild type) B16 (FIG. 5A) or 16/C (FIG. 5B) tumor cells completely eliminated cell proliferation even when as few as 2% of cells in culture expressed the E. coli PNP gene. Based upon an LDH release assay, total population cell killing required that 10% of B16 cells and $\leq$1% of 16/C cells expressed the PNP gene. When E. coli PNP activity in the transduced B16 and 16/C cells was assayed by direct enzymatic measurement using cell free extracts, the activity measured in transduced 16/C cells was approximately 4 fold higher than in B16 cells. (16/C:10.7 nmoles MeP-dR converted/mg cell protein/hr (n=6); B16: 2.4 nmoles MeP-dR converted/mg cell protein/hour (n=2); background activity in non-transduced 16/C and B16 cells was 0 (n=4 measurements for each cell line)).

EXAMPLE 21
Killing of Malignant Cells in vivo: Growth of 16/C Mouse Breast Carcinoma in B6C3F1 Mice Six mice (B6C3F1) per group with established wild type 16/C tumors were treated with an aqueous control solution, MeP-dR (100 mg/kg IP qdx3d) or 2-fluoro-arabinofuranosyladenine monophosphate (F-araAMP) (100 mg/kg IP, 5 idx3d). The wild type tumors grew rapidly in the presence or absence of either of the prodrugs. In addition, there was no statistically significant delay in tumor growth attributable to either prodrug. (Table III, Wild-type 16/C treatment). This demonstrated that the prodrug was not toxic to the mice at the doses given and had no effect on non-PNP expressing tumor cells.

Six mice per group with established PNP-transduced 16/C tumors were treated with aqueous control solution, MeP-dR or F-ara AMP, as above. Control solution treated tumors grew rapidly, comparable to the rate of growth observed with the wild type tumors. Complete tumor regression was observed in three of six in the MeP-dR treated group. In addition, a statistically significant delay in the time necessary for three tumor doublings was noted for the MeP-dR treated group (p<0.01) and the F-araAMP treated group (p<0.01). (Table III, 16/C-PNP treatment.)

TABLE III

Effect of MeP-dR and F-araAMP on the growth of wild-type 16/C tumors and 16/C tumors transduced with the E. Coli PNP gene (B6C3F1)

| Dose/day** Treatment | Regressions/ (mg/kg) | Complete Nonspecific Total | to double 3 Deaths/Total | Days for tumor Day delay times * mean/SD | (Treated-control) |
|---|---|---|---|---|---|
| Wild-type 16/C | | | | | |
| Vehicle | — | 0/6 | — | 6.2 ± 3.7 | — |
| MeP-dR | 100 | 0/6 | 0/6 | 8.6 ± 0.7 | 2.4 |
| F-araAMP | 500 | 0/6 | 0/6 | 8.9 ± 2.0 | 2.7 |
| 16/C-PNP | | | | | |
| Vehicle | — | 0/6 | — | 8.8 ± 1.1 | — |
| MeP-dR | 100 | 3/6 | 2/6**** | 14.2 ± 3.2*** | 5.4 |
| F-araAMP | 500 | 0/6 | 0/6 | 12.1 ± 1.6*** | 3.3 |

*refers to the mean ± the standard deviation of the days to 3 doublings of the tumors that continued to grow in the presence of drug, and does not include the tumors that completely regressed.
**refers to mice (B6C3FI) implanted (SC) with wild-type 16/C tumors of E. coli PNP-transduced 16/C tumors (16/C PNP). Three days post implantation, when tumors had grown to approximately 100 mg, the annnals were treated (IP) with vehicle, 100 mg/kg of MeP-dR once a day for three days, or 100 mg/kg of F-ara-AMP five times a day (2 hour intervals) for three days.
***refers to a significant difference from the growth rate of 16/C-PNP tumors in animals treated with vehicle, p < 0.01, Student's t test. The growth rate of wild-type 16/C tumors treated with MeP-dR and F-araAMP was not significantly different from vehicle-treated tumors, and the growth of vehicle-treated wild-type 16/C tumors was not significantly different from the growth rate of vehicle-treated 16/C-PNP tumors.
****in the in vivo experiments described, MeP-dR dosages were given at just below the maximum tolerated dosage. As expected, the near lethal dosage of MeP-dR resulted in sporadic animal death (occurred in some animals 1–2 weeks following complete or substantial tumor regression).

EXAMPLE 22

Immunological Clearance of Tumors

To demonstrate that the efficacy shown above was not due to immune response and clearance of PNP-expressing tumors, immune deficient mice (nu/nu) were studied using a similar protocol. Four to five nude (nu/nu) mice per group were inoculated with wild type murine breast carcinoma cells (16/C cell line), or PNP transduced 16/C cells. Mice with established tumors (approximately 100 mm$^3$) were treated with MeP-dR (100 mg/kg/d IP×3 d) or F-araAMP (100 mg/kg/IP 3 id×3 d).

Figure 6:
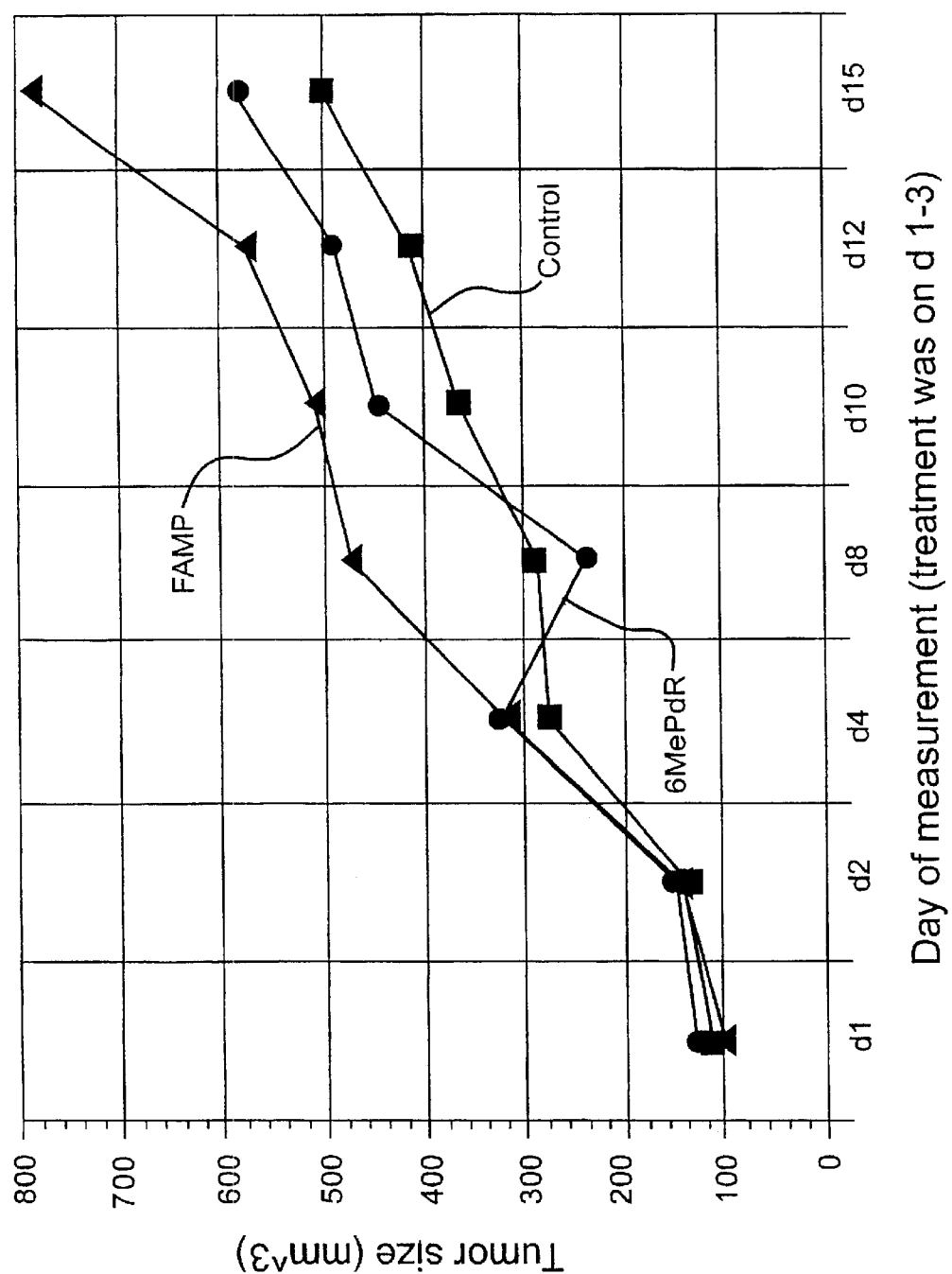
FIG. 6 shows the effect of MeP-dR and F-araAMP on the growth of wild-type 16/C tumors in animals. Both compounds had only a small effect on tumor growth. These results are in contrast with those in FIGS. 4 and 7.
Figure 7:
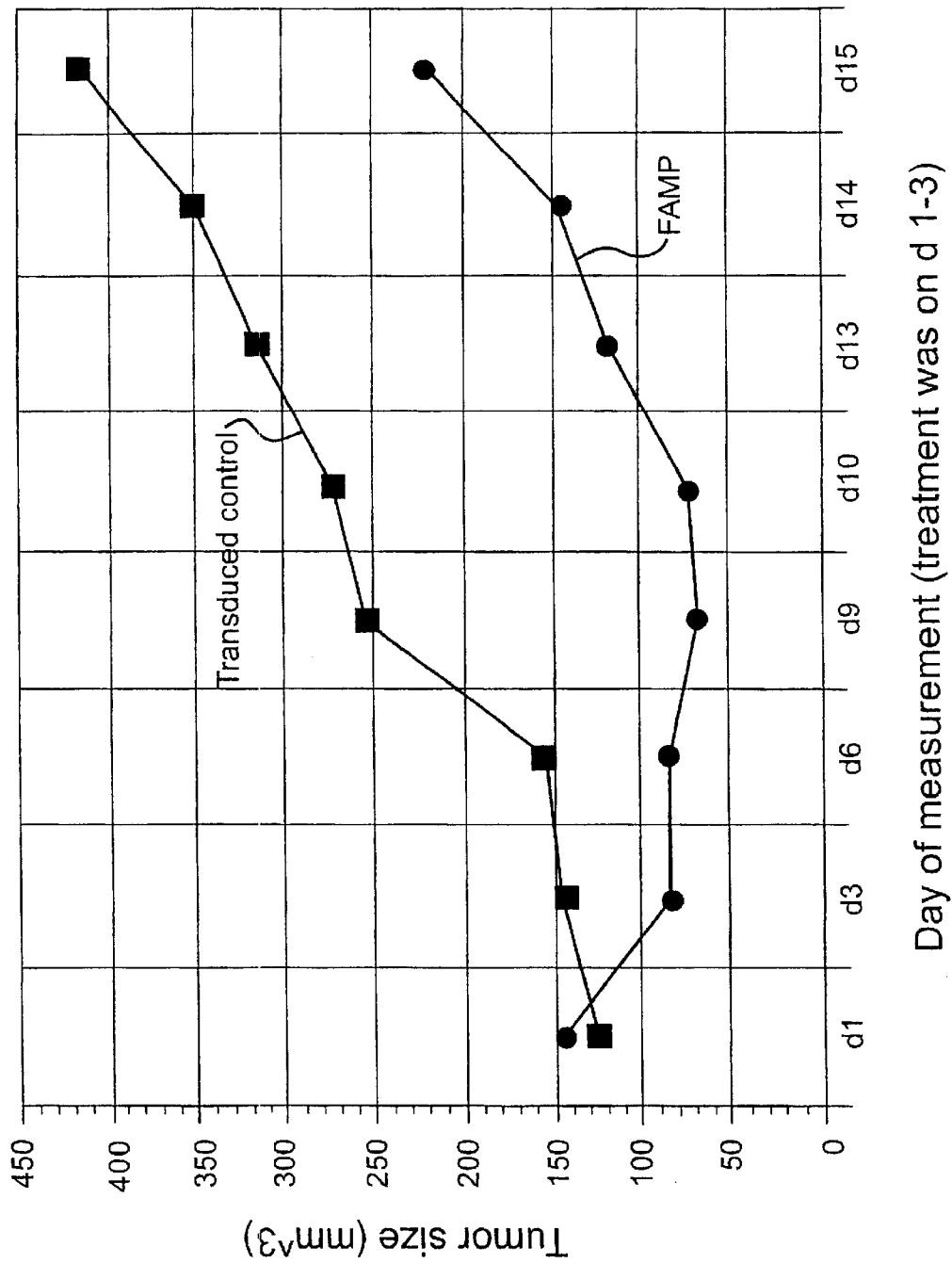
FIG. 7 shows the effect of F-araAMP on the growth of 16/C tumors expressing E. coli PNP. F-araAMP significantly inhibited the growth of these tumors. Contrast with the effect of F-araAMP on wild-type tumors in FIG. 6.

Wild type tumors grew rapidly following either vehicle or prodrug administration (FIG. 6). Animals with PNP-transduced tumors which were treated with F-araAMP for three days demonstrated evidence of growth delay for at least ten days, FIG. 7. Animals treated with MeP-dR showed substantial antitumor effects whether treated at a time when tumors were established (days 13–15) or immediately following tumor cells inoculations (days 1–4), FIG. 4.

EXAMPLE 23

In vivo Activity of MeP-dR Against Human Glioma Transduced with E. coli PNP

Female athymic nude mice (nu/nu) were implanted sc with 2×10$^7$ cells of either D54 parental tumor cells (D54-wt) or D54 tumor cells that had been transduced with the E. coli PNP (D54-PNP). After the tumors had grown to approximately 150 mg, they were treated ip with either vehicle or 67 mg/kg of MeP-dR (IP) once a day for 3 days (days 6, 7 and 8 after implantation). The tumor sizes were measured twice a week after treatment.

Figure 8:
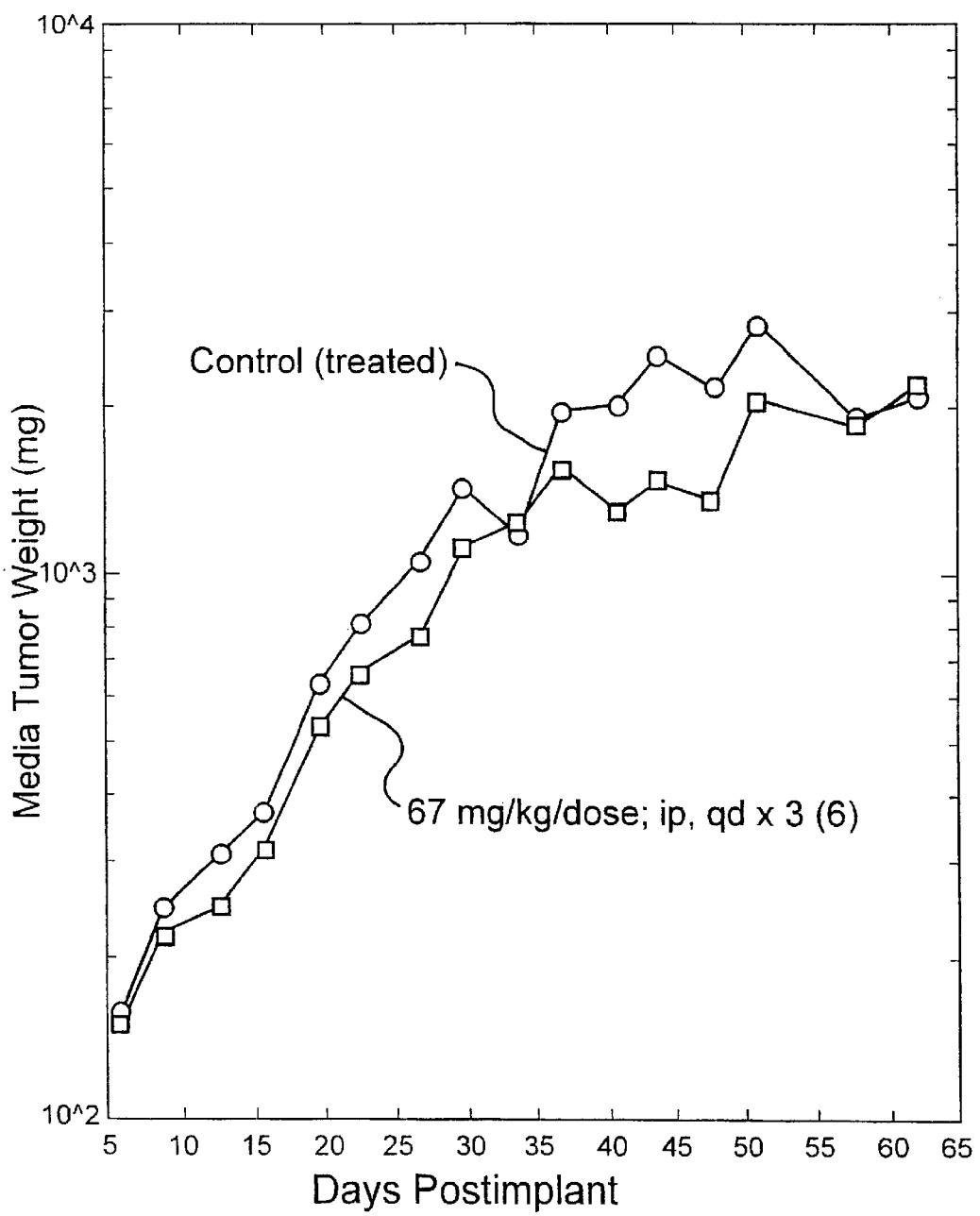
FIGS. 8 and 9 show the effect of MeP-dR on the growth of wild-type D54 tumors (FIG. 8) and E. coli PNP expressing D54 tumors (FIG. 9). These two figures are a graphical representation of the data shown in Table IV.
Figure 9:
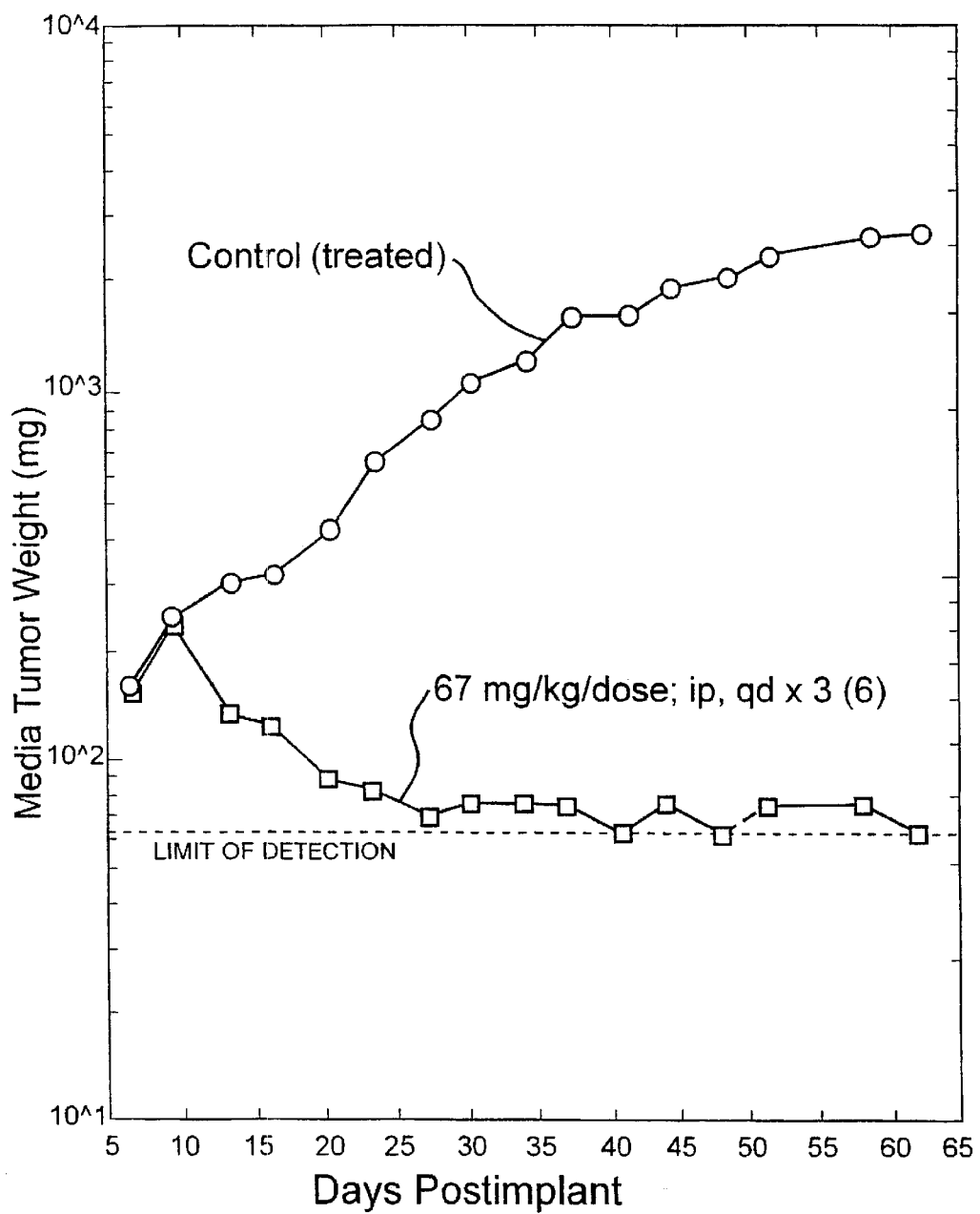

There were 6 of 6 complete regressions in mice with the D54-PNP tumors that were treated with MeP-dR (Table IV). Four of these animals had no detectable tumors at the termination of the experiment. MeP-dR had little effect on the D54-wt tumors. There was little or no loss of weight in the animals that were treated with 67 mg/kg of MeP-dR, regardless of tumor implanted. Animals were followed for a total of 65 days. No treated animals died in these experiments (FIGS. 8 and 9).

\*\*, Mice (NCr-nu) were implanted (SC) with wild-type D54 tumors or E. coli PNP-transduced 16/C tumors (D54-PNP). When tumors had grown to approximately 100 mg, the animals were treated (IP) with vehicle or 67 mg/kg of MeP-dR once a day for three days.

Figure 10:
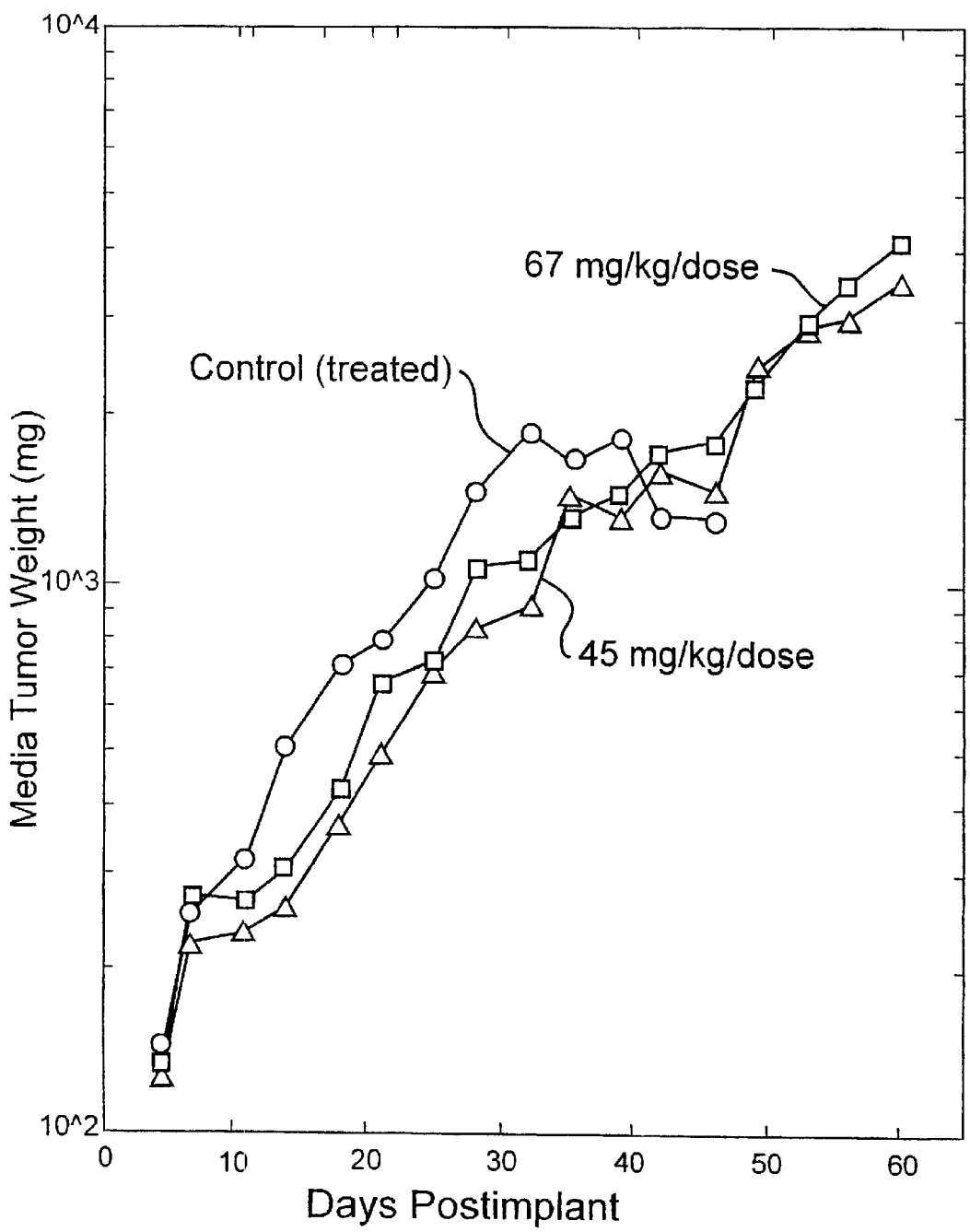
FIGS. 10 and 11 are a confirmation study of the experiment shown in FIGS. 8 and 9 that show the effect of MeP-dR on the growth of wild-type D54 tumors (FIG. 10) and E. coli PNP expressing D54 tumors (FIG. 11). These two figures are a graphical representation of the data shown in Table V.
Figure 11:
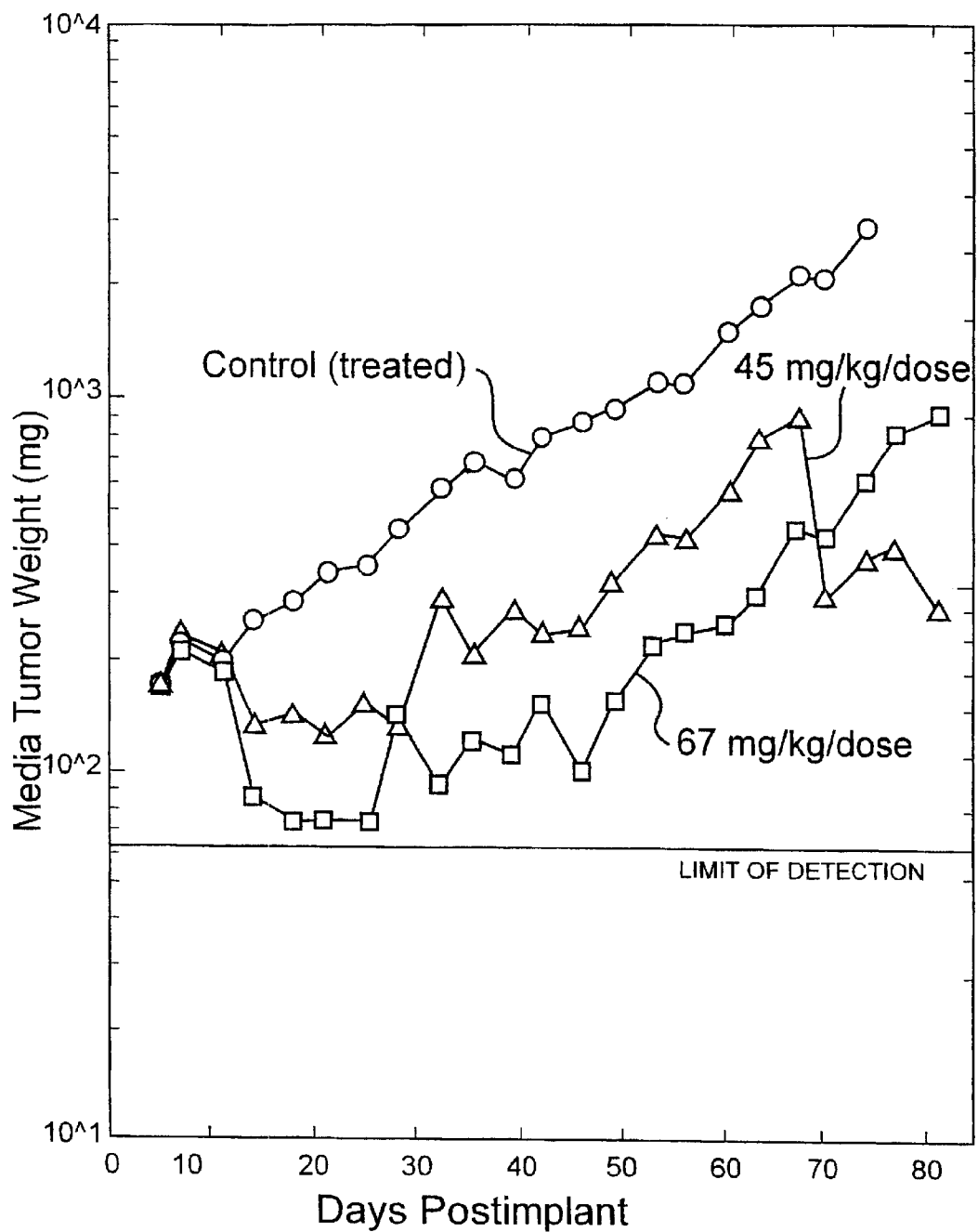

A confirmation experiment was set up exactly as described above, except that animals were treated with two doses of MeP-dR (45 and 67 mg/kg) (FIGS. 10 and 11). The results of this experiment were similar (Table V). There were 8 of 10 complete regressions in mice bearing the D54-PNP tumors that were treated with 67 mg/kg of MeP-dR. In 4 mice the tumors subsequently returned and grew. There were still 4 of 10 tumor-free survivors 60 days after the treatment had stopped. Treatment with 45 mg/kg MeP-dR also had a marked affect on mice bearing the D54-PNP tumors. There were 2 of 10 complete regressions and 3 partial responses. There were no tumor-free survivors in animals bearing the D54-PNP tumor that were treated with 45 mg/kg MeP-dR. Again, there were no partial of complete remissions in animals bearing the D54 wild-type tumors treated with either 45 or 67 mg/kg of MeP-dR. The delay in the time required to double twice due to treatment with MeP-dR was 5 to 6 days in the non-transduced tumors and greater than 24 days in transduced tumors. In this experiment, the growth rate of the D54-PNP tumors was considerably slower than it was in the first experiment. There was no change in the growth rate of the D54-wt tumors. The reason for the slow growth rate of the D54-PNP tumors in this experiment is not known. The Figures shown (FIGS. 8–11) only describe the growth of tumors that did not show complete regression. (In other words, if a tumor was too small to measure, it was not included in the average size). This means that the overall tumor regressions in the D54 PNP group are actually much more pronounced than they appear in FIGS. 8–11.

TABLE IV

Effect of MeP-dR on the growth of wild-type D54 tumors and D54 tumors transduced with the E. coli PNP gene

| Treatment | Regressions | | Nonspecific Death/Total | Doubling time | Days Delay T–C | Tumor-free Survival |
|---|---|---|---|---|---|---|
| | Complete | Partial | | | | |
| Wild-type D54 | | | | | | |
| Vehicle | — | — | — | 14 | — | 0/10 |
| MeP-dR (67) | 0/6 | 0/6 | 1/6 | 21 | 7 | 0/6 |
| D54-PNP | | | | | | |
| Vehicle | — | — | — | 17 | — | 0/10 |
| MeP-dR (67) | 6/6 | 0/6 | 0/6 | >56 | >39 | 4/6 |

TABLE V

Effect of MeP-dR on the growth of wild-type D54 tumors and D54 tumors transduced with the *E. coli* PNP gene

| Treatment | Regressions Complete | Regressions Partial | Nonspecific Deaths/Total | Doubling time | Days Delay (T–C) | Tumor-free Survival |
|---|---|---|---|---|---|---|
| Wild-type D54 | | | | | | |
| Vehicle | — | — | — | 12 | — | 0/10 |
| MeP-dR (45) | 0/10 | 0/10 | 0/10 | 17 | 5 | 0/10 |
| MeP-dR (67) | 0/10 | 0/10 | 0/10 | 18 | 6 | 0/10 |
| D54-PNP | | | | | | |
| Vehicle | — | — | — | 30 | — | 0/10 |
| MeP-dR (45) | 2/10 | 3/10 | 0/10 | >54 | >24 | 0/10 |
| MeP-dR (67) | 8/10 | 1/10 | 1/10 | >55 | >25 | 4/10 |

**, Mice (NCr-nu) were implanted (SC) with wild-type D54 tumors or *E. coli* PNP-transduced 16/C tumors (D54-PNP). When tumors had grown to approximately 100 mg, the annnals were treated (IP) with vehicle, 45 or 67 mg/kg of MeP-dR once a day for three days.

These results show that it is possible to cure animals that generate MeP from MeP-dR at the site of the tumor without killing the animal. This is important because MeP is a toxic agent and these results alleviate the concern that doses sufficient to destroy the tumor would release an amount of MeP into the body that would kill the animal. Therefore, these results indicate that the MeP released from PNP-expressing tumors is diluted by body fluids to concentrations below a toxic level. The gene therapy methodology of the present invention, therefore, offers a new way to generate highly toxic chemotherapeutic drugs within a growing tumor, in such a way as to completely eliminate the tumor without undue weight loss or other apparent toxicity. Taken together, the present invention demonstrates the usefulness of a new class of antitumor agents to treat of breast, melanoma, glioma, and other refractory solid tumor types in vivo.

Other additional in vivo experiments indicate that: (1) very large pre-existing tumors (approximately 1 gram in size) transduced with *E. coli* PNP show impressive regression when treated with 67 mg/kg of MeP-dR (ip, qd×3 d); (2) F-araAMP, a clinical useful drug in human, leads to in vivo regression of PNP transduced tumors in mice; (3) 2-F-2'-deoxyadenosine can be given to mice in doses similar to MeP-dR without toxicity, and mediates strong anti-tumor effects, equivalent to or above those seen with MeP-dR. This suggests that 2-F-2'-deoxyadenosine should be a useful prodrug in vivo, since the liberated toxin, 2-F-Ade, is 10 to 100 fold more toxic than MeP.

EXAMPLE 24

Other Prodrugs

In addition to MeP-dR, two other prodrugs suitable for *E. coli* PNP activation in tumor cells can be applied to the methodology of the present invention. These prodrugs are F-araA and 2-F-2'deoxyadenosine. Both show high level killing of PNP-transduced tumor cells in vitro. A dose of 2-F-2'-deoxyadenosine (100 $\mu$M) was defined in the presence of 1 mM deoxycytidine that kills cells transduced with the *E. coli* PNP even when as few as 1% of the tumor cells express the gene. As desired, this dose had no effect on control untransduced, tumor cells. A dose of F-araA (500 ng/ml) also was identified that specifically killed transduced, but not untransduced, tumor cells.

In addition, 21 purine nucleoside analogs were evaluated as substrates for *E. coli* PNP by an independent protocol (Table II). These results have identified 5 compounds as possible prodrugs in this strategy; MeP-dR, 2-F-2'-deoxyadenosine, 1 deaza-2-amino-6-Cl-purine-riboside, 7-ribosyl-3-deazaguanne, and 7-ribosyl-6-mercaptopurine. All of these compounds have the following characteristics: the nucleoside analog is relatively nontoxic when compared to the base of which it is composed, the nucleosides are good substrates for the *E. coli* PNP, and they are poor substrates for the human PNP. Three agents that were poorly cleaved by the *E. coli* PNP but were not cleaved by the human enzyme were 5'-amino-5'-deoxyadenosine, 2-F-arabinofuranosyl-adenine, and α-adenosine. Compounds that were poor substrates for both the human and *E. coli* PNP were also identified. These compounds include xylosyl methylpurine, 2',3'-dideoxyadenosine, 3'-deoxyadenosine, 5'-carboxamide of adenosine, and the isopropylidine of the 5'-carboxamide of adenosine.

Kinetic constants for the cleavage of inosine, MeP-dR, F-dAdo, and F-araA by *E. coli* PNP were determined from enzymes isolated from either transduced human cells or *E. coli* cell pellets (Table VI). The results of these experiments indicated that there were little or no differences between the prokaryotic *E. coli* PNP enzyme in bacteria and after tumor cell expression of the recombinant enzyme. In addition, it was clear that inosine, MeP-dR, and F-dAdo were similar as substrates for recombinant and natural *E. coli* PNP. F-araA was poorly cleaved by *E. coli* PNP with $K_m$ of 543 $\mu$M and $V_{max}$ of 1.9 nmole/mg/minute.

TABLE VI

Kinetic constants of MeP-dR, F-dAdo, and F-araA with *E. coli* PNP

| Sub. | Source | $K_m(\mu M)$ | $V_{max}$ | $V_{max}/K_m$ |
|---|---|---|---|---|
| Inosine | Bacteria | 46 | 132 | 2.9 |
| | D54 cells | — | — | — |
| MeP-dR | Bacteria | 68 | 251 | 3.7 |
| | D54 cells | 107 | 5.4 | 0.050 |
| F-dAdo | Bacteria | 44 | 190 | 4.3 |
| | D54 cells | 38 | 2.1 | 0.056 |
| F-araA | Bacteria | 543 | 1.9 | 0.0034 |
| | D54 cells | 510 | 0.023 | 0.000043 |

EXAMPLE 25

Recombinant *E. coli* that Express 100-Fold More PNP Activity than Wild-Type *E coli* and Use of This Bacterium to Deliver *E. coli* PNP to Tumor Cells Previous studies showed that MeP-dR, F-araAMP, and F-dAdo have good activity against D54 glioma tumors expressing the E. coli PNP gene. MeP-dR, F-araAMP, and F-dAdo were less active against tumors composed of mixtures of wild-type tumor cells and transduced tumor cells at a ratio of 80 to 20, respectively. This result indicated that increased expression of E. coli PNP in the tumor cell may be necessary to demonstrate in vivo bystander activity with these three compounds. The amount of expression of E. coli PNP activity in the transduced D54 tumors cells was between 200 to 300 nmoles of MeP-dR cleaved per mg protein per hour.

Figure 13:
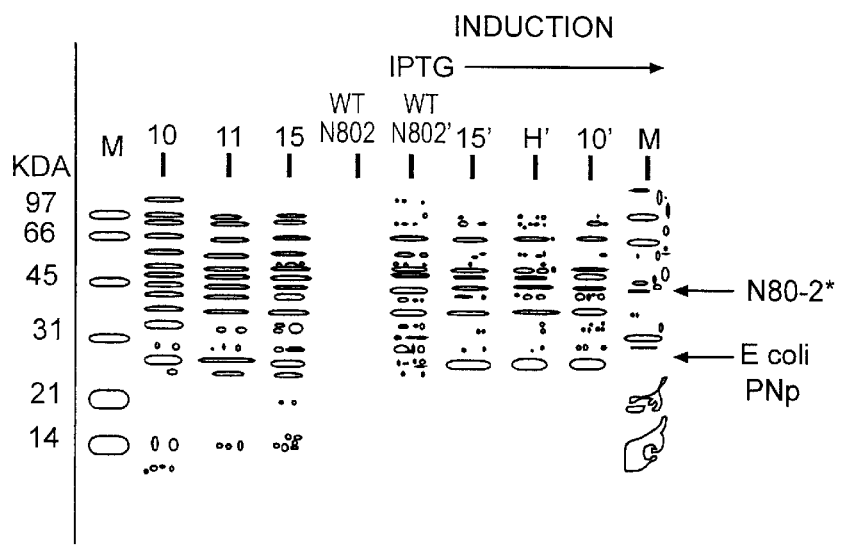
FIG. 13 illustrates the induction of E. coli PNP by IPTG.

In an effort to increase the amount of E. coli PNP expressed in tumor cells and to develop a vector to realistically deliver E. coli PNP to tumors in animals, E. coli was transformed with the E. coli PNP gene (SEQ ID No:5) and created a recombinant E. coli that expressed very high levels of E. coli PNP, approximately 1,000,000 nmoles of MeP-dR cleaved per mg protein per hour. In order to accomplish this, a plasmid capable of mediating high level expression of E. coli PNP was constructed by excising the E. coli PNP (SEQ ID No:5) from a transfer vector (pTM-1 PNP) by a double restriction enzyme digestion with Nco I and Xho I. (see FIG. 12). pTRC His B (Invitrogen, Carlsbad, Calif.) was digested with Nco I and Xho I, and the E. coli PNP fragments described above were directionally ligated into pTRC so as to initiate E. coli PNP translation from the first methionine. The ligation reaction was used to transform competent E. coli by standard techniques. In this case, the DH5α strain was used, but other strains of E. coli or other bacteria could be used for the same purpose. Recombinants were selected on ampicillin, and correct orientation and integration of the insert was verified by restriction mapping. The plasmid is designed to allow further induction of E. coli PNP activity after treatment with isopropyl-α-D-thio-galactopyranoside (IPTG), and in some experiments this induction was verified as additional evidence of the predicted behavior of the recombinant plasmid. FIG. 13 shows a protein band that is present in the recombinant E. coli (Lanes 10, 11, 15) that is inducible with IPTG (Lanes 15', 11', and 10'). No protein was detected in the wild-type strains at this position, or in strains expressing an inducible control protein (WT NBD2 and WT NBD2'). The amount of E. coli PNP in wild-type bacteria was approximately 10,000 nmoles of MeP-dR cleaved per mg protein per hour. Therefore, this recombinant E. coli had 100-fold more E. coli PNP activity than wild-type cells.

Tumors in the flanks of mice were injected with this recombinant E. coli, and the activity of E. coli PNP in the tumors was determined thirty minutes and forty-eight hours after injection of bacteria. After thirty minutes the amount of E. coli PNP activity in the tumors was approximately 100,000 nmoles of MeP-dR cleaved per mg protein per hour, whereas at forty-eight hours the activity in the tumors had increased modestly to approximately 200,000 nmoles of MeP-dR cleaved per mg protein per hour (see Table VII). These results indicated that approximately 1000 times more E. coli PNP could be delivered to tumor cells than was present in the D54-PNP tumors. This result verifies that human patients could be treated by inoculating their tumors with this recombinant bacteria.

TABLE VII

E. coli PNP activity in tumors injected with recombinant E. coli

| Sample | 30 minutes | 40 hours |
|---|---|---|
| 1-1 0.1 ml/tumor | 100,000 | >223,000 |
| -2 | >178,000 | >133,000 |

TABLE VII-continued

E. coli PNP activity in tumors injected with recombinant E. coli

| Sample | 30 minutes | 40 hours |
|---|---|---|
| -3 | 78,000 | >212,000 |
| 2-1 0.2 ml/tumor | >223,000 | >227,000 |
| -2 | >184,000 | >222,000 |
| -3 | >179,000 | >292,000 |

>indicates that there was considerable cleavage of MeP-dR (>40%) at the earliest time measured (fifteen minutes). There was little or no cleavage at zero (0) time. The specific activity was determined from this number which was not in the linear portion of the activity curve. Therefore, these numbers are a slight underestimate of the true activity.

EXAMPLE 26

Treatment of Lewis Lung Tumors with E. coli and MeP-dR

Figure 14:
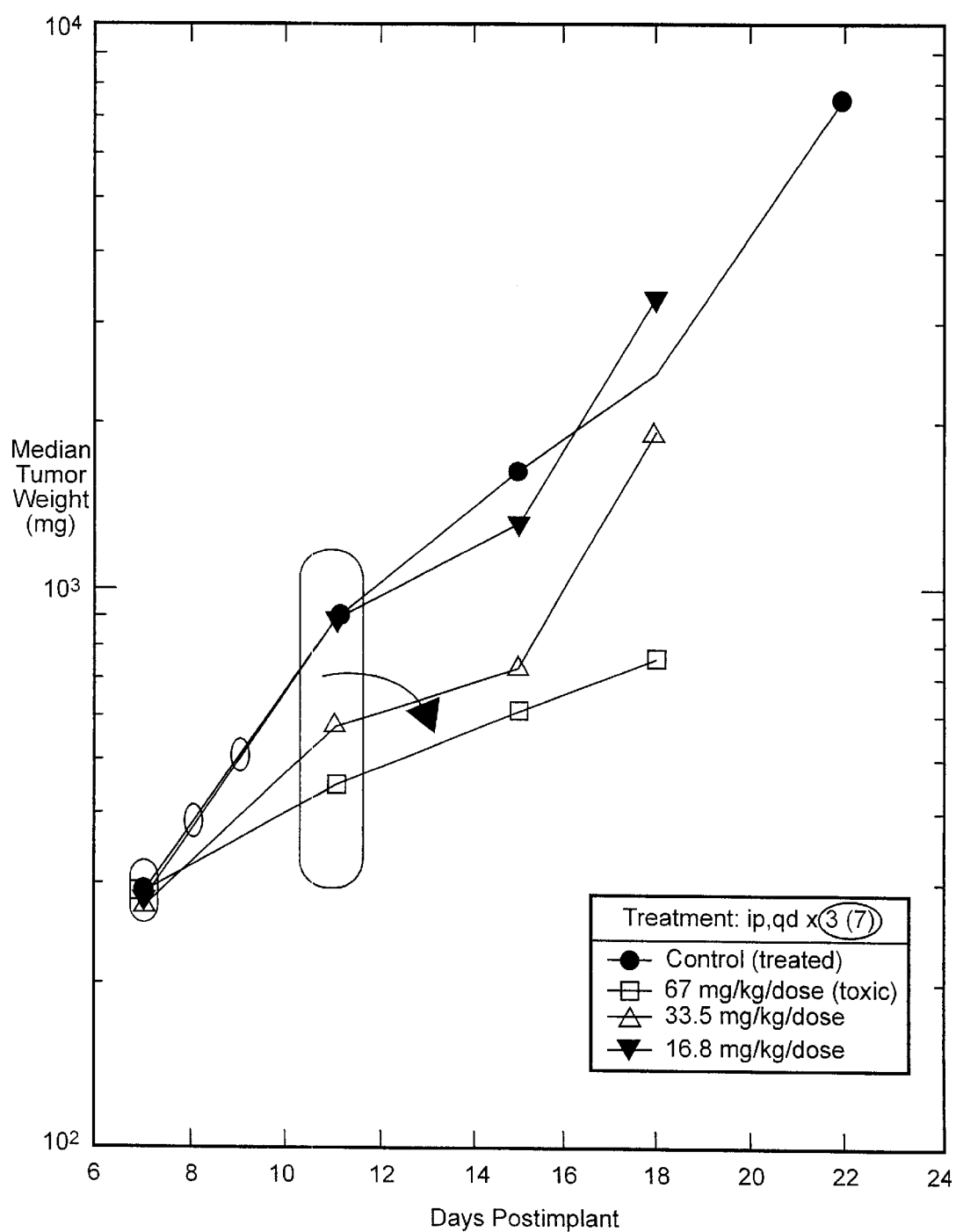
FIG. 14 is a graph of median tumor weight versus the response of SC Lewis Lung Tumors to treatment with MeP-dR and NSC 103543.

Subcutaneous Lewis Lung tumors on the flanks of mice (approximately 300 mg) were injected with E. coli bacteria transfected with E. coli purine nucleoside phosphorylase gene (plasmid pTRCPNP) containing SEQ ID No:5. Mice were treated with 0, 16.8, 33.5, or 67 mg/kg of MeP-dR once a day for three days, and the tumor size was monitored over the following 18 days. The control consisted of saline/Tween 80. This initial experiment was designed for two purposes. First, to determine whether E. coli over-expressing the PNP gene could be given in combination with MeP-dR and without undue toxicity. Second, to evaluate anti-tumor effects in this particular animal model and strain of mouse. E. coli PNP activity was measured thirty minutes and forty-eight hours after injection of bacteria in representative Lewis Lung tumors injected with bacteria but not treated with MeP-dR. The PNP activity was 16,000 and 28,000 nmoles of MeP-dR cleaved per mg protein per hour at 0.5 and forty-eight hours, respectively (each number is the average of two determinations). The anti-tumor results (shown in FIG. 14) indicated that treatment with E. coli bacteria that express E. coli PNP activity plus MeP-dR slowed the growth of these fast growing tumors. In this experiment, treatment with 33.5 mg/kg of MeP-dR delayed tumor growth by approximately 42% without host toxicity. Treatment with a higher dose of MeP-dR (67 mg/kg, IP Qd×3d) was toxic, with several deaths due to the combined therapy. Nevertheless, this treatment arm was informative, since anti-tumor effects were again observed. These results indicated that E. coli bacteria could deliver significant amounts of E. coli PNP to tumor cells in an animal and that this enzyme could activate MeP-dR resulting in an antitumor response.

EXAMPLE 27

Injection of Methyl Purine (MeP) into Established Human Pancreatic Tumors

Figure 16:
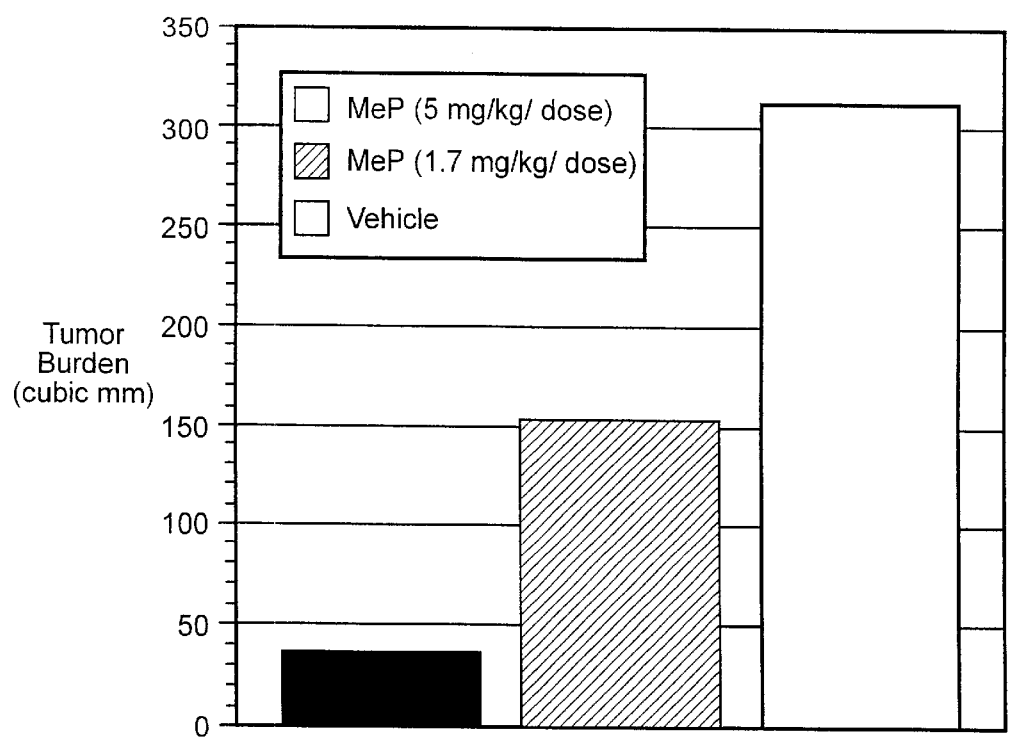
FIG. 16 is a histogram illustrating the tumor burden versus the tumor volume on day 16 following treatment with MeP.
Figure 17:
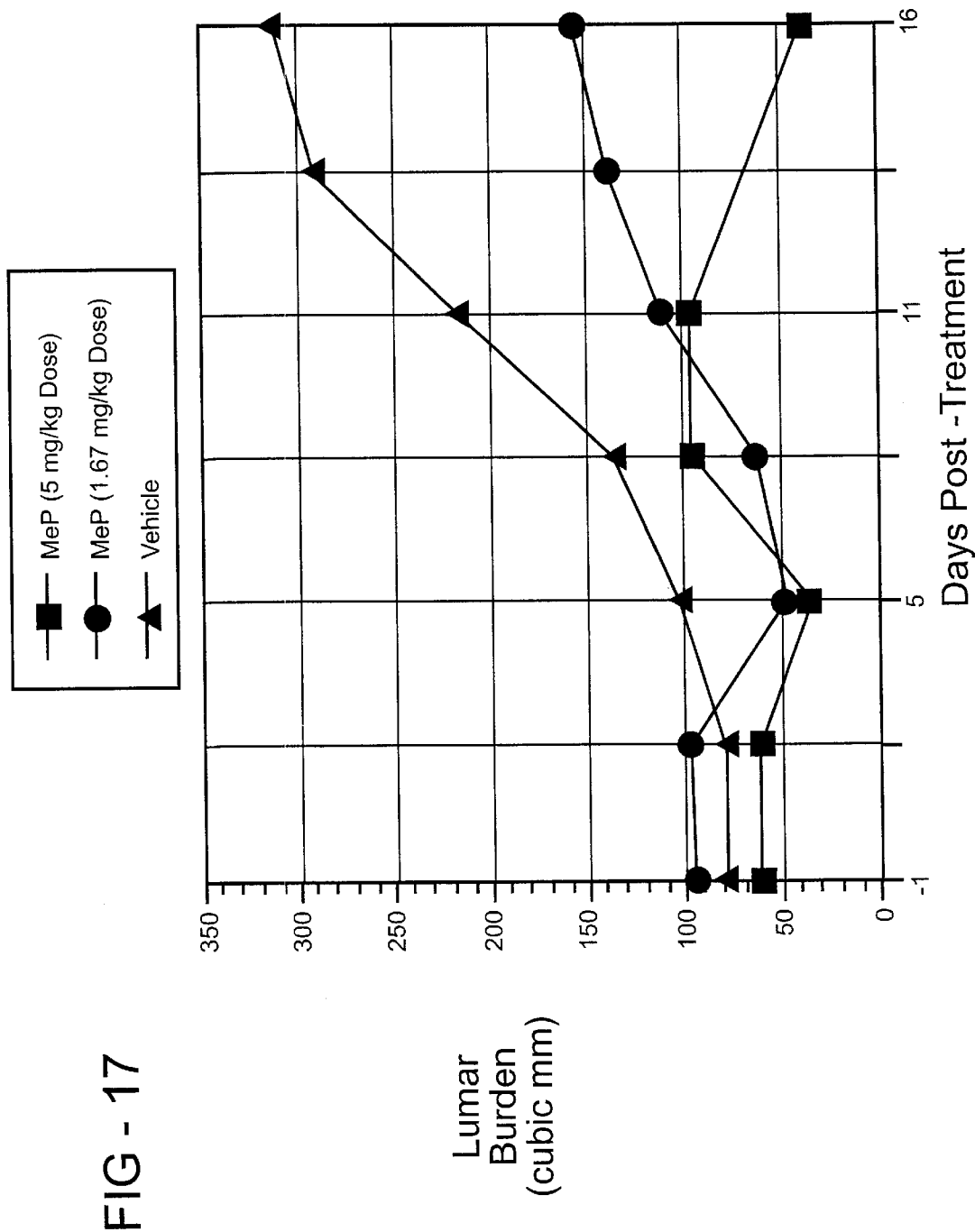
FIG. 17 is a graph illustrating tumor burden over time following treatment with MeP.

CF PAC (human pancreatic adenocarcinoma) cells were grown in T75 flasks, trypsinized, washed with PBS and then inoculated subcutaneously into female SCID mice at approximately $2 \times 10^7$ cells per animal. The tumors were allowed to grow for several days until they reached the size of approximately 80–100 millimeters. At this point, groups of five animals were treated either with vehicle (PBS), PBS containing methyl purine (1.67 mg/kg) or PBS with a higher dose of methyl purine (5.0 mg/kg). Drug or vehicle was injected intratumorally with 3–4 needle passes. Animals were treated with either vehicle or drug one time each day for three days. The growth of the tumors was followed. Measurements in two dimension were used to approximate the overall tumor size. Tumors treated at the higher dose of MeP were completely arrested in terms of their growth, while the lower dose of MeP led to an intermediate effect upon tumor growth. The results (see FIGS. 16 and 17) indicated that MeP has a very potent anti-tumor effect when injected directly into tumors and further support the notion that methyl purine and derivatives thereof is an effective anti-tumor agent, either after direct tumor inoculation or when generated within a tumor by virtue of expression of the E. coli PNP gene. The results also suggest that direct inter-tumoral injection of cytotoxic purine analogs or other cytotoxic drugs can elicit profound anti-tumor effects in vivo. For example, purine analogs which are known to have strong cytotoxic activity such as 2-fluoroadenine, 2-fluoroadenosine, 9-[ribosyl]-6-methylpurine, 2-amino-6-chloro-1-deazapurine, 3-deazaguanine, 6-thioguanine, and 6-mercaptopurine can be directly administered to a tumor to cause regression and/or inhibit tumor growth.

SUMMARY

The following data summarizes in vitro and in vivo experiments in which the efficacy of the claimed delivery vehicles and methods were further demonstrated. Experiments to show the killing of cancer cells in vitro used mixed populations of PNP expressing and nonexpressing cells. The results demonstrated that a small population of PNP expressing cells can facilitate the death of large numbers of surrounding, non-PNP expressing cells. In vivo efficacy was demonstrated by implanting into mice transduced and non-transduced tumor cells. Tumor size decreased in mice implanted with PNP-transduced tumor cells upon the administration of a prodrug purine analog. The results indicate that the claimed methods are applicable to the treatment of mammalian malignant disorders.

The results provided were generated using art recognized in vivo and in vitro models of mammalian malignancy. These results demonstrate that: (1) a small number of PNP expressing tumor cells can facilitate in the killing of surrounding, non-PNP expressing cells, (2) PNP expression can be controlled in a tissue specific fashion, (3) the claimed therapeutic method works with a variety of tumor types in art recognized models of mammalian malignancy, and (4) that purine analogs such as methyl purine can be used to inhibit tumor growth.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A vector comprising a DNA sequence encoding an *E. coli* derived purine nucleoside phosphorylase (PNP), said DNA sequence consisting of SEQ ID No. 5.

2. The vector as set forth in claim 1, wherein said vector is a plasmid.

3. The vector as set forth in claim 2, wherein said plasmid is pTRCPNP.

4. A prokaryotic host cell stably transformed or transfected by a vector comprising a DNA sequence encoding an *E. coli* derived purine nucleoside phosphorylase designated SEQ ID No. 5.

5. The procaryotic host cell as set forth in claim 4, wherein said procaryotic host cell is *E. coli*.

6. The procaryotic host cell as set forth in claim 4, wherein said vector is a plasmid.

7. The procaryotic host cell as set forth in claim 6, wherein said plasmid comprises pTRCPNP.

8. The procaryotic host cell as set forth in claim 1, wherein said procaryotic host cell produces sufficient PNP to cleave approximately 1,000,000 nmoles of MeP-dR per mg protein per hour, in vitro.

9. A method for killing targeted replicating or nonreplicating mammalian cells and bystander cells, said method comprising:

administering a transformed prokaryotic host cell being obtained by transfecting a prokaryotic host cell with a DNA sequence encoding purine nucleoside phosphorylase or hydrolase by a method selected from the group consisting of: a) delivering an effective amount of a transformed prokaryotic host cell selected from the group consisting of: Salmonella and Clostridium host cells to mammalian cells by way of intravenous or intraperitoneal injection, and, b) delivering an effective amount of a transformed prokaryotic host cell to a mammalian tumor intratumorally;

and contacting the mammalian cells treated with said transformed prokaryotic host cell with an effective amount of a substrate for the purine nucleoside phosphorylase or hydrolase, wherein the substrate is substantially non-toxic to mammalian cells and is cleaved by the purine nucleoside phosphorylase to yield a purine analog toxic to the mammalian cells.

10. The method according to claim 9, wherein the targeted cells include tumor cells.

11. The method according to claim 9, wherein the purine analog is selected from the group consisting of 9-(β-D-2-deoxyerythropentofuranosyl)-6-methypurine, 2-amino-6-chloro-1-deazapurine riboside, 7-ribosyl-3-deazaguanine, arabinofuranosyl-2-fluoroadenine, 2-fluoro-2'-deoxyadenosine, 2-fluoro-5'-deoxyadenosine, 2-chloro-2'-deoxy-adenosine, 5'-amino-5'-deoxy-adenosine, α-adenosine, MeP-2',3'-dideoxyriboside, 2-F-2',3'-dideoxyadenosine, MeP-3'-deoxyriboside, 2-F-3'-deoxyadenosine, 2-F-adenine-6'-deoxy-β-D-allofuranoside, 2-F-adenine-α-L-lyxofuranoside, MeP-6'-deoxy-β-D-allofuranoside, MeP-α-L-lyxofuranoside, 2-F-adenine-6'-deoxy-α-L-talofuranoside, and MeP-6'-deoxy-α-L-talofuranoside.

12. The method as set forth in claim 9, wherein the procaryotic host cell is *E. coli.*

13. The method as set forth in claim 12, wherein the plasmid is PTRCPNP.

14. The method as set forth in claim 9, wherein the DNA sequence is inserted into a plasmid.

15. The method as set forth in claim 9, wherein the DNA sequence encoding said PNP consists of SEQ ID No. 5.

16. A method of killing replicating or non-replicating mammalian cells and bystander cells, comprising:

contacting the mammalian cells with a bacteria selected from the group consisting of Salmonella and Clostridium that targets tumor cells, the bacteria containing a nucleic acid sequence encoding a purine cleavage enzyme that cleaves an adenosine, wherein the enzyme is a naturally expressed component of the bacteria that targets tumor cells and the contact is by way of direct tumoral, intravenous or intraperitoneal injection; and contacting the mammalian cells with an effective amount of a substrate for the adenosine cleaving purine cleavage enzyme, wherein the substrate is substantially non-toxic to mammalian cells and is cleaved by the enzyme to yield a purine analog toxic to the mammalian cells and the bystander cells, to kill the mammalian cells and the bystander cells.

17. The method according to claim 16, wherein the mammalian cells to be killed are selected from the group consisting of tumor cells and non-neoplastic abnormally proliferating cells.

18. The method according to claim 16, wherein the purine cleavage enzyme is a purine nucleoside phosphorylase.

19. The method according to claim 16, wherein the purine cleavage enzyme is a nucleoside hydrolase.

20. The method of claim 16, wherein the substrate is selected from the group consisting of 9-(β-D-2-deoxyerythropentofuranosyl)-6-methylpurine, 2-amino-6-chloro-1-deazapurine riboside, 7-ribosyl-3-deazaguanine, arabinofuranosyl-2-fluoroadenine, 2-fluoro-2'-deoxyadenosine, 2-fluoro-5'deoxyadenosine, 2-chloro-2'-deoxy-adenosine, 5'-amino-5'-deoxy-adenosine, α-adenosine, MeP-2',3'-dideoxyriboside, 2-F-2',3'-dideoxyadenosine, MeP-3'-deoxyriboside, 2-F-3'-deoxyadenosine, 2-F-adenine-6'-deoxy-β-D-allofuranoside, 2-F-adenine-α-L-lyxofuranoside, MeP-6'-deoxy-β-D-allofuranoside, MeP-α-L-lyxofuranoside, 2-F-adenine-6'-deoxy-α-L-talofuranoside, MeP-6'-deoxy-α-L-talofuranoside and 7-ribosyl-thioguanine.

21. A method for killing targeted replicating or nonreplicating mammalian cells and bystander cells, said method comprising:

administering a Clostridium spore being obtained from a Clostridium host cell transfected with a DNA sequence encoding purine nucleoside phosphorylase or hydrolase by a method selected from the group consisting of: a) delivering an effective amount of Clostridium spore to mammalian cells by way of intravenous or intraperitoneal injection, and b) delivering an effective amount of a Clostridium spore to a mammalian tumor intratumorally;

and contacting the mammalian cells treated with said Clostridium spore with an effective amount of a substrate for the purine nucleoside phosphorylase or hydrolase, wherein the substrate is substantially non-toxic to mammalian cells and is cleaved by the purine nucleoside phosphorylase to yield a purine analog toxic to the mammalian cells.

* * * * *

UNITED STATES PATENT AND TRADEMARK OFFICE
CERTIFICATE OF CORRECTION

PATENT NO. : 6,491,905 B1
DATED : December 10, 2002
INVENTOR(S) : Eric J. Sorscher It is certified that error appears in the above-identified patent and that said Letters Patent is hereby corrected as shown below:

Column 6,
Line 28, replace "HSV Thd" with -- HSV dThd --.
Line 62, replace "Plasinodium" with -- Plasmodium --.

Column 18,
Line 18, replace "(5 $\mu$l)" with -- (5 $\mu$m) --

Column 23,
Line 55, before "O(85**)" insert -- # --.

Column 27,
Table III, the table heading and content should read like this:

-- TABLE III
Effect of MeP-dR and F-araAMP on the growth of wild-type 16/C tumors and 16/C tumors transduced with the *E. coli* PNP gene (B6C3F1)

| Treatment delay control) | Dose/day** (mg/kg) | Complete Regressions/ Total | Nonspecific Deaths/Total | Days for tumor to double 3 times * mean/SD | Day (Treated- |
|---|---|---|---|---|---|
| Wild-type 16/C | | | | | |
| Vehicle | - | 0/6 | - | 6.2±3.7 | - |
| MeP-dR | 100 | 0/6 | 0/6 | 8.6±0.7 | 2.4 |
| F-araAMP | 500 | 0/6 | 0/6 | 8.9±2.0 | 2.7 |
| 16/C-PNP | | | | | |
| Vehicle | - | 0/6 | - | 8.8±1.1 | - |
| MeP-dR | 100 | 3/6 | 2/6**** | 14.2±3.2*** | 5.4 |
| F-araAMP | 500 | 0/6 | 0/6 | 1 2.1+1.6* * * | 3.3 -- |

UNITED STATES PATENT AND TRADEMARK OFFICE
CERTIFICATE OF CORRECTION

PATENT NO.   : 6,491,905 B1
DATED        : December 10, 2002
INVENTOR(S)  : Eric J. Sorscher It is certified that error appears in the above-identified patent and that said Letters Patent is hereby corrected as shown below:

Column 28,
Table III, 5th line under formula, replace "annals" with -- animals --.

Column 30,
Line 25, replace "of" with -- or --.

Column 31,
Table V, 2nd line under formula, replace "annals" with -- animals --.

Column 41,
Line 59, replace "claim 1" with -- claim 4 --.

Column 42,
Line 63, replace "methypurine" with -- methylpurine --

Signed and Sealed this

Twenty-second Day of June, 2004

JON W. DUDAS
*Acting Director of the United States Patent and Trademark Office*

```
                          SEQUENCE LISTING

<160> NUMBER OF SEQ ID NOS: 7

<210> SEQ ID NO 1
<211> LENGTH: 37
<212> TYPE: DNA
<213> ORGANISM: Escherichia coli

<400> SEQUENCE: 1
gatcgcggcc gcatggctac cccacacatt aatgcag                          37

<210> SEQ ID NO 2
<211> LENGTH: 45
<212> TYPE: DNA
<213> ORGANISM: Escherichia coli

<400> SEQUENCE: 2
gtacgcggcc gcttactctt tatcgcccag cagaacggat tccag                 45

<210> SEQ ID NO 3
<211> LENGTH: 36
<212> TYPE: DNA
<213> ORGANISM: Escherichia coli

<400> SEQUENCE: 3
gatcgctagc gggctctgaa gacaatctct ctctgc                           36

<210> SEQ ID NO 4
<211> LENGTH: 35
<212> TYPE: DNA
<213> ORGANISM: Escherichia coli
```

<400> SEQUENCE: 4
gatcgctagc tcttcctcta gtcctcacaa ggtct                                    35

<210> SEQ ID NO 5
<211> LENGTH: 5013
<212> TYPE: DNA
<213> ORGANISM: Escherichia coli

<400> SEQUENCE: 5

| | |
|---|---|
| gtttgacagc ttatcatcga ctgcacggtg caccaatgct tctggcgtca ggcagccatc | 60 |
| ggaagctgtg gtatggctgt gcaggtcgta atcactgca taattcgtgt cgctcaaggc | 120 |
| gcactcccgt tctggataat gttttttgcg ccgacatcat aacggttctg caaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggctac | 420 |
| cccacacatt aatgcagaaa tgggcgattt cgctgacgta gttttgatgc caggcgaccc | 480 |
| gctgcgtgcg aagtatattg ctgaaacttt ccttgaagat gcccgtgaag tgaacaacgt | 540 |
| tcgcggtatg ctgggcttca ccggtactta caaaggccgc aaaatttccg taatgggtca | 600 |
| cggtatgggt atcccgtcct gctccatcta caccaaagaa ctgatcaccg atttcggcgt | 660 |
| gaagaaaatt atccgcgtgg gttcctgtgg cgcagttctg ccgcacgtaa aactgcgcga | 720 |
| cgtcgttatc ggtatgggtg cctgcaccga ttccaaagtt aaccgcatcc gttttaaaga | 780 |
| ccatgacttt gccgctatcg ctgacttcga catggtgcgt aacgcagtag atgcagctaa | 840 |
| agcactgggt attgatgctc gcgtgggtaa cctgttctcc gctgacctgt tctactctcc | 900 |
| ggacggcgaa atgttcgacg tgatggaaaa atacggcatt ctcggcgtgg aaatggaagc | 960 |
| ggctggtatc tacggcgtcg ctgcagaatt tggcgcgaaa gccctgacca tctgcaccgt | 1020 |
| atctgaccac atccgcactc acgagcagac cactgccgct gagcgtcaga ctaccttcaa | 1080 |
| cgacatgatc aaaatcgcac tggaatccgt tctgctgggc gataaagagt aaagagtaaa | 1140 |
| tcgatggcct gaattcgaag cttggctgtt ttggcggatg agagaagatt ttcagcctga | 1200 |
| tacagattaa atcagaacgc agaagcggtc tgataaaaca gaatttgcct ggcggcagta | 1260 |
| gcgcggtggt cccacctgac cccatgccga actcagaagt gaaacgccgt agcgccgatg | 1320 |
| gtagtgtggg gtctccccat gcgagagtag ggaactgcca ggcatcaaat aaaacgaaag | 1380 |
| gctcagtcga aagactgggc ctttcgtttt atctgttgtt tgtcggtgaa cgctctcctg | 1440 |
| agtaggacaa atccgccggg agcggatttg aacgttgcga agcaacggcc cggagggtgg | 1500 |
| cgggcaggac gcccgccata aactgccagg catcaaatta gcagaaggc catcctgacg | 1560 |
| gatggccttt tgcgtttct acaaactctt tttgtttatt tttctaaata cattcaaata | 1620 |
| tgtatccgct catgagacaa taaccctgat aaatgcttca ataatattga aaaggaaga | 1680 |
| gtatgagtat tcaacatttc cgtgtcgccc ttattccctt ttttgcggca ttttgccttc | 1740 |
| ctgtttttgc tcacccagaa acgctggtga agtaaaaga tgctgaagat cagttgggtg | 1800 |
| cacgagtggg ttacatcgaa ctggatctca acagcggtaa gatccttgag agttttcgcc | 1860 |
| ccgaagaacg ttttccaatg atgagcactt ttaaagttct gctatgtggc gcggtattat | 1920 |
| cccgtgttga cgccgggcaa gagcaactcg gtcgccgcat acactattct cagaatgact | 1980 |

```
tggttgagta ctcaccagtc acagaaaagc atcttacgga tggcatgaca gtaagagaat   2040
tatgcagtgc tgccataacc atgagtgata acactgcggc caacttactt ctgacaacga   2100
tcggaggacc gaaggagcta accgcttttt tgcacaacat gggggatcat gtaactcgcc   2160
ttgatcgttg ggaaccggag ctgaatgaag ccataccaaa cgacgagcgt gacaccacga   2220
tgcctgtagc aatggcaaca acgttgcgca aactattaac tggcgaacta cttactctag   2280
cttcccggca acaattaata gactggatgg aggcggataa agttgcagga ccacttctgc   2340
gctcggccct tccggctggc tggtttattg ctgataaatc tggagccggt gagcgtgggt   2400
ctcgcggtat cattgcagca ctggggccag atggtaagcc ctcccgtatc gtagttatct   2460
acacgacggg gagtcaggca actatggatg aacgaaatag acagatcgct gagataggtg   2520
cctcactgat taagcattgg taactgtcag accaagttta ctcatatata ctttagattg   2580
atttaaaact tcatttttaa tttaaaagga tctaggtgaa gatccttttt gataatctca   2640
tgaccaaaat cccttaacgt gagttttcgt tccactgagc gtcagacccc gtagaaaaga   2700
tcaaaggatc ttcttgagat cctttttttc tgcgcgtaat ctgctgcttg caaacaaaaa   2760
aaccaccgct accagcggtg gtttgtttgc cggatcaaga ctaccaact cttttccga    2820
aggtaactgg cttcagcaga gcgcagatac caaatactgt ccttctagtg tagccgtagt   2880
taggccacca cttcaagaac tctgtagcac cgcctacata cctcgctctg ctaatcctgt   2940
taccagtggc tgctgccagt ggcgataagt cgtgtcttac cgggttggac tcaagacgat   3000
agttaccgga taaggcgcag cggtcgggct gaacggggggttcgtgcaca cagcccagct   3060
tggagcgaac gacctacacc gaactgagat acctacagcg tgagctatga aaagcgcca    3120
cgcttcccga agggagaaag gcggacaggt atccggtaag cggcagggtc ggaacaggag   3180
agcgcacgag ggagcttcca ggggaaacg cctggtatct ttatagtcct gtcgggtttc    3240
gccacctctg acttgagcgt cgatttttgt gatgctcgtc agggggggcgg agcctatgga   3300
aaaacgccag caacgcggcc ttttacggt tcctggcctt tgctggcct tttgctcaca     3360
tgttctttcc tgcgttatcc cctgattctg tggataaccg tattaccgcc tttgagtgag   3420
ctgataccgc tcgccgcagc cgaacgaccg agcgcagcga gtcagtgagc gaggaagcgg   3480
aagagcgcct gatgcggtat tttctcctta cgcatctgtg cggtatttca caccgcatat   3540
ggtgcactct cagtacaatc tgctctgatg ccgcatagtt aagccagtat acactccgct   3600
atcgctacgt gactgggtca tggctgcgcc ccgacacccg ccaacacccg ctgacgcgcc   3660
ctgacgggct tgtctgctcc cggcatccgc ttacagacaa gctgtgaccg tctccgggag   3720
ctgcatgtgt cagaggtttt caccgtcatc accgaaacgc gcgaggcagc agatcaattc   3780
gcgcgcgaag gcgaagcggc atgcatttac gttgacacca tcgaatggtg caaaaccttt   3840
cgcggtatgg catgatagcg cccggaagag agtcaattca gggtggtgaa tgtgaaacca   3900
gtaacgttat acgatgtcgc agagtatgcc ggtgtctctt atcagaccgt ttcccgcgtg   3960
gtgaaccagg ccagccacgt ttctgcgaaa acgcgggaaa aagtggaagc ggcgatggcg   4020
gagctgaatt acattcccaa ccgcgtggca caacaactgg cgggcaaaca gtcgttgctg   4080
attggcgttg ccacctccag tctggccctg cacgcgccgt cgcaaattgt cgcggcgatt   4140
aaatctcgcg ccgatcaact gggtgccagc gtggtggtgt cgatggtaga acgaagcggc   4200
gtcgaagcct gtaaagcggc ggtgcacaat cttctcgcgc aacgcgtcag tgggctgatc   4260
attaactatc cgctggatga ccaggatgcc attgctgtga agctgcctg cactaatgtt   4320
ccggcgttat tcttgatgt ctctgaccag acacccatca acagtattat tttctcccat    4380
```

```
gaagacggta cgcgactggg cgtggagcat ctggtcgcat tgggtcacca gcaaatcgcg    4440
ctgttagcgg gcccattaag ttctgtctcg gcgcgtctgc gtctggctgg ctggcataaa    4500
tatctcactc gcaatcaaat tcagccgata gcggaacggg aaggcgactg gagtgccatg    4560
tccggttttc aacaaaccat gcaaatgctg aatgagggca tcgttccac tgcgatgctg     4620 gttgccaacg atcagatggc gctgggcgca atgcgcgcca ttaccgagtc cgggctgcgc    4680
gttggtgcgg atatctcggt agtgggatac gacgataccg aagacagctc atgttatatc    4740
ccgccgttaa ccaccatcaa acaggatttt cgcctgctgg ggcaaaccag cgtggaccgc    4800
ttgctgcaac tctctcaggg ccaggcggtg aagggcaatc agctgttgcc cgtctcactg    4860
gtgaaaagaa aaaccaccct ggcgcccaat acgcaaaccg cctctccccg cgcgttggcc    4920
gattcattaa tgcagctggc acgacaggtt tcccgactgg aaagcgggca gtgagcgcaa    4980
cgcaattaat gtgagttagc gcgaattgat ctg                                5013
```

<210> SEQ ID NO 6
<211> LENGTH: 34
<212> TYPE: DNA
<213> ORGANISM: Artificial Sequence
<220> FEATURE:
<223> OTHER INFORMATION: Synthetic polymerase chain reaction primer

<400> SEQUENCE: 6
gatcgctagc gggctgaaga caatctctct ctgc    34

<210> SEQ ID NO 7
<211> LENGTH: 33
<212> TYPE: DNA
<213> ORGANISM: Artificial Sequence
<220> FEATURE:
<223> OTHER INFORMATION: Synthetic polymerase chain reaction primer

<400> SEQUENCE: 7
gatcgctagc ttcctctagt cctcacaagg tct    33